United States Patent
Zhao et al.

(10) Patent No.: US 10,350,204 B2
(45) Date of Patent: *Jul. 16, 2019

(54) METHODS FOR TREATING COGNITIVE DEFICITS ASSOCIATED WITH FRAGILE X SYNDROME

(71) Applicant: Wisconsin Alumni Research Foundation, Madison, WI (US)

(72) Inventors: Xinyu Zhao, Madison, WI (US); Yue Li, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/915,278

(22) Filed: Mar. 8, 2018

(65) Prior Publication Data

US 2018/0200251 A1  Jul. 19, 2018

Related U.S. Application Data

(62) Division of application No. 15/274,983, filed on Sep. 23, 2016, now Pat. No. 9,962,380.

(60) Provisional application No. 62/222,267, filed on Sep. 23, 2015.

(51) Int. Cl.
 *A61K 31/496* (2006.01)
 *A61K 31/404* (2006.01)

(52) U.S. Cl.
 CPC .......... *A61K 31/496* (2013.01); *A61K 31/404* (2013.01)

(58) Field of Classification Search
 CPC ........................ A61K 31/404; A61K 31/496
 See application file for complete search history.

(56) References Cited

U.S. PATENT DOCUMENTS

| | | | |
|---|---|---|---|
| 6,107,025 A | 8/2000 | Caskey | |
| 6,180,337 B1 | 1/2001 | Caskey | |
| 7,737,174 B2 | 6/2010 | Wang | |
| 7,759,383 B2 | 7/2010 | Wang | |
| 8,658,170 B2 | 2/2014 | Errico | |
| 9,079,913 B2 | 7/2015 | Wang | |
| 9,701,685 B2 * | 7/2017 | Chen | C07D 487/10 |
| 2013/0331398 A1 | 12/2013 | Morabito et al. | |
| 2014/0243372 A1 * | 8/2014 | Rew | C07D 211/76 514/327 |
| 2015/0299211 A1 * | 10/2015 | Wang | C07D 487/10 514/409 |

OTHER PUBLICATIONS

WebAIM article (2013 pp. 1-4, downloaded from the internet on Jul. 27, 2017, http://webaim.org/articles/cognitive/).*
Trivedi (Indian J Psychiatry, 2006, 48(1):1-21).*
(Continued)

*Primary Examiner* — Savitha M Rao
(74) *Attorney, Agent, or Firm* — Quarles & Brady LLP

(57) ABSTRACT

Provided herein are methods of treating a cognitive deficit, including cognitive deficits associated with a Fmr1 genetic defect. More particularly, provided herein are methods in which an effective amount of a MDM2-p53 pathway inhibitor is administered to a subject afflicted with at least one cognitive deficit, whereby administration of the inhibitor improves, enhances, or rescues at least one cognitive deficit in the subject.

11 Claims, 29 Drawing Sheets
(26 of 29 Drawing Sheet(s) Filed in Color)
Specification includes a Sequence Listing.

(56) References Cited

OTHER PUBLICATIONS

Cornish et al. (Cortex 44, 2008; 628-636).*
Li et al, Science translational medicine, 2016. (336) pp. 1-15.*
Lu, et al., The fragile X protein controls microtubule-associated protein 1B translation and microtubule stability in brain neuron development. Proc Natl Acad Sci U S A 101, 15201-15206 (2004).
Luo et al., Fragile x mental retardation protein regulates proliferation and differentiation of adult neural stem/progenitor cells, PLoS Genet. Apr. 8, 2010;6(4), pp. 1-15.
Manfredi, The Mdm2-p53 relationship evolves: Mdm2 swings both ways as an oncogene and a tumor suppressor. Genes Dev 24, 1580-1589 (2010).
Meek, et al., The regulation of MDM2 by multisite phosphorylation— opportunities for molecular-based intervention to target tumours? Semin Cancer Biol 20, 19-28 (2010).
Montes de Oca Luna, et al., Rescue of early embryonic lethality in mdm2-deficient mice by deletion of p53. Nature 378, 203-206 (1995).
Morrison, et al., The role of p53 in neuronal cell death. Cell Death Differ 7, 868-879 (2000).
Mouraret, et al. Activation of lung p53 by Nutlin-3a prevents and reverses experimental pulmonary hypertension. Circulation 127, 1664-1676 (2013).
Moy et al., Mouse models of autism spectrum disorders: the challenge for behavioral genetics, Am. J. Med. Genetics Part C 142C:40-51 (2006).
Mullard, Fragile X disappointments upset autism ambitions. Nat Rev Drug Discov 14, 151-153 (2015).
Ogawara, et al., Akt enhances Mdm2-mediated ubiquitination and degradation of p53. Journal of Biological Chemistry 277, 21843-21850 (2002).
Oliner et al., Amplification of a gene encoding a p53-associated protein in human sarcomas, Nature 1993 362:857-860.
Overall, et al., The mammalian adult neurogenesis gene ontology (MANGO) provides a structural framework for published information on genes regulating adult hippocampal neurogenesis. PLoS One 7, e48527 (2012).
Rafalski, et al. Expansion of oligodendrocyte progenitor cells following SIRT1 inactivation in the adult brain. Nat Cell Biol 15, 614-+ (2013).
Secchiero, et al., Recent advances in the therapeutic perspectives of Nutlin-3. Current pharmaceutical design 17, 569-577 (2011).
T. D.-B. F. X. Consortium, Fmr1 knockout mice: a model to study fragile X mental retardation. The Dutch-Belgian Fragile X Consortium. Cell 78, 23-33 (1994).
Tedeschi, et al., The non-apoptotic role of p53 in neuronal biology: enlightening the dark side of the moon. EMBO Rep 10, 576-583 (2009).
Tovar, et al., Small molecule MDM2 antagonists reveal aberrant p53 signaling in cancer: implications for therapy. Proc Natl Acad Sci U S A 103, 1888-1893 (2006).
Tsai, et al., Multiple autism-linked genes mediate synapse elimination via proteasomal degradation of a synaptic scaffold PSD-95. Cell 151, 1581-1594 (2012).
Udagawa, et al., Genetic and acute CPEB1 depletion ameliorate fragile X pathophysiology. Nat Med 19, 1473-+ (2013).
Vassilev, p53 Activation by small molecules: application in oncology, 2005 J Med Chem 48, 4491-4499.
Vassilev, et al., In vivo activation of the p53 pathway by small-molecule antagonists of MDM2. Science 303, 844-848 (2004).
Wang, et al. Protein-Protein Interactions, M. D. Wendt, Ed. (Springer Berlin Heidelberg, 2012), pp. pp. 57-79.
Wang, et al., Expression of Mutant p53 Proteins Implicates a Lineage Relationship between Neural Stem Cells and Malignant Astrocytic Glioma in a Murine Model. Cancer Cell 15, 514-526 (2009).
Wang, et al., New perspectives on the biology of fragile X syndrome. Curr Opin Genet Dev 22, 256-263 (2012).
Yamaguchi, et al., Visualization of neurogenesis in the central nervous system using nestin promoter-GFP transgenic mice. Neuroreport 11, 1991-1996 (2000).
Ye, et al., Nutlin-3 induces apoptosis, disrupts viral latency and inhibits expression of angiopoietin-2 in Kaposi sarcoma tumor cells. Cell Cycle 11, 1393-1399 (2012).
Yuskaitis, et al., Lithium ameliorates altered glycogen synthase kinase-3 and behavior in a mouse model of Fragile X syndrome. Biochem Pharmacol 79, 632-646 (2010).
Zhao et al., Mice lacking methyl-CpG binding protein 1 have deficits in adult neurogenesis and hippocampal function, Proc Natl Acad Sci U S A 100, 6777-6782 (2003).
Zheng, et al., Nutlin-3 overcomes arsenic trioxide resistance and tumor metastasis mediated by mutant p53 in Hepatocellular Carcinoma. Mol Cancer 13, 133 (2014).
Zhou, et al., HER-2/neu induces p53 ubiquitination via Akt-mediated MDM2 phosphorylation (vol. 3, p. 973, 2001). Nat Cell Biol 4, 736-736 (2002).
Zhou, et al. mTOR Inhibition Ameliorates Cognitive and Affective Deficits Caused by Disc1 Knockdown in Adult-Born Dentate Granule Neurons. Neuron 77, 647-654 (2013).
Ahn, et al., Results of an abbreviated phase-II study with the Akt Inhibitor MK-2206 in Patients with Advanced Biliary Cancer. Sci Rep 5, 12122 (2015).
Amson, et al., Behavioral alterations associated with apoptosis and down-regulation of presenilin 1 in the brains of p53-deficient mice. Proc Natl Aced Sci USA 97, 5346-5350 (2000).
Ascano, et al., FMRP targets distinct mRNA sequence elements to regulate protein expression. Nature 492, 382-+ (2012).
Baba, et al., Fragile X-associated tremor/ataxia syndrome and movements disorders, Current Opinion in Neurology 18:393-398 (2005).
Berry-Kravis, Mechanism-Based Treatments in Neurodevelopmental Disorders: Fragile X Syndrome. Pediatr Neurol 50, 297-302 (2014).
Bonaguidi, et al., In vivo clonal analysis reveals self-renewing and multipotent adult neural stem cell characteristics. Cell 145, 1142-1155 (2011).
Brown, et al., Microarray identification of FMRP-associated brain mRNAs and altered mRNA translational profiles in fragile X syndrome. Cell 107, 477-487 (2001).
Busquets-Garcia, et al. Targeting the endocannabinoid system in the treatment of fragile X syndrome. Nat Med 19, 603-607 (2013).
Callan, et al. Fragile X Protein is required for inhibition of insulin signaling and regulates glial-dependent neuroblast reactivation in the developing brain. Brain Res 1462, 151-161 (2012).
Carry, et al., Inhibitors of the p53/hdm2 protein-protein interaction path to the clinic. Bioorg Med Chem Lett 23, 2480-2485 (2013).
Lu et al., Discovery of a nanomolar inhibitor of the human murine double minute 2 (MDM2)-p53 interaction through an integrated, virtual database screening strategy, 2006 J Med Chem 49, 3759-3762.
Chen et al., Mapping of the p53 and mdm-2 interaction domains, Mol. Cell Biol. 1993 13:4107-4114.
Chene, Inhibiting the p53-MDM2 interaction: an important target for cancer therapy, 2003 Nat. Rev. Cancer 3, 102-109.
Christian, et al., Functions and Dysfunctions of Adult Hippocampal Neurogenesis. Annu Rev Neurosci 37, 243-262 (2014).
Contestabile, et al., Lithium rescues synaptic plasticity and memory in Down syndrome mice. J Clin Invest 123, 348-361 (2013).
Contractor, et al., Altered Neuronal and Circuit Excitability in Fragile X Syndrome. Neuron 87, 699-715 (2015).
Darnell, et al., FMRP Stalls Ribosomal Translocation on mRNAs Linked to Synaptic Function and Autism. Cell 146, 247-261 (2011).
De Rubeis, et al., Fragile X mental retardation protein control of neuronal mRNA metabolism: Insights into mRNA stability. Molecular and Cellular Neuroscience 43, 43-50 (2010).
Ding et al., Structure-based design of spiro-oxindoles as potent, specific small-molecule inhibitors of the MDM2-p53 interaction, 2006 J Med Chem 49, 3432-3435.
Ding, et al., Structure-based design of potent non-peptide MDM2 inhibitors, 2005 J Am Chem Soc 127, 10130-10131.
Fotouhi, et al., Small molecule inhibitors of p53/MDM2 interaction, 2005 Curr Top Med Chem 5, 159-165.

(56) References Cited

OTHER PUBLICATIONS

Francoz, et al., Mdm4 and Mdm2 cooperate to inhibit p53 activity in proliferating and quiescent cells in vivo. Proc Natl Acad Sci U S A 103, 3232-3237 (2006).
Franklin, et al. Glycogen synthase kinase-3 inhibitors reverse deficits in long-term potentiation and cognition in fragile X mice. Biol Psychiatry 75, 198-206 (2014).
Gannon, et al., ATM phosphorylation of Mdm2 Ser394 regulates the amplitude and duration of the DNA damage response in mice. Cancer Cell 21, 668-679 (2012).
Gottlieb, et al., Cross-talk between Akt, p53 and Mdm2: possible implications for the regulation of apoptosis. Oncogene 21, 1299-1303 (2002).
Grasberger et al., Discovery and cocrystal structure of benzodiazepinedione HDM2 antagonists that activate p53 in cells, 2005 J Med Chem 48:909-912.
Gross, et al., Excess Phosphoinositide 3-Kinase Subunit Synthesis and Activity as a Novel Therapeutic Target in Fragile X Syndrome. Journal of Neuroscience 30, 10624-10638 (2010).
Gross, et al. Excess protein synthesis in FXS patient lymphoblastoid cells can be rescued with a p110beta-selective inhibitor. Mol Med 18, 336-345 (2012).
Gross, et al., Selective role of the catalytic PI3K subunit p110beta in impaired higher order cognition in fragile X syndrome. Cell Rep 11, 681-688 (2015).
Guo, et al., Ablation of Fmrp in adult neural stem cells disrupts hippocampus-dependent learning. Nat Med 17, 559-575 (2011).
Guo, et al., Fragile X Proteins FMRP and FXR2P Control Synaptic GluA1 Expression and Neuronal Maturation via Distinct Mechanisms. Cell Rep 11, 1651-1666 (2015).
Guo, et al., Inhibition of GSK3 beta improves hippocampus-dependent learning and rescues neurogenesis in a mouse model of fragile X syndrome, Hum Mol Genet 21, 681-691 (2012).
Guo, et al., Isolation of multipotent neural stem or progenitor cells from both the dentate gyrus and subventricular zone of a single adult mouse. Nat Protoc 7, 2005-2012 (2012).
Guo, et al., RNA-Binding Protein FXR2 Regulates Adult Hippocampal Neurogenesis by Reducing Noggin Expression. Neuron 70, 924-938 (2011).
Hagerman, et al., Treatment of the psychiatric problems associated with fragile X syndrome. Curr Opin Psychiatry 28, 107-112 (2015).
Heulens, et al., Pharmacological treatment of fragile X syndrome with GABAergic drugs in a knockout mouse model. Behav Brain Res 229, 244-249 (2012).
Huang et al., Discovery of highly potent p53-MDM2 antagonists and structural basis for anti-acute myeloid leukemia activities, ACS Chem Biol.2014, 9(3): 802-811.
Issaeva et al., Small molecule RITA binds to p53, blocks p53-HDM-2 interaction and activates p53 function in tumors, 2004 Nat Med 10:1321-1328.
Jessberger, et al., Adult neurogenesis: bridging the gap between mice and humans. Trends Cell Biol 24, 558-563 (2014).
Jin, et al., Understanding the molecular basis of fragile X syndrome, Hum Mol Genet 9: 901-908 (2000).
Jones, et al., Rescue of embryonic lethality in Mdm2-deficient mice by absence of p53. Nature 378, 206-208 (1995).
King, et al., Lithium treatment alleviates impaired cognition in a mouse model of fragile X syndrome. Genes Brain and Behavior 12, 723-731 (2013).
Kunkele, et al., Pharmacological activation of the p53 pathway by nutlin-3 exerts anti-tumoral effects in medulloblastomas. Neuro Oncol 14, 859-869 (2012).
Mayo, et al., A phosphatidylinositol 3-kinase/Akt pathway promotes translocation of Mdm2 from the cytoplasm to the nucleus. Proc Natl Acad Sci U S A 98, 11598-11603 (2001).
Lara, Jr., et al., Phase II Study of the AKT inhibitor MK-2206 plus Erlotinib in Patients with Advanced Non-Small Cell Lung Cancer who Previously Progressed on Erlotinib. Clin Cancer Res, (2015).
Li et al., MDM2 inhibition rescues neurogenic and cognitive deficits in a mouse model of fragile X syndrome, Science Translational Medicine 8(336): 336ra61 (2016).
Li, et al., Coexistence of Quiescent and Active Adult Stem Cells in Mammals. Science 327, 542-545 (2010).
Li, et al., Concise review: Fragile X proteins in stem cell maintenance and differentiation. Stem Cells 32, 1724-1733 (2014).
Liu et al., Epigenetic regulation of miR-184 by MBD1 governs neural stem cell proliferation and differentiation, May 7, 2010;6(5):433-44.
Huang, et al., Discovery of Highly Potent p53-MDM2 Antagonists and Structural Basis for Anti-Acute Myeloid Leukemia Activities, ACS Chem. Biol. 2014, 9, 802-811.
Jewett, et al., The tumor suppressor p53 guides GI uA1 homeostasis through Nedd4-2 during chronic elevation of neuronal activity, Journal of Neurochemistry, 2015, 135, 226-233.

* cited by examiner

FIGS. 22A-22H
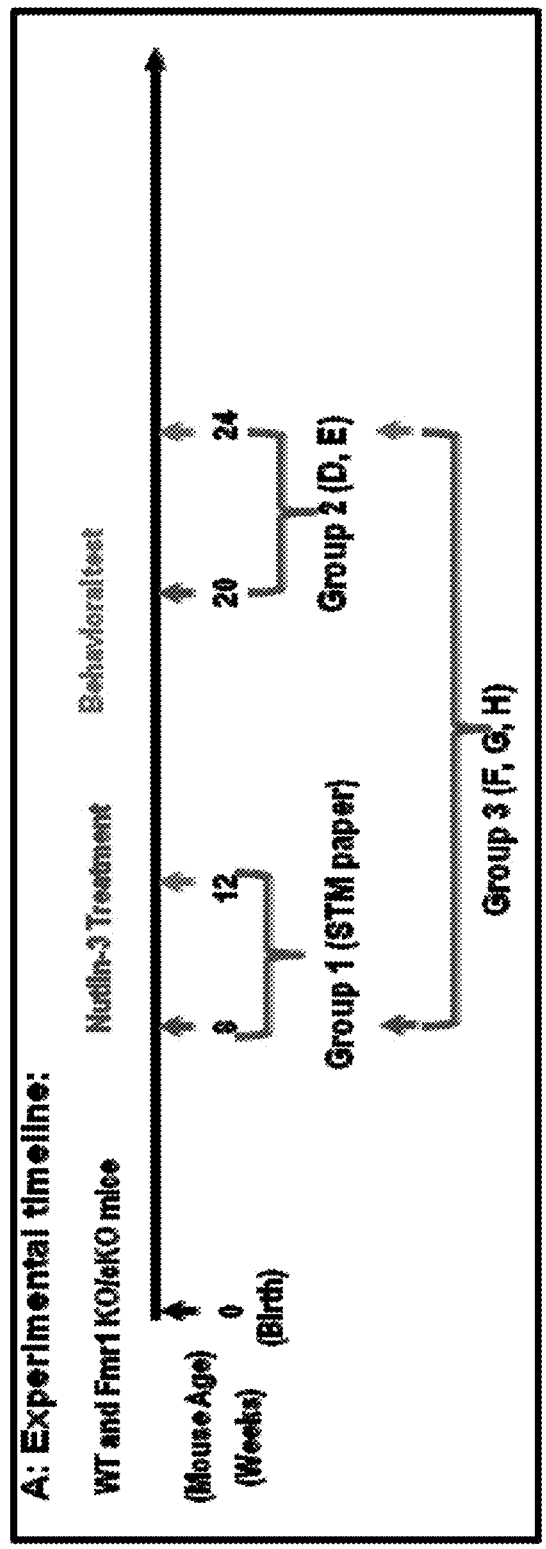
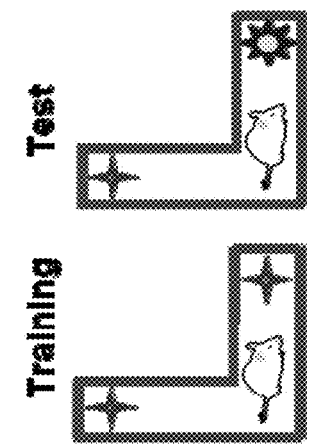
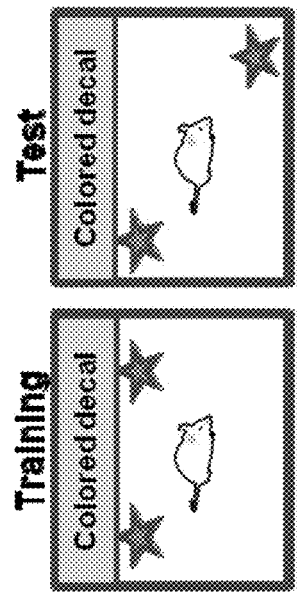

METHODS FOR TREATING COGNITIVE DEFICITS ASSOCIATED WITH FRAGILE X SYNDROME

CROSS-REFERENCE TO RELATED APPLICATIONS

This application is a divisional application of U.S. patent application Ser. No. 15/274,983, filed Sep. 23, 2016, which claims the benefit of U.S. Provisional Application No. 62/222,267, filed Sep. 23, 2015, each of which is incorporated herein by reference as if set forth in its entirety.

STATEMENT REGARDING FEDERALLY SPONSORED RESEARCH

This invention was made with government support under MH078972, MH080434, and HD003352 awarded by the National Institutes of Health. The government has certain rights in the invention.

BACKGROUND

Fragile X Syndrome (FXS) is the most common form of inherited intellectual disability and the biggest single gene contributor to autism, with a frequency of 1 in 4000 males and 1 in 6000 females. Almost all cases of FXS are caused by an expansion of the CGG trinucleotide repeat in the FMR1 (fragile X mental retardation 1) gene, which codes for the RNA-binding protein FMRP (Fragile X mental retardation protein). In these cases, CGG is abnormally repeated from 200 to more than 1,000 times, which makes this region of the gene unstable and little or no FMRP is produced. The loss or shortage of FMRP disrupts normal neuronal function, causing severe learning problems, intellectual disability, and the other features of FXS. The hallmark neurobehavioral symptoms of FXS include hyperactivity, defects in sensory integration, communication difficulties, poor motor coordination, social anxiety and restricted repetitive and stereotyped patterns of behavior. Among the hallmark phenotypes reported in individuals with FXS are deficits in attentional function, inhibitory control, and cognitive flexibility. FXS is also a well-characterized form of autism spectrum disorder. About one-third of males with an FMR1 gene mutation and the characteristic signs of fragile X syndrome also have features of autism spectrum disorder that affect communication and social interaction.

Several neurotransmitters and signaling pathways have been found to mediate FMRP function, including group I metabotropic glutamate receptor type 5 (mGluR5), N-methyl-D-aspartate receptor subunits, $GABA_A$ receptor, mTOR, TSC-2 and GSK3β. These discoveries led to the development of pharmaceuticals for FXS, including lithium (GSK3β attenuation), $GABA_A$ agonists, mGluR5 antagonists, including fenobam, which have been shown to reverse multiple phenotypes in FXS such as audiogenic seizures, open field hyperactivity, and dendritic spine morphology.

FMRP is highly expressed in neurons, and studies show that FMRP regulates neurotransmitters and neuronal signaling molecules. Although many targets for treating FXS have emerged, the clinical failures of two recent large mGluR5-antagonist programs in FXS have forced drug developers to rethink target selection for neurodevelopmental indications. Thus, there is a need to develop new, improved and effective methods to treat fragile X syndrome, autism, and mental retardation.

SUMMARY OF THE INVENTION

In a first aspect, provided herein is a method of treating a cognitive deficit. The method comprises or consists essentially of administering an effective amount of a MDM2-p53 pathway inhibitor to a subject afflicted with a cognitive deficit, whereby administration of the inhibitor improves, enhances, or rescues at least one cognitive deficit in the subject. The MDM2-p53 pathway inhibitor can be selected from the group consisting of Nutlin-3, Nutlin-3a, RG7112, YH239-EE, SAR405838, a cis-imidazole compound, a benzodiazepine, a RITA (reactivation of p53 and induction of tumor cell apoptosis) compound, a spiro-oxindole compound, and a quininol compound. The MDM2-p53 pathway inhibitor can be Nutlin-3. The cognitive deficit can be a memory deficit or learning deficit. The cognitive deficit can be associated with a Fmr1 genetic defect. The Fmr1 genetic defect can comprise a full mutation FXS allele. The Fmr1 genetic defect can comprise a pre-mutation FXS allele. In some cases, the subject has or is suspected of having Fragile X Syndrome (FXS). The cognitive deficit can be associated with aberrant neurogenesis. The administration of the inhibitor can increase neurogenesis in the subject.

These and other features, aspects, and advantages will become better understood upon consideration of the following detailed description, drawings and appended claims.

BRIEF DESCRIPTION OF THE DRAWINGS

This patent application file contains at least one drawing executed in color. Copies of this patent or patent application publication with color drawings will be provided by the Office upon request and payment of the necessary fee.

Ai14 control mice. (O) Comparison of the percentage of activated NSCs among total NSCs in the dentate gyms (n=6 per genotype). Student's t-tests were used for all data. P<0.01, *P<0.001. From A to N, n=5 per genotype. Data are presented as mean±SEM.

FIGS. 2A-2H demonstrate that FMRP regulates MDM2 expression in adult mouse NPCs. (A) Workflow for selecting potential FMRP target genes that may regulate activation of adult NSCs. (B to E) FMRP RNA immunoprecipitation (IP) followed by quantitative real-time PCR analyses for Mdm2 (B), GSK3β (C), Map1b (D), and Gapdh (E, negative control) mRNAs in Fmr1 wildtype (WT) and KO mouse NPCs (n=3). The amount of each mRNA in IP samples was normalized to the amount of mRNA in the input samples. (F and G) Quantification analyses of Mdm2 mRNA (F) and MDM2 protein (G) in wildtype (WT) and Fmr1 KO mouse NPCs (n=3). Gapdh was used as the internal control for qPCR analysis, and GAPDH was used as a loading control for western blot analysis. (H) Mdm2 mRNA stability in Fmr1 wildtype (WT) and KO mouse NPCs treated with Actinomycin D to inhibit transcription. The percentage of Mdm2 mRNA remaining in NPCs was quantified using real-time PCR. Comparisons of the different decay rates were performed by two-way ANOVA (n=3). Half-life of decay was calculated after ln2 transformation. Except for FIG. 2I, Student's t-tests were used for data analyses. Data are presented as mean±SEM. *P<0.05; **P<0.01. n.s., no significant difference.

FIGS. 3A-3M demonstrate that FMRP regulates MDM2 phosphorylation via the AKT pathway. (A) Schematic drawing showing that, in addition to inhibiting Mdm2 mRNA expression, FMRP can also inhibit MDM2 phosphorylation at Ser166/186 through AKT signaling. MK2206 is a selective AKT inhibitor. (B, C, D) Western blot analyses (B) of total MDM2 (C) and phosphorylated MDM2 at Ser166 (p-MDM2) (D) in Fmr1 wildtype (WT) and KO mouse NPCs (n=3). (E and F) Western blot analyses of total and phosphorylated AKT at Ser473 (p-AKT) (n=3). (G and H) Western blot analyses of P53 showing that P53 was decreased in Fmr1 KO mouse NPCs compared with wildtype (WT) NPCs (n=3). GAPDH was used as a loading control. (I, J, K, L, M) Representative western blot image (I) and quantitative analyses of p-AKT (J), p-MDM2 (K), total MDM2 (L), and P53 (M) in Fmr1 KO and wildtype (WT) mouse NPCs treated with MK2206 or vehicle. Total AKT was used as a loading control for p-AKT, and GAPDH was used as a loading control for p-MDM2, MDM2, and P53 (n=3). *P<0.05; P<0.01; *P<0.001; n.s., no significant difference; Student's t-test was used in C—H; one-way ANOVA was used in J-M. Data are presented as mean±SEM.

Figures 4A, 4O:
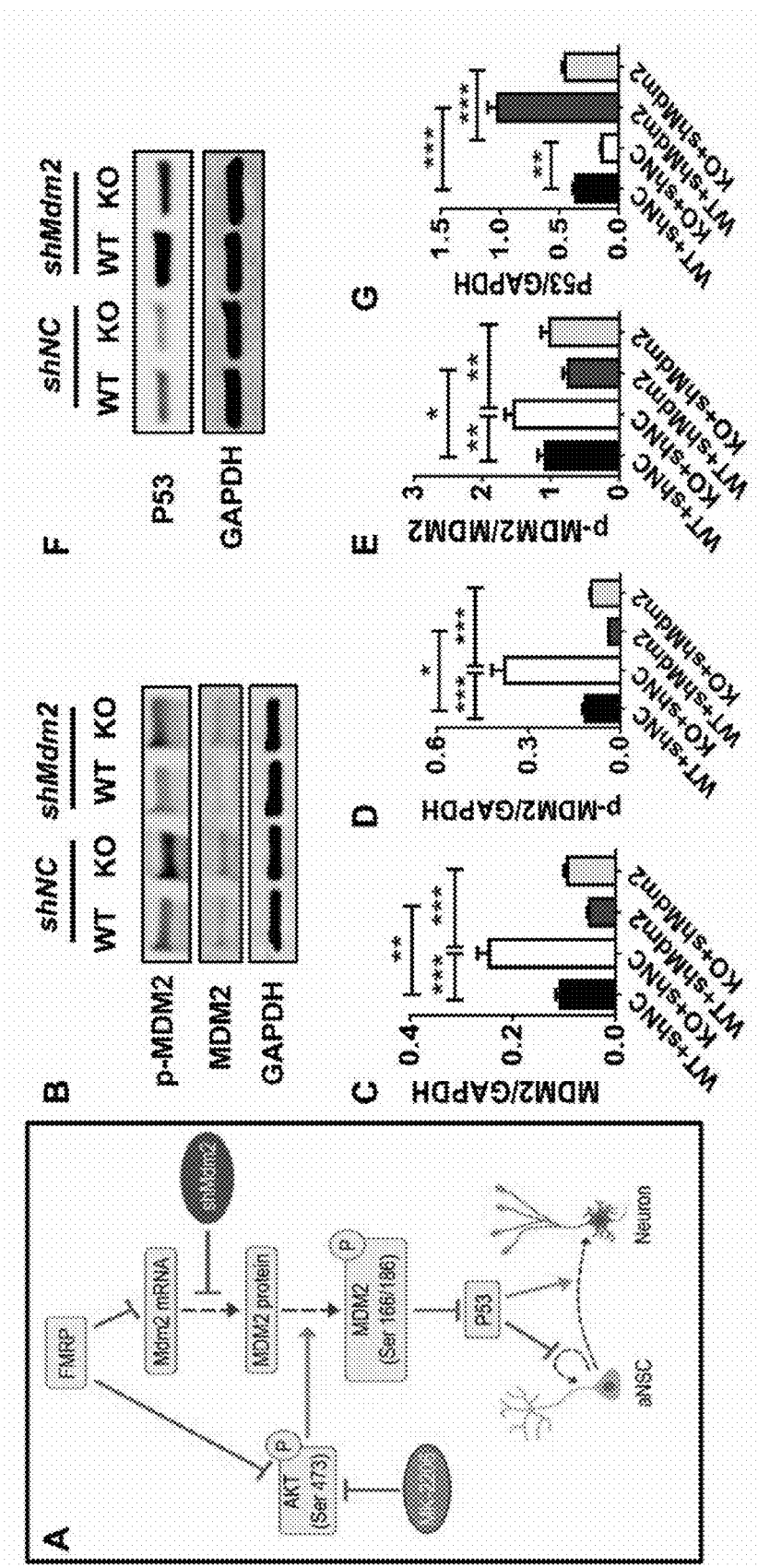
Figures 4A, 4O:
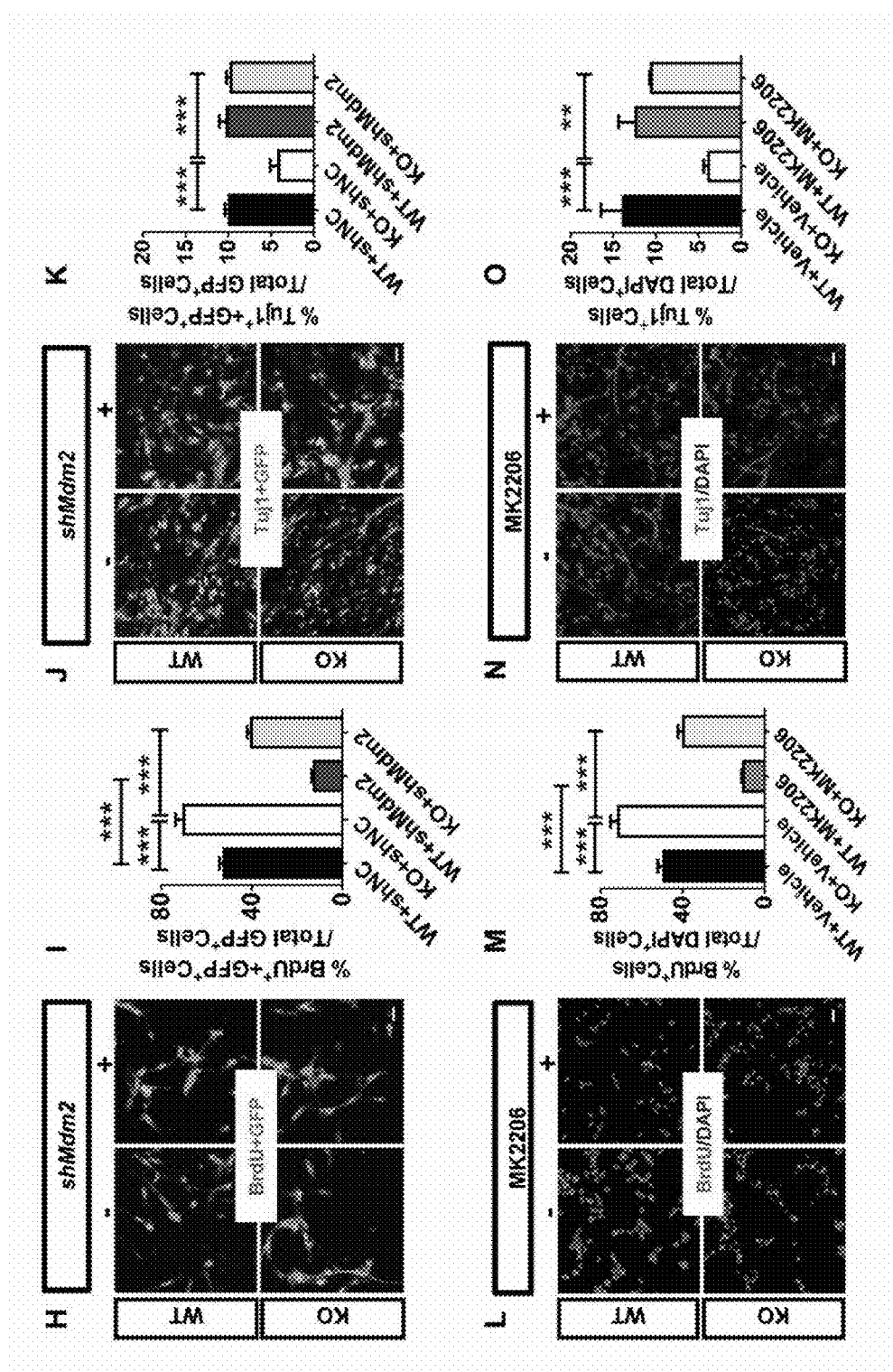

FIGS. 4A-4O demonstrate that MDM2 and p-MDM2 expression directly impact the proliferation and differentiation of mouse NPCs. (A) Schematic model showing that both acute knockdown of MDM2 and treatment with MK-2206 may repress MDM2, relieve P53 repression, and rescue proliferation and differentiation of Fmr1 KO mouse NPCs. (B, C, D, E) Western blot analyses (B) of MDM2 (C) and p-MDM2 (D) in NPCs with acute knockdown of MDM2 using shMdm2 (n=3, normalized to GAPDH or total MDM2). (F and G) Western blot analyses (F) of P53 expression in NPCs with acute knockdown of MDM2 by shMdm2 (G) (n=3). GAPDH was used as a loading control. (H) Representative images showing that both Fmr1 wildtype (WT) and KO mouse NPCs incorporated BrdU (Red) under proliferating conditions, with or without shMdm2 treatment (Green). Scale bars: 20 μm. (I) Quantitative analysis showing that acute knockdown of MDM2 by shMdm2 reduced the proliferation rate of both Fmr1 wildtype (WT) and KO mouse NPCs (n=3). (J and K) Acute knockdown of MDM2 by shMdm2 rescued neuronal differentiation phenotypes of Fmr1 KO NPCs, as assessed using the neuronal marker Tuj1+ (J) (red for Tuj1; green for shMdm2 or shNC viral-infected cells); quantification is in (K). (n=3). (L) Both wildtype (WT) and KO mouse NPCs incorporated BrdU (red) under proliferating conditions. Scale bars: 20 μm. (M) MK-2206 treatment reduced the proliferation rate of both Fmr1 wildtype (WT) and KO NPCs (n=3). (N and O) MK-2206 treatment rescued neuronal differentiation phenotypes of Fmr1 KO NPCs (n=3). One-Way ANOVA was used for all data analyses. *P<0.05; P<0.01; *P<0.001. Data are presented as mean±SEM. Veh, vehicle.

FIGS. 5A-5K demonstrate that Nutlin-3 treatment rescues the proliferation and differentiation of NPCs in vitro. (A) Schematic showing that Nutlin-3 may inhibit the interaction between p-MDM2(Ser166/S186) and P53 relieving the repression of P53 and rescuing the proliferation and neuronal differentiation of NPCs. (B, C, D, E) Western blot analyses of p-MDM2 (B, C) and P53 (D, E) in Fmr1 wildtype (WT) and KO NPCs treated with Nutlin-3, showing that Nutlin3 treatment does not affect P-MDM2 protein levels by inhibiting the activity of p-MDM2 towards downstream target P53. Nutlin-3 had no significant effect on p-MDM2 expression in Fmr1 KO and wildtype NPCs, but specifically rescued P53 expression in Fmr1 KO NPCs without affecting wildtype cells (n=3). GAPDH was used as a loading control in western blot analyses. (F and G) Nutlin-3 treatment rescued the cell proliferation phenotype of Fmr1 KO NPCs, as demonstrated by immunostaining cells using the cell proliferation marker BrdU (F, red Scale bars: 20 μm), followed by quantitative analysis of BrdU+ cells (G) (n=3). (H and I) Nutlin-3 treatment rescued neuronal differentiation phenotypes of Fmr1 KO NPCs, as assessed by a neuronal marker Tuj1+ (red, Scale bars: 20 μm) (H); quantitative analysis in (I), n=3). (J and K) Nutlin-3 treatment specifically rescued astroglial differentiation phenotypes of Fmr1 KO NPCs, as assessed using the astroglial marker GFAP+ (green, Scale bars: 20 μm) (J); quantitative analysis in (K) (n=3). P<0.01; *P<0.001. One-way ANOVA was used for all data analyses. Data are presented as mean±SEM. Veh, vehicle.

FIGS. 6A-6K demonstrate that Nutlin-3 treatment can rescue neurogenesis deficits in Fmr1 KO mice. (A, B, C) Sample confocal images of GFP+p-MDM2+ (A) and GFP+ p-MDM2– (B) cells in the adult mouse dentate gyms and quantitative comparison of the percentage of p-MDM2+ cells among GFP+ cells in Fmr1 KO and wildtype (WT) mice. Quantitation in C; n=3,P<0.01, Student's t-test. Blue, DAPI; green, GFP; red, p-MDM2 (Ser166); Scale bars: 20 μm. (D) Experimental scheme for assessing aNSC activation in Fmr1 wildtype (WT) and KO mice treated with Nutlin-3 or vehicle. (E) Sample confocal images of activated NSCs (GFP+GFAP+MCM2+) in the dentate gyms of adult Fmr1 wildtype/KO-Nestin-GFP mice. Blue, DAPI; green, GFP; red, MCM2, Scale bar: 20 μm. (F) Comparison of the percentage of activated NSCs among total NSCs in the dentate gyms of Fmr1 KO mice and wildtype (WT) mice with or without Nutlin-3 treatment (n=3 per group). (G) Experimental scheme for assessing aNSC differentiation in Fmr1 wildtype (WT) and KO mice treated with Nutlin-3 or vehicle. (H and I) Nutlin-3 treatment rescued neuronal differentiation in Fmr1 KO mice, as assessed by immunostaining with the neuronal marker NeuN (green) and BrdU (red) (H Scale bar: 20 μm) quantification of percentage of neurons among BrdU+ cells (I) (n=3-5 per group). (J and K) Nutlin-3 treatment rescued astroglial differentiation specifically in Fmr1 KO mice, as assessed by an astroglial marker S100β (green) and BrdU (red) (J), Scale bar: 20 μm; quantification of the percentages of astrocytes among BrdU+ cells is in (K), (n=3-5 per group). P<0.01; ****P<0.0001; One-Way ANOVA. Data are presented as mean±SEM. n.s.; no significant difference. The boxes with dotted white lines in A, B, E, H, J indicate regions with higher magnification images provided.

FIGS. 7A-7E demonstrate that Nutlin-3 treatment rescues cognitive functions in Fmr1 KO mice. (A) Experimental scheme for assessing cognitive functions in Fmr1 wildtype (WT) and KO mice treated with Nutlin-3. (B) Schematic of novel location test for assessing spatial learning. (C) Nutlin-3 treatment fully rescued spatial memory deficits in Fmr1 KO mice in the novel location test (n=9-13 mice per group). (D) Schematic of the novel object recognition test. (E) Nutlin-3 treatment fully rescued deficits in the novel object recognition test in Fmr1 KO mice (n=8-14 mice per group), P<0.01; *P<0.001, One-Way ANOVA was used for all data analyses. Data are presented as mean±SEM.

Figures 8A, 8O:
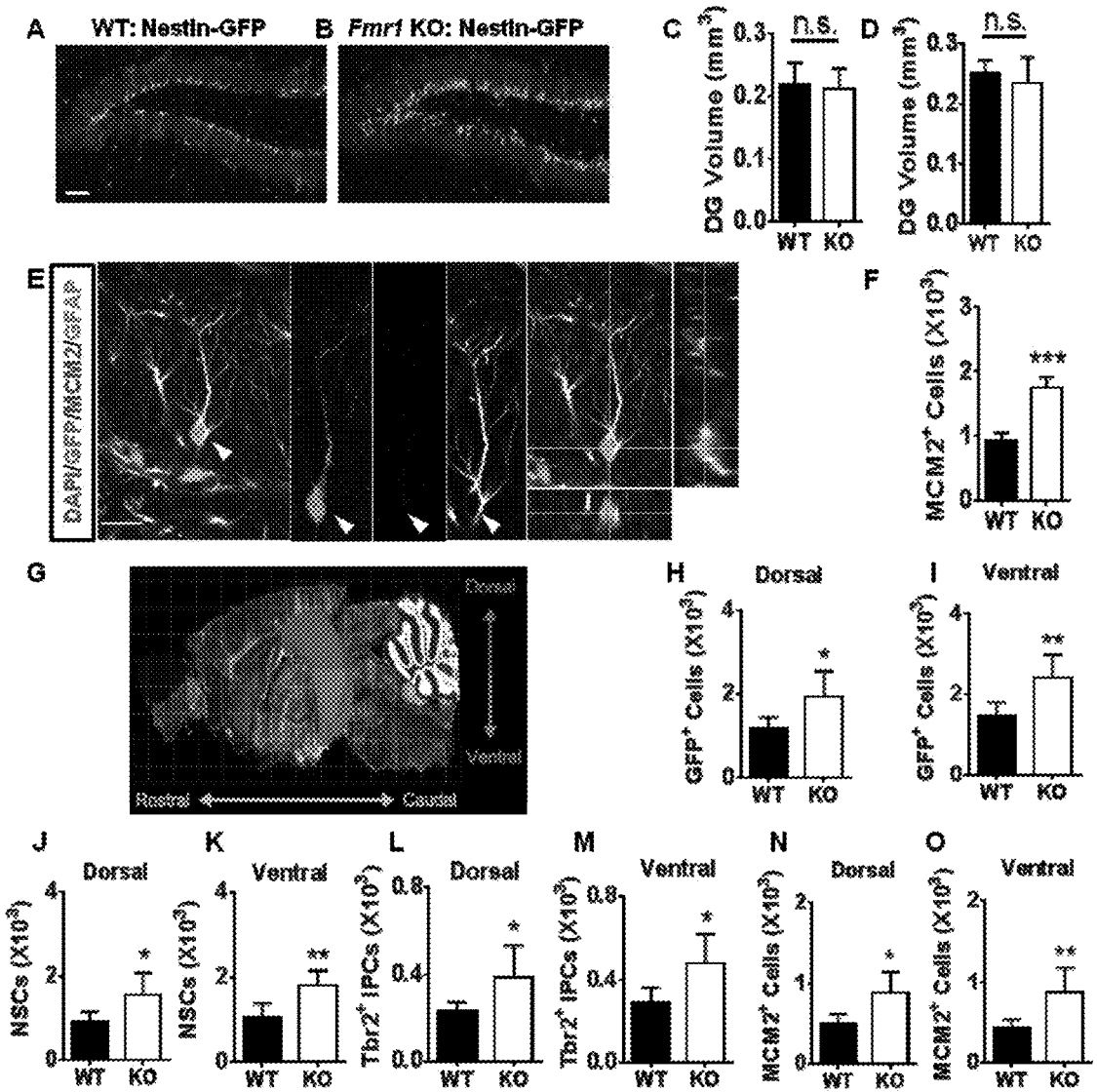

FIGS. 8A-8O demonstrate that FMRP deficiency does not affect dentate gyrus volume but leads to increased number of activated cells in the adult dentate gyrus and increased numbers of total GFP+ cells, NSCs, intermediate progenitor cells (IPCs) in both dorsal and ventral dentate gyrus. (A and B) Sample confocal images showing GFP+ cells in the dentate gyrus of adult wildtype (WT)::Nestin-GFP (A) and Fmr1 KO::Nestin-GFP (B) and mice. Scale bar:100 μm. (C) Quantitative comparison of dentate gyrus volume of wildtype (WT) and Fmr1 KO mice (n=5 per genotype); Student's t-tests. (Note: this is the concise volume measured by optical fractionator). (D) The dentate gyrus volume of wildtype (WT) and Fmr1 KO mice (n=5 per genotype) (Note: this was the volume used for cell quantification for FIG. 1 and Fig. S1 therefore it includes one extra cell layer adjacent to SGZ). (E and F) Sample confocal images (E) and quantitative comparison (F) of MCM2+ cells in the dentate gyrus of wildtype (WT) and Fmr1 KO mice (n=5 per genotype). Scale bar: 20 (G) Schematic illustration of the dorsal (blue) and ventral (pink) hippocampus (Image obtained from Allen Brain Atlas). (H to O) Cell quantification was done in dorsal and ventral hippocampus for total GFP+ cells (H, I), NSCs (J,K), IPCs (L,M), and MCM2+ cells (N,O). (n=5 per genotype). *P<0.05; P<0.01 *P<0.001). Student's t-tests. n.s., no significant difference.

Figures 9A, 9B, 9C:
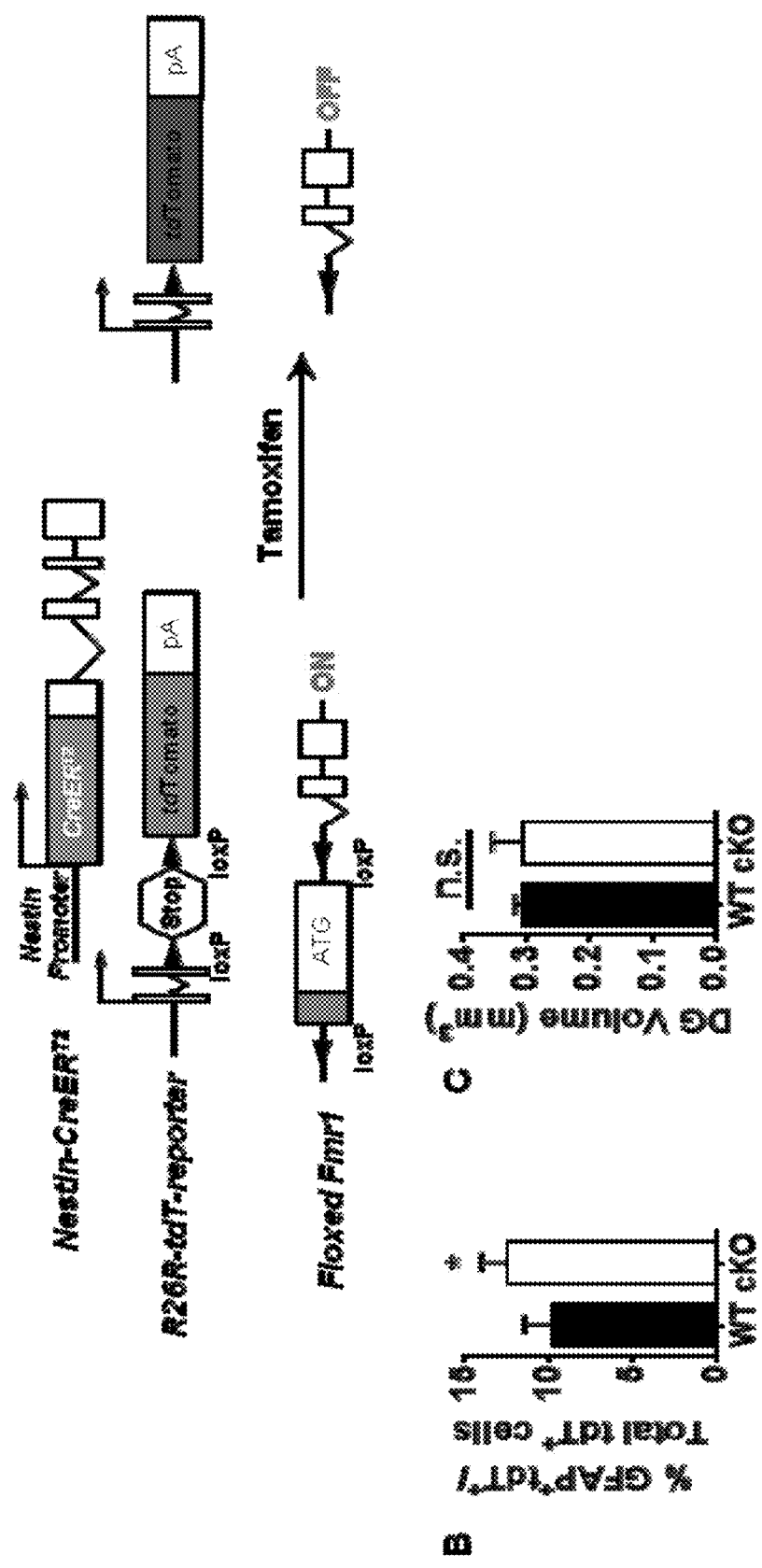
Figures 10A, 10B, 10C, 10D, 10E, 10F, 10G, 10H:
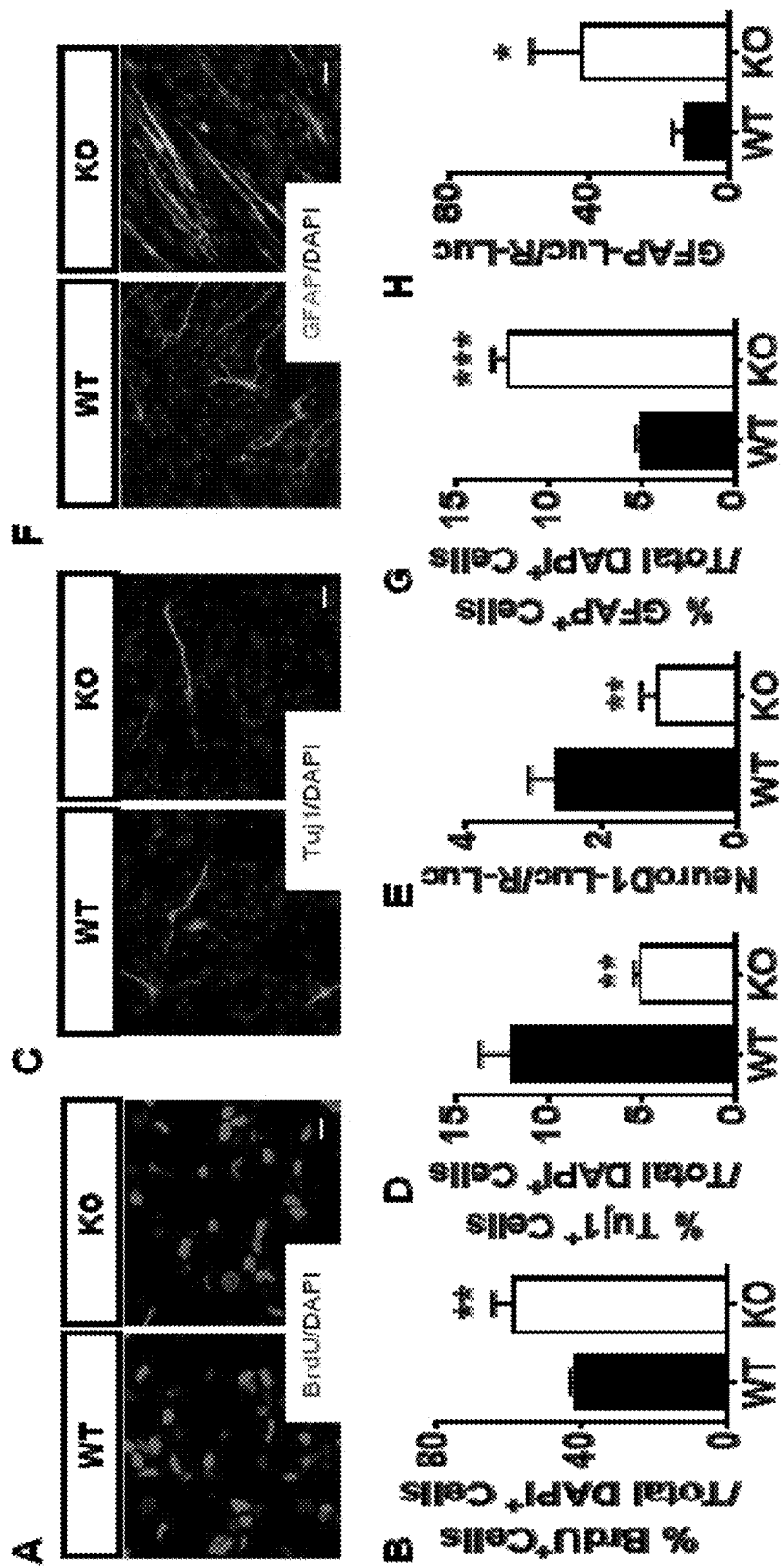
Figures 11A, 11B, 11C, 11D, 11E, 11F, 11G, 11H, 11I, 11J, 11K, 11L, 11M:
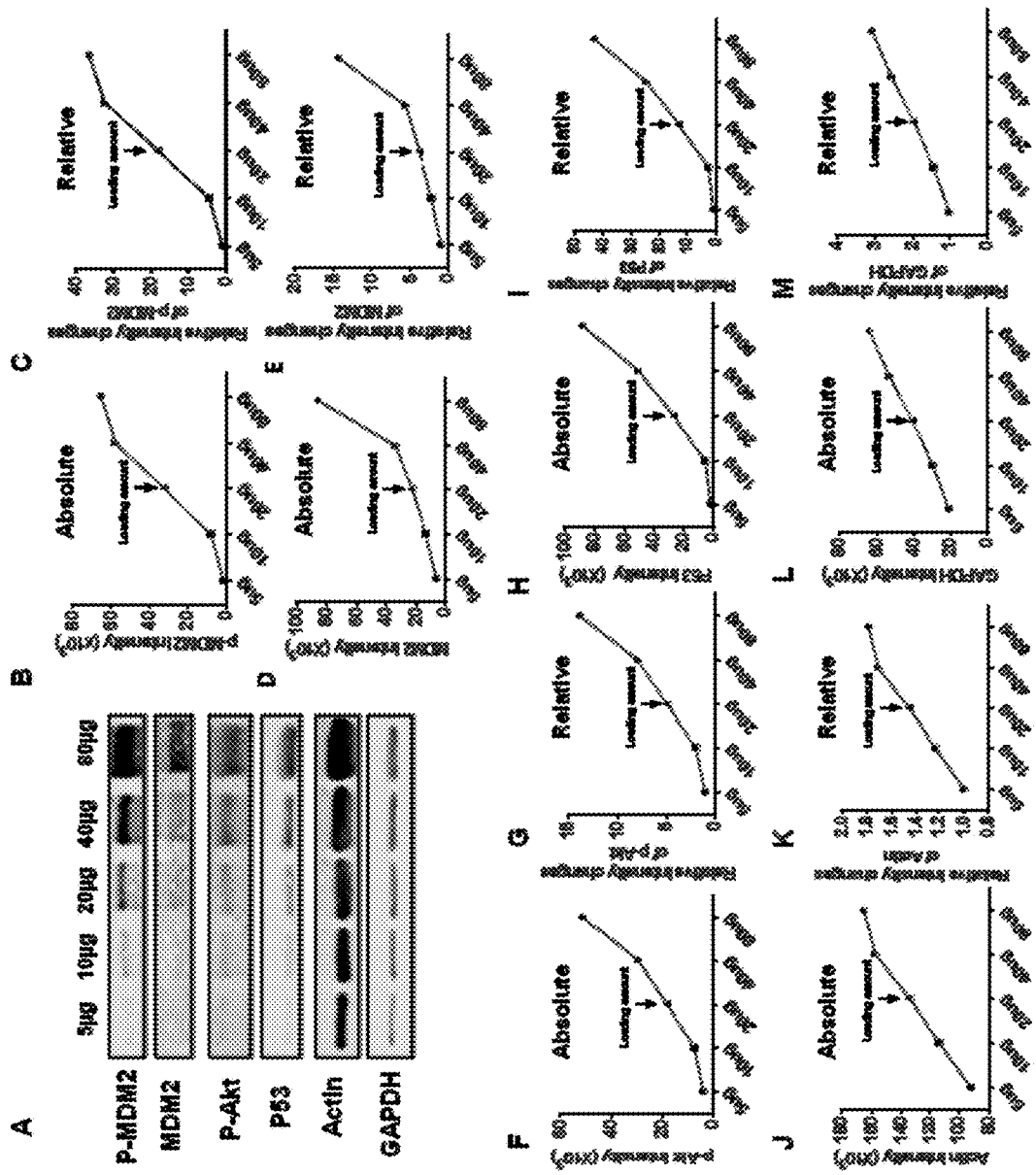

FIGS. 9A-9C demonstrate that conditional deletion of FMRP leads to increased NSC numbers in the adult dentate gyrus without affecting overall dentate gyrus volume. (A) An inducible FMRP conditional knockout mouse line was created by crossing Nestin-CreER$^{T2}$ mice, ROSA26-STOP-tdTomato (Ai14) mice and Fmr1 foxed (Fmr1 cKO) mice. Administration of tamoxifen to adult mice results in the removal of the first exon of the mouse Fmr1 gene and the "Stop" codon before tdTomato (tdT) in Nestin-expressing cells and their subsequent progenies. (B) Comparison of the percentage of NSCs (tdT+GFAP+) among the total tdT+ cells in the dentate gyrus of cKO;Cre;Ai14 mice and Cre;Ai14 control mice (n=5 per genotype;*P<0.05). Student's t-tests. (C) Quantitative comparison of dentate gyrus volume of cKO;Cre;Ai14 mice and Cre; Ai14 control mice (n=5 per genotype). n.s., no significant difference. Student's t-tests. Data are presented as mean±SEM.

FIGS. 10A-10H demonstrate that adult NPCs derived from Fmr1 KO mice exhibit increased proliferation, reduced neuronal differentiation, but increased astroglial differentiation. (A) Both wildtype (WT) and Fmr1 KO NPCs incorporate the thymidine analog, BrdU, under proliferating conditions (BrdU, red; DAPI, blue); Scale bars: 20 μm. (B) Quantitative analysis showing that Fmr1 KO NPCs had a higher percentage of BrdU+ cells compared to wildtype (WT) NPCs (n=3). P<0.01; Student's t-tests. (C and D) Fmr1 KO NPCs differentiated into fewer neurons compared to wildtype (WT) NPCs as assessed by a Neuronal marker Tuj1+(C, Red) followed by quantitative analysis (D. n=3); P<0.01; Student's t-tests. Scale bars: 20 μm. (E) Fmr1 KO NPCs differentiated into fewer neurons compared to wildtype (WT) NPCs as demonstrated by transfected NeuroD1 Promoter activity. A co-transfected Renilla luciferase (R-Luc) plasmid was used as a transfection control (n=3). P<0.01; Student's t-tests. (F and G) Fmr1 KO NPCs differentiated into more GFAP+ astrocytes compared to wildtype (WT) NPCs as assessed by an astroglial marker GFAP+ (F, Green) followed by quantitative analysis (G. n=3) *P<0.001; Student's t-tests. (H) Fmr1 KO NPCs differentiated into more GFAP+ astrocytes compared to wildtype (WT) NPCs as demonstrated by transfected GFAP promoter activity. A co-transfected Renilla luciferase (R-Luc) plasmid was used as a transfection control (n=3). *P<0.05; Student's t-tests. Data are presented as mean±SEM.

FIGS. 11A-11M present an assessment of optimal loading amount for protein quantification using Western blotting. (A) Representative western blot images. Total protein lysate of NPCs were loaded at different amount (from 5 μg to 80 μg) into each well of SDS-PAGE gels. The proteins of interest in this manuscript were detected by indicated antibodies. (B and C) The absolute and relative pixel intensities of the p-MDM2. (D and E) The absolute and relative pixel intensities of MDM2. (F and G) The absolute and relative pixel intensities of the p-Akt. (H and I) The absolute and relative pixel intensities of the P53. (J and K) The absolute and relative pixel intensities of β-Actin. (L and M) The absolute and relative pixel intensities of the GAPDH. The arrow and the "Loading amount" indicate the amount of total protein lysate (20 μg) used for Figures in this manuscript. Absolute intensity: The pixel intensity of the band quantified using Image-J without normalization. Relative intensity: the pixel intensities were normalized to the intensity of the band with the lowest amount of loaded protein (5 μg).

Figures 12A, 12B, 12C:
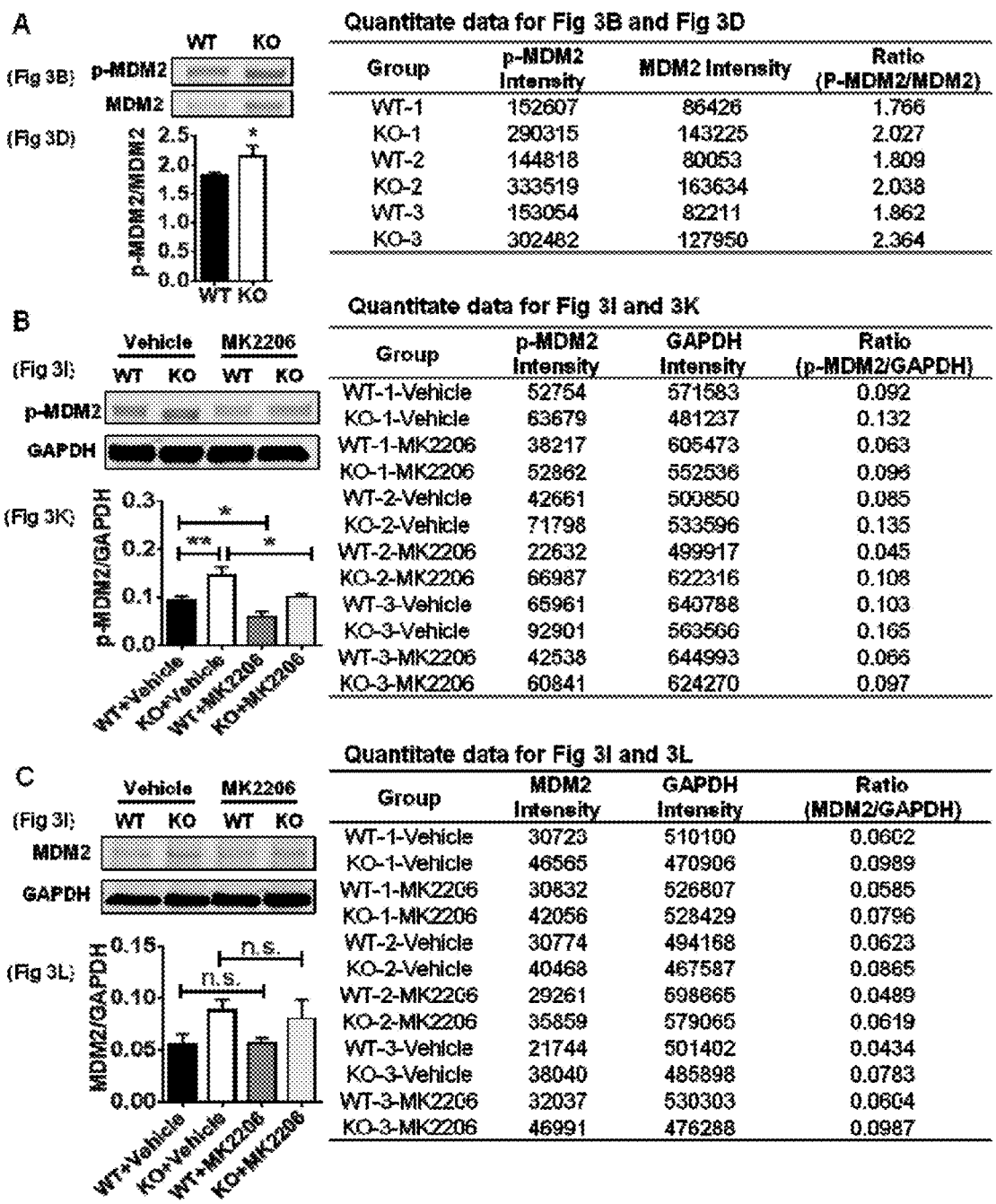

FIGS. 12A-12C show quantitative data for p-MDM2 assessment using Western blot analysis. (A) Quantitative data for FIGS. 3B and 3D. (B) Quantitative data for FIGS. 3I and 3K. (C) Quantitative data for FIGS. 3I and 3L.

FIGS. 13A-13E present Mdm2 mRNA stability analysis in wildtype and Fmr1 KO NPCs. (A) Mdm2 exhibited fast decay in both wildtype (WT) and Fmr1 KO NPCs treated with Actinomycin D to inhibit transcription. (B) Mdm2 stability normalized to another internal control Ywhaz. (C) Mdm2 mRNA expression in Actinomycin D-treated cells normalized to time 0, without normalizing to any internal controls. (D) Gapdh mRNA expression normalized to time 0 only. (E) Ywhaz mRNA expression normalized to time 0 only. The percentage of mRNA remained in NPCs was quantified using real-time PCR at the indicated time point. Comparisons of the different decay rates were performed by Two-Way ANOVA; (n=3; ***P<0.001). Data are presented as mean±SEM.

FIGS. 14A-14F demonstrate that Fmr1 KO NPCs do not exhibit increased cell death. (A to C) Quantitative analysis of apoptosis in wildtype (WT) and Fmr1 KO NPCs by using Annexin V-FITC and PI staining followed by flow cytometry. Representative scatter plots (A) and quantification of Annexin V+PI− early apoptotic cells (B) and both early (Annexin V+PI−) and late (Annexin V+PI+) and apoptotic cells (C). (I) Late apoptotic cells; (II) early apoptotic cells; (III) intact cells; (IV) necrotic cells. n=3; n.s., no significant difference. Student's t-tests. Data are presented as mean±SEM. (D and E). Sample images and quantitative analysis of cell death in wildtype (WT) and Fmr1 KO NPCs treated with Nutlin-3 or vehicle. Cell were incubated with both propidium iodide (PI) that could enter only dead cells and Hoechst43332 that could enter all cells. n=6; Scale bar: 50 μm; n.s., no significant difference. Student's t-tests. Data are presented as mean±SEM. (F). CellTiter-Glo® Luminescent Cell Viability Assay of wildtype (WT) and Fmr1 KO NPCs treated with Nutlin-3 or vehicle. n=3; n.s., no significant difference. Student's t-tests. Data are presented as mean±SEM.

FIGS. 15A-15E demonstrate that both acute knockdown of MDM2 and treatment with MK-2206 rescue astroglial differentiation of Fmr1 KO NPCs. (A) Lentivirus expressing shRNA against Mdm2 (Lenti-shMdm2) effectively knockdown endogenous Mdm2 mRNA. Mdm2 mRNA expression in wildtype (WT) and Fmr1 KO NPCs infected with Lenti-shMdm2 or control Lenti-shNC were assessed using real-time PCR (n=3). $P<0.01$; One-Way ANOVA. (B and C) Acute knockdown of Mdm2 using Lenti-shMdm2 rescued astroglial differentiation phenotypes of Fmr1 KO NPCs as assessed by an astroglial marker GFAP+ (B, Red for astrocytes; Green for shMdm2 or shNC viral infected cells) followed by quantitative analysis (C, percentage of GFAP+GFP+/GFP+ cells). (n=3); $P<0.01$; *$P<0.001$; One-Way ANOVA; Scale bars: 20 m. (D and E) Inhibition of AKT using MK-2206 treatment rescued astroglial differentiation phenotypes of Fmr1 KO NPCs as assessed by an astroglial marker GFAP+ (D, Green) followed by quantitative analysis (E, n=3); $P<0.01$; ***$P<0.001$; One-Way ANOVA; Scale bars: 20 m. Data are presented as mean±SEM.

FIGS. 16A-16F show an inverse correlation of FMRP and p-MDM2 expression in Fmr1$^{+/-}$::Nestin-GFP female brains. (A) Confocal image of Fmr1$^{+/-}$::Nestin-GFP female brain section stained with anti-FMRP (Gray) and anti-p-MDM2 antibody (Red). Due to X chromosome inactivation, half of the Nestin-GFP+ cells should express FMRP whereas the other half should not. Scale Bar:20 μm (B, C) Two GFP+ cells used in quantitative fluorescent analysis shown in E and F. Scale Bar:20 μm (D) Baseline intensity of FMRP signal. (E) The cell with low (near baseline) FMRP signal (gray line) had high expression of p-MDM2 (red line). (F) The cell with high FMRP signal (gray line) had low expression of p-MDM2 (red line).

FIGS. 17A-17D demonstrate that selective deletion of FMRP from Nestin-positive NSCs and their progeny resulted in cognitive deficits, without affecting locomotor activities. (A) Experimental scheme for assessing cognitive function in Fmr1 cKO::Cre::Ai14 mice and Cre::Ai14 control mice. (B) Fmr1 cKO::Cre::Ai14 mice exhibited impaired cognition compared with Cre::Ai14 control mice as determined by the Novel Location Test (NLT). Data are presented as Discrimination Index between novel and familiar locations of the objects. (n=9-12 mice per genotype). *$P<0.05$; Student's t-tests. (C and D) Locomoter activity analyses showed no significant difference between Fmr1 cKO::Cre::Ai14 mice and Cre::Ai14 control mice in either total movement distances (C) or the ratio of center over periphery entry (D) (n=16-21 mice per genotype). n.s., no significant difference. Student's t-tests. Data are presented as mean±SEM.

FIGS. 18A-18D demonstrate that Nutlin-3 treatment does not affect general health and activities of mice. (A) Experimental scheme for assessing cognitive function in wildtype (WT) and Fmr1 KO mice treated with Nutlin-3 or Vehicle (B) Nutlin-3 treatment did not affect body weight of wildtype (WT) and Fmr1 KO mice (n=10-16 mice per group). n.s., no significant difference. One-Way ANOVA. (C-D) Nutlin-3 treatment did not impact locomotor activities including total movement distances (C) and the ratio of center over periphery entry (D) (n=10-16 mice per group). n.s., no significant difference. One-Way ANOVA. Data are presented as mean±SEM.

FIGS. 19A-19L demonstrate increased MDM2/Mdm2 mRNA and p-MDM2 protein expression in the hippocampal and cortical tissues from Fmr1 KO mice and postmortem brains of fragile X syndrome patients. (A and D) Real time qPCR analyses of Mdm2 mRNA expression in the hippocampus (A) and Cortex (D) of wildtype (WT) and Fmr1 KO mice. Gapdh was used as internal control for qPCR analysis. (n=4); *$P<0.001$; Student's t-tests. (B, C, E and F) Western blot analyses of phosphorylated MDM2 at Ser166 (p-MDM2) in the hippocampus (B, C) and cortex (E, F) of wildtype (WT) and Fmr1 KO mice. GAPDH was used as a loading control in western blot analysis. (n=4); *$P<0.001$; Student's t-tests. Data are presented as mean±SEM. (G, J) Real Time qPCR analyses of MDM2 mRNA expression in the hippocampus (G) and cortex (J) of two FXS patients and two matched control individuals (CTL). Gapdh was used as internal control for qPCR analysis. (H, I, K and L) Western blot analyses of p-MDM2 in the hippocampus (H, I) and cortex (K, L) of FXS patients and matched control individuals (CTL). GAPDH was used as a loading control in western blot analysis. Data are presented as mean±SEM.

Figure 20:
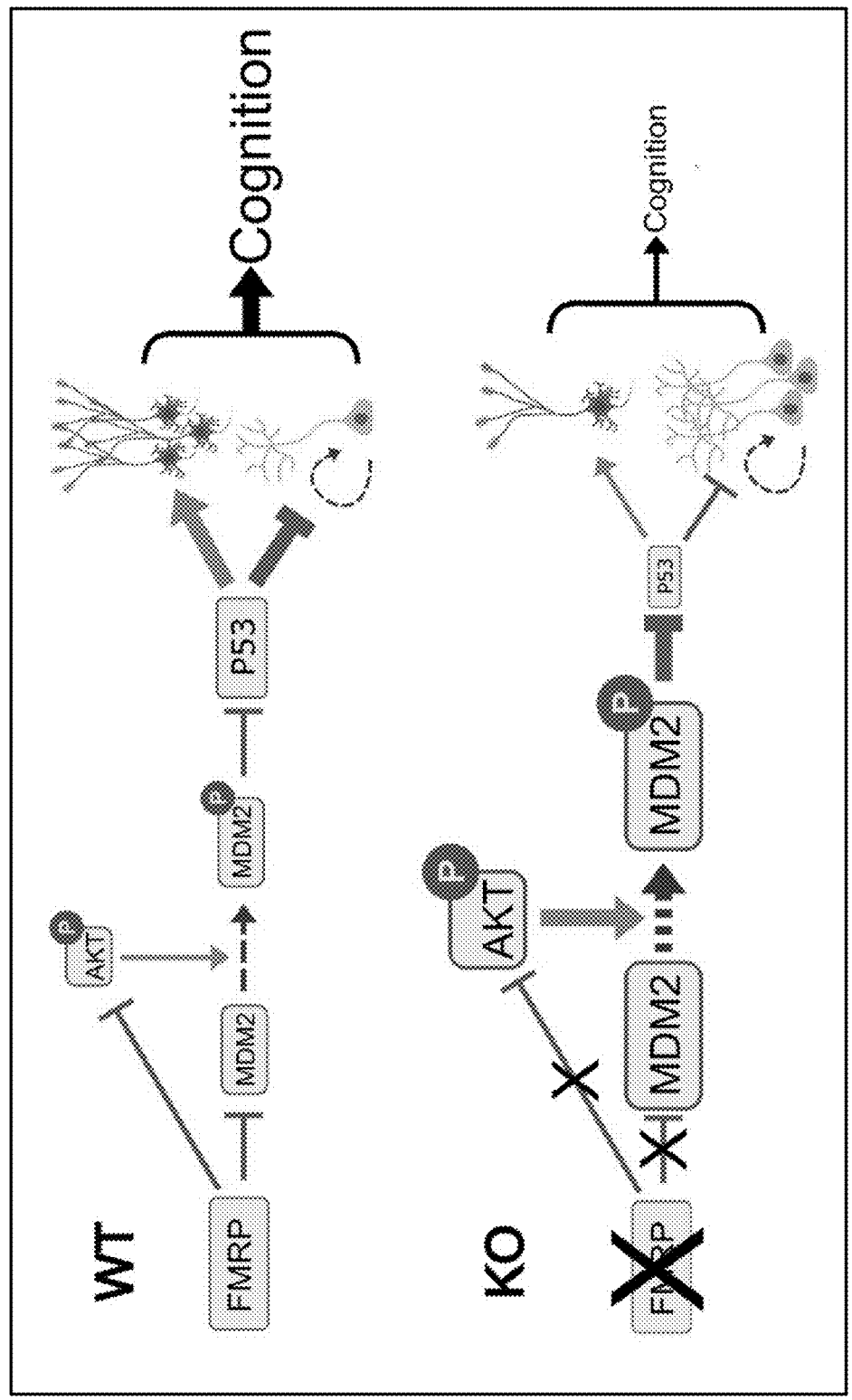
Figures 21A, 21B, 21C, 21D:
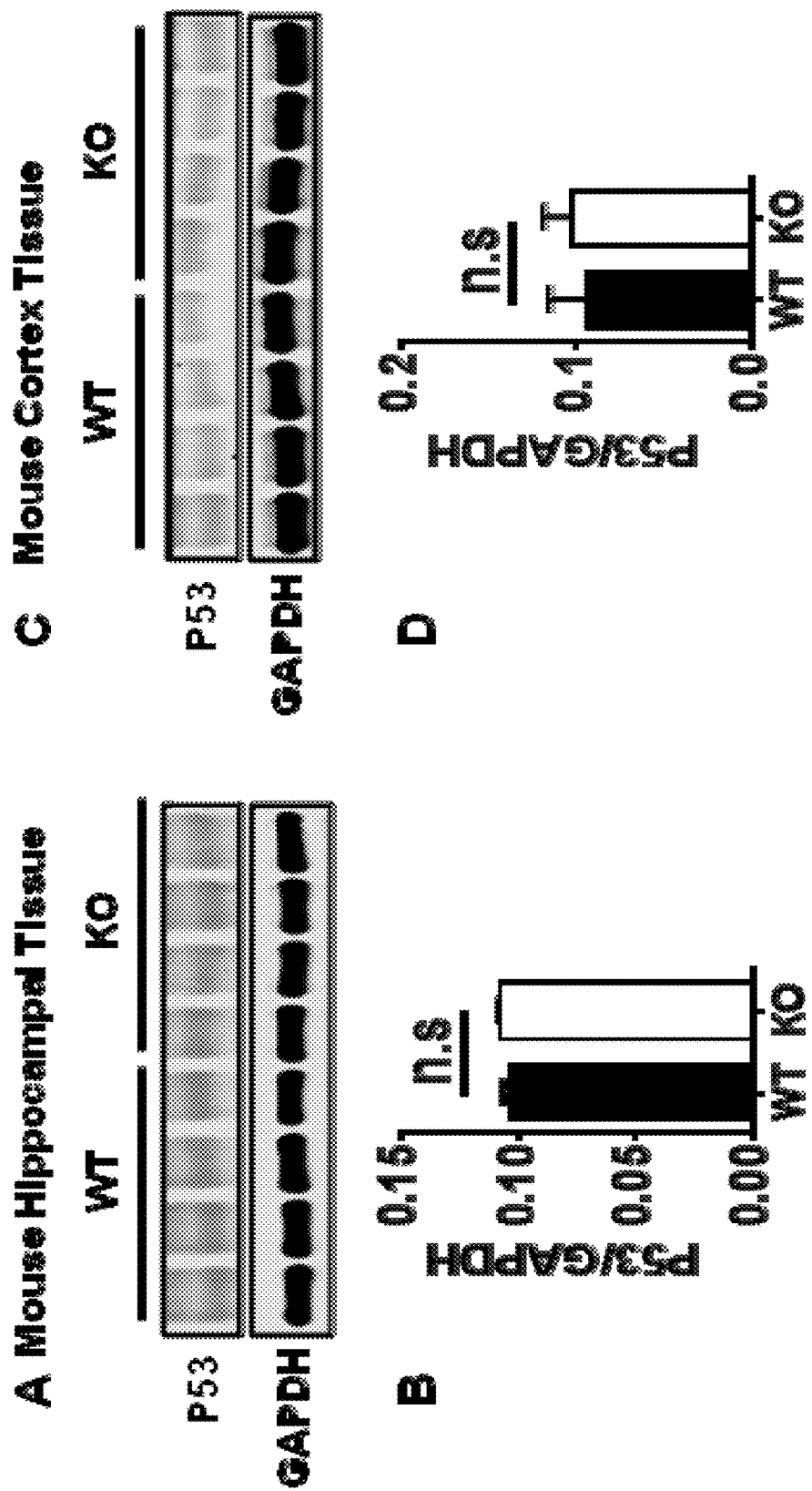
Figures 22A, 22B, 22C, 22D, 22E, 22F, 22G, 22H:
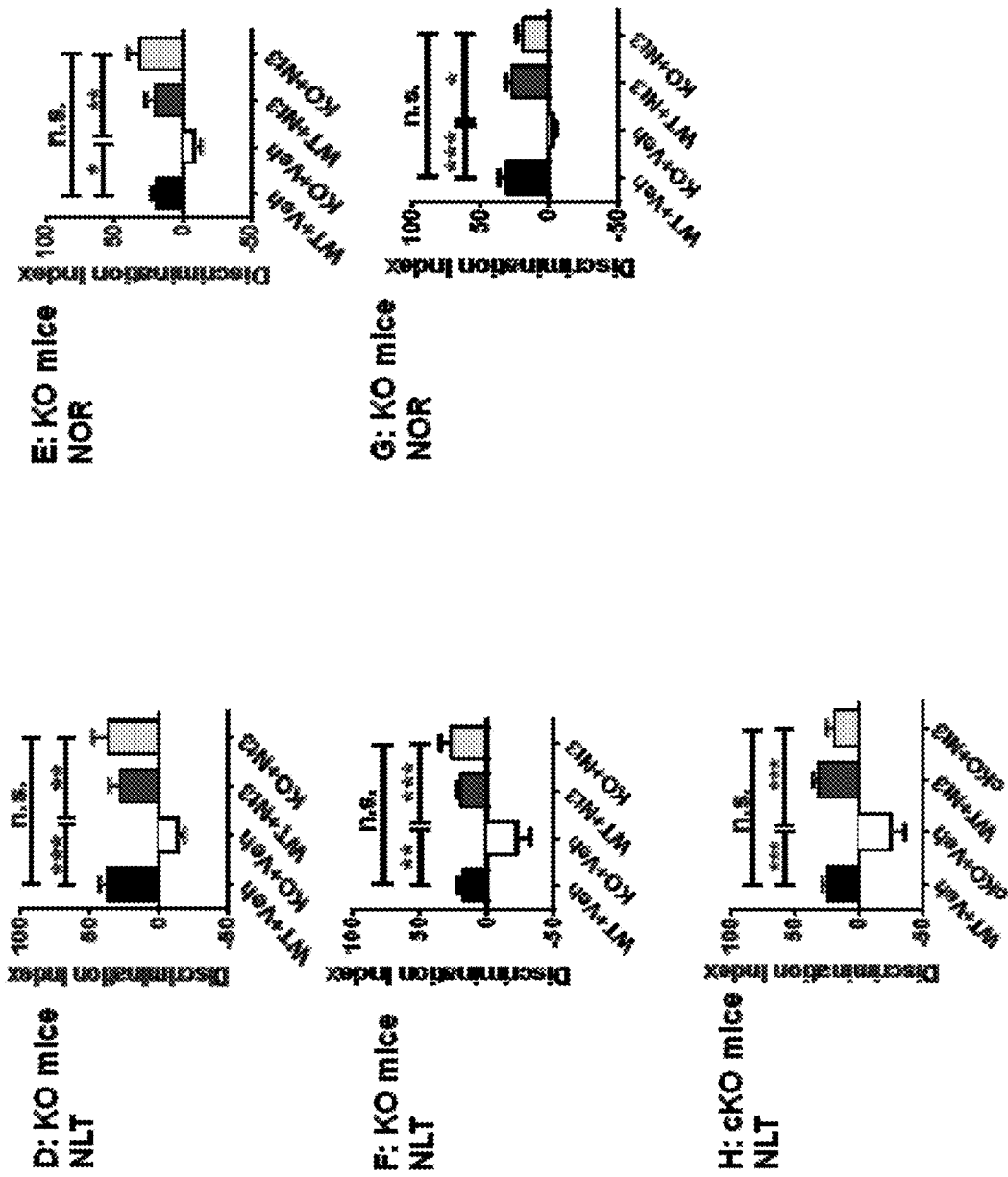

FIG. 20 presents models for FMRP regulation of the MDM2 and P53 pathway, which impacts adult neurogenesis and cognition.

FIGS. 21A-21D demonstrate that P53 protein expression was not significantly changed in the hippocampal and cortical tissues from Fmr1 KO mice. (A and B) Mouse hippocampal tissues. (C and D) Mouse Cortical tissues. GAPDH was used as a loading control in western blot analysis. (n=4); ***$P<0.001$; Student's t-tests. Data are presented as mean±SEM.

FIGS. 22A-22H demonstrate that Nutlin-3 treatment can have long lasting effects and is effective for multiple ages. (A) Experimental scheme for assessing cognitive functions in WT and Fmr1 knockout (KO) mice and Fmr1 conditional knockout mice (cKO) treated with Nutlin-3 at the different time points. Group 1 refers to refers to Nutlin-3 treatment of young adult (8-weeks old) mice and behavioral testing of these mice at 12 weeks of age. Group 2 refers to Nutlin-3 treatment of "middle aged" (20 weeks old) mice rescues cognitive functions of Fmr1 knockout (KO) mice. Group 3 refers to Nutlin-3 treatment of young adult (8-weeks old) mice (including Fmr1 knockout (KO) mice and Fmr1 conditional knockout (cKO) mice (Fmr1 gene deleted in only adult-born neural stem cells and their progeny)) assayed for long-termed effects at 24 weeks old. (B) Schematics of novel location test (NTL) for assessing spatial learning. (C) Schematics of the novel object recognition (NOR) test. (D) Nutlin-3 treatment fully rescued spatial memory deficits in 24-weeks-old Fmr1 KO mice in the NTL (n=8 to 13 mice per group). (E) Nutlin-3 treatment fully rescued cognitive deficits in 24-weeks-old Fmr1 KO mice in the NOR test (n=8 to 14 mice per group). (F) Initial Nutlin-3 treatment had long-term effects to fully rescue spatial memory deficits in 24-weeks-old Fmr1 KO mice in the NTL (n=9 to 12 mice per group). (G) Initial Nutlin-3 treatment had long-term effects to fully rescue cognitive deficits in 24-weeks-old Fmr1 KO mice in the NOR test (n=9 to 14 mice per group). (H) Initial Nutlin-3 treatment had long-term effects to fully rescue spatial memory deficits in 24-weeks-old Fmr1 conditional KO mice in the NTL (n=8 to 11 mice per group).

Figure 23A:
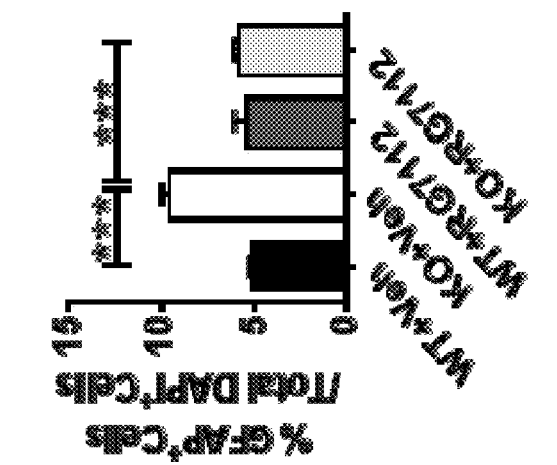
Figure 23B:
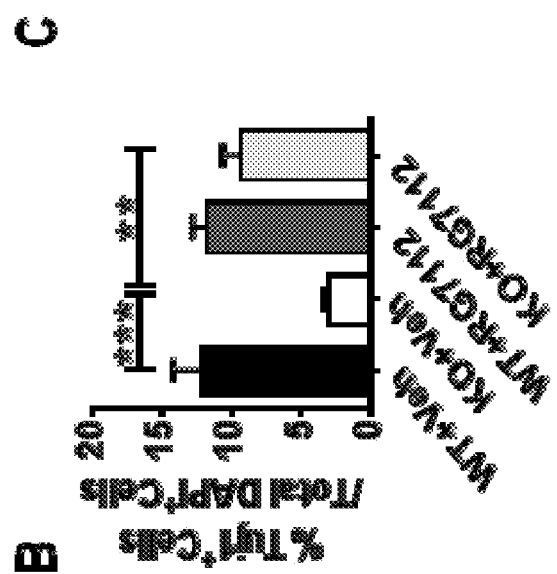
Figure 23C:
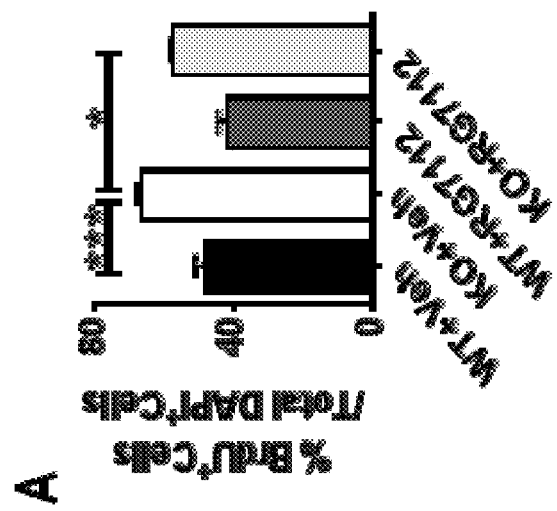

FIGS. 23A-23C demonstrate that RG7112 treatment rescues the proliferation and differentiation of FMRP-deficient NPCs in vitro. (A) RG7112 treatment (1 µM) rescued the cell proliferation phenotype of Fmr1 KO NPCs, as demonstrated by immunostaining cells using the cell proliferation marker BrdU followed by quantitative analysis (n=3). *$P<0.05$; *$P<0.001$ (B) RG7112 treatment (1 µM) rescued neuronal differentiation phenotypes of Fmr1 KO NPCs, as assessed by a neuronal marker Tuj1 followed by quantitative analysis (n=3). $P<0.01$; *$P<0.001$ (C) RG7112 treatment (1 µM) rescued astroglial differentiation phenotypes of Fmr1 KO NPCs, as assessed by an astroglial marker GFAP followed by quantitative analysis (n=3). *$P<0.001$.

Figure 24:
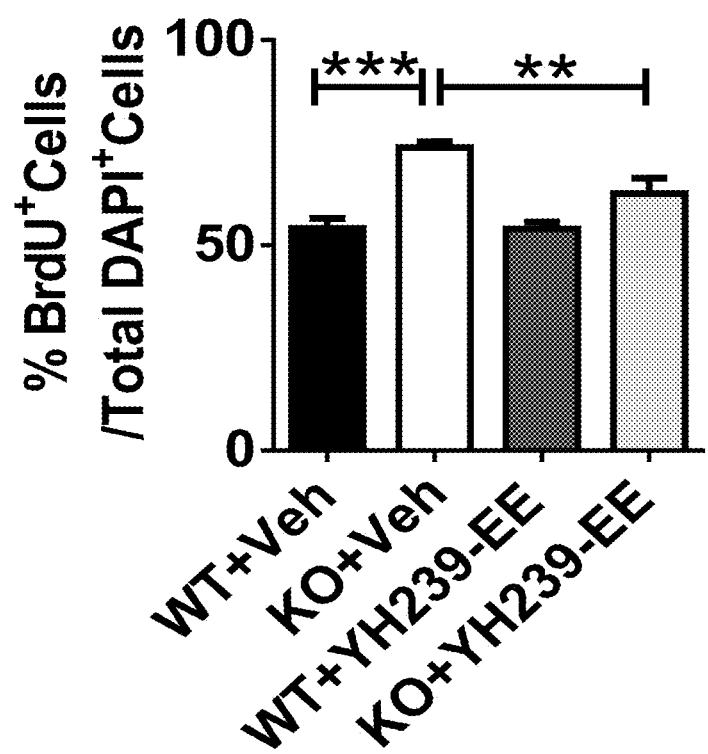

FIG. 24 demonstrates that YH239-EE treatment rescues proliferation of FMRP-deficient NPCs in vitro. YH239-EE treatment (4 µM) rescued the cell proliferation phenotype of Fmr1 KO NPCs, as demonstrated by immunostaining cells using the cell proliferation marker BrdU followed by quantitative analysis (n=3). $P<0.01$; *$P<0.001$.

DETAILED DESCRIPTION OF THE INVENTION

Definitions

In the specification and in the claims, the terms "including" and "comprising" are open-ended terms and should be interpreted to mean "including, but not limited to. . . . " These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

The terms "including", "such as", "for example" and the like are intended to refer to exemplary embodiments and not to limit the scope of the present disclosure.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art.

Methods of the Invention

The methods provided herein are based, at least in part, on the discovery that the interruption of the interaction of MDM2 and p53 inhibits neural stem cell (NSC) proliferation and rescues the cognitive deficits in a FXS mouse model. Treatment with a MDM2-p53 pathway inhibitor normalizes aberrant hippocampal neurogenesis, normalizes aberrant neurogenesis and NSC proliferation in vitro and in mouse models of FXS. These data also suggest that MDM2-p53 pathway inhibitors are useful for treating the cognitive deficits in FXS.

Adult neurogenesis has been explored because of its potential to influence the information processing associated with cognitive outcomes. Impaired adult neurogenesis is implicated in both neuropsychiatric disorders, such as depression and schizophrenia, and neurodegenerative diseases, such as Alzheimer's and Huntington's disease. Interventions aimed at regulating adult neurogenesis are thus being evaluated as potential therapeutic strategies. In many adult organs, both quiescent and activated (actively dividing) stem cells coexist, and the regulation of stem cell quiescence and activation plays an essential role in tissue maintenance, regeneration, function, plasticity, aging, and disease. In the adult hippocampus, quiescent NSCs dynamically integrate both extrinsic and intrinsic signals to either maintain their dormant state, or to become activated and give rise to intermediate progenitor cells (IPCs), which subsequently differentiate into postmitotic dentate gyms (DG) granule neurons or astrocytes. Although it was previously known that FMRP deficiency leads to increased proliferation of NSCs, the involvement of the p53-MDM2 interaction in Fragile X syndrome or FXS-associated cognitive deficits had not been demonstrated.

Fragile X syndrome is a prevalent form of inherited mental retardation and is characterized by developmental delay, hyperactivity, attention deficit disorder, and behaviors associated with autism spectrum disorders (Jin, P., et al., *Hum Mol Genet* 9: 901-908 (2000)). Fragile X syndrome, as implied by its name, is associated with a fragile site expressed as an isochromatid gap in the metaphase chromosome at map position Xq 27.3. Fragile X syndrome is a genetic disorder caused by a mutation in the 5'-untranslated region of the fragile X mental retardation 1 (FMR1) gene, located on the X chromosome. The mutation that causes fragile X syndrome is a associated with a CGG repeat in the fragile X mental retardation gene FMR-1. When a subject has more than about 200 CGG repeats, the fragile X gene is hypermethylated, silenced, fragile X mental retardation protein (FMRP) is not produced and the subject is diagnosed as having fragile X syndrome. See, for example, U.S. Pat. Nos. 6,107,025 and 6,180,337, both of which are hereby incorporated by reference in their entirety.

The fragile X syndrome segregates as an X-linked dominant disorder with reduced penetrance. Children and adults with fragile X syndrome have varying degrees of mental retardation or learning disabilities and behavioral and emotional problems, including autistic-like features and tendencies. About 15 to about 20% of subjects with fragile X syndrome meet the full diagnostic criteria for autism and display other symptoms associated with autism such as attention deficit and hyperactivity, seizures, hypersensitivity to sensory stimuli, obsessive-compulsive behavior, and altered gastrointestinal function.

Despite the common occurrence of irritable, aggressive and self-injurious behavior in subjects with fragile X syndrome, there has been little research assessing treatments for these symptoms. A key tool allowing for a better understanding of the function of FMRP has been development of the FMR1 knockout mouse. As described herein, methods of the present invention are able to treat cognitive and behavioral deficits in FMR1 knockout mice. In addition to being a strong model of fragile X mental retardation, the FMR1 knockout is one of the most studied genetic mouse models used in autism research. See, e.g., Moy et al., *Am. J. Med. Genetics Part C* 142C:40-51 (2006).

Accordingly, in one aspect, provided herein is a method of treating cognitive deficit where the method comprises or consists essentially of administering an effective amount of a MDM2-p53 pathway inhibitor to a subject afflicted with a cognitive deficit, whereby administration of the inhibitor treats, rescues, or otherwise lessens at least one cognitive deficit in the subject. As used herein, the terms "treat" and "treating" refer to both therapeutic treatment and prophylactic or preventative measures, wherein the object is to treat, rescue, ameliorate, or otherwise lessen an undesired cognitive dysfunction. For purposes of this invention, beneficial or desired clinical results include, without limitation, an amelioration of one or more clinical indications, reduced severity of one or more clinical indications, diminishment of the extent or severity of disease, stabilization of the disease state (i.e., not worsening), delay or slowing, halting, or reversing neurodegenerative disease progression, and partial or complete remission, whether detectable or undetectable. Subjects in need of treatment can include those already having, diagnosed with, or suspected of having one or more cognitive deficits associated with fragile X syndrome or autism, as well as those prone to, likely to develop, or suspected of having such cognitive deficits.

As used herein, the term "cognitive deficit" refers to any manifestation of cognitive dysfunction including, without limitation, memory impairment (impaired ability to learn new information or to recall previously learned information), aphasia (language/speech disturbance), apraxia (impaired ability to carry out motor activities despite intact motor function), agnosia (failure to recognize or identify objects despite intact sensory function), disturbance in executive functioning (i.e., planning, organizing, sequencing, abstracting). In some cases, cognitive deficits cause significant impairment of social and/or occupational functioning, which can interfere with the ability of an individual to perform activities of daily living and greatly impact the autonomy and quality of life of the individual. In exemplary embodiments, the cognitive deficit is a memory deficit or learning deficit.

Any inhibitors of MDM2-p53 binding can be used according to a method of the invention. MDM2 binds to the transcriptional activation domain of p53 and thus inhibits this function of p53 (Chen et al., *Mol. Cell Biol.* 1993 13:4107-4114; Oliner et al., *Nature* 1993 362:857-860). Preferably, compounds suitable for use according to the methods described herein include those which (i) inhibit MDM2 activity; (ii) increase phosphorylated p53; (iii) re-activate p53; (iv) inhibit binding of p53 and MDM2; or a combination thereof. Suitable compounds include, without limitation, the small molecule inhibitor Nutlin-3; RG7112; YH239; YH239-EE (an ethyl ester of the free carboxylic acid compound YH239) (see Huang et al., *ACS Chem Biol.* 2014, 9(3): 802-811); SAR405838; a cis-imidazole compound, such as nutlin-3a; a benzodiazepine as disclosed in Grasberger et al., 2005 *J Med Chem* 48:909-912; a RITA (reactivation of p53 and induction of tumor cell apoptosis) compound such as disclosed in Issaeva et al., 2004 *Nat Med* 10:1321-1328; a spiro-oxindole compound as disclosed in Ding et al. 2005 *J Am Chem Soc* 127, 10130-10131 and Ding et al. 2006 *J Med Chem* 49, 3432-3435; or a quininol compound as disclosed in Lu et al. 2006 *J Med Chem* 49, 3759-3762. Spiro-oxindole-based antagonists of the p53-MDM2 interaction are also described in U.S. Pat. Nos. 7,759,383 and 7,737,174. As a further example, an MDM2 inhibitor can be a compound as disclosed in Chene 2003 *Nat. Rev. Cancer* 3, 102-109; Fotouhi and Graves 2005 *Curr Top Med Chem* 5, 159-165; or Vassilev 2005 *J Med Chem* 48, 4491-4499. Other compounds which may reasonably be expected to be active in this use are those MDM2-p53 inhibitors disclosed in U.S. Pat. Nos. 9,079,913 and 8,658,170, each of which is incorporated herein by reference as if set forth in its entirety.

Cognitive deficits that may be treated by the methods provided herein include those associated with known genetic abnormalities such as, for example, FMR1 genetic defect. In some cases, the FMR1 genetic defect comprises a full mutation FXS allele. In other cases, the FMR1 genetic defect comprises a pre-mutation FXS allele. Other genetic and chromosomal conditions associated with cognitive deficits include, for example, Down syndrome (segmental trisomy), Turner syndrome, Williams syndrome, and ATRX (alpha-thalassemia X-linked mental retardation syndrome). In some cases, a FMR1 genetic defect or other genetic abnormality is detected by prenatal or post-natal genetic testing.

Cognitive deficits suitable for treatment according to the methods provided herein are generally associated with aberrant neural stem cell proliferation and reduced neurogenesis. Subjects suitable for treatment according to these methods are post-natal individuals. Without being bound to any theory or mechanism, it is expected that treatment according to a method provided herein would increase differentiation of adult neural stem cells in the post-natal individual.

Methods of the invention can be employed to treat cognitive deficits in learning, memory, executive function, attention and/or processing speed. Such deficits can be deficits associated with or observed in subjects with mental retardation, fragile X syndrome, autism, tuberous sclerosis, Down's syndrome, attention deficit/hyperactivity disorder, and pervasive developmental disorders including idiopathic pervasive developmental disorders and other disorders of brain development. The methods of the invention also can be employed to treat fragile X-associated tremor/ataxia syndrome (FXTAS) and movement disorders. FXTAS is a CGG expansion disease of variable severity. All individuals with FXTAS have an FMR1 premutation in the FMR1 gene, resulting in 55-200 CGG repeats and reduced expression of FMRP. By comparison, an FMR1 full mutation results in an excess of 200 CGG repeats in the 5'-untranslated region of the FMR1 gene, transcriptional silencing of the FMR1 gene, and FXS. FXTAS is characterized by progressive cerebellar ataxia, parkinsonism, dementia and autonomic dysfunction (Baba, Y., et al., *Current Opinion in Neurology* 18:393-398 (2005), the teachings of which are hereby incorporated by reference in its entirety).

As used herein, "subject" refers to an animal or a patient for whom the described treatment is intended. For example, subjects treated according to the methods provided herein are mammals, including by way of example and not limitation, members of rodentia (e.g., mouse, rat, guinea pig), lagomorpha (e.g., rabbits, hares), perissodactyla (e.g., horses, donkeys, etc.), artodactyla (e.g., pigs, cows, sheep), carnivora (e.g., cats, canines), and primates (e.g., apes, monkeys, baboons, and humans). a rodent (e.g., mouse, rat) or a primate (e.g., a monkey, baboon, human). In exemplary embodiments, the subject is a human. Subjects also include animals modified using recombinant DNA and/or transgenic techniques, such as animals modified to inactivate, overexpress, or misexpress genes involved or suspected of involvement in cognitive function.

Any appropriate route or mode of administration to the subject can be employed according to a method provided herein. In exemplary embodiments, an inhibitor of MDM2-p53 binding is administered to a subject as a pharmaceutical composition and in an effective amount to treat and/or prevent a disorder as described herein. A "pharmaceutical composition" refers to a mixture of one or more of the compounds described herein, or pharmaceutically acceptable salts thereof, with other chemical components, such as physiologically acceptable carriers and excipients. One purpose of a pharmaceutical composition is to facilitate administration of a compound to an organism. As used herein, a "pharmaceutically acceptable carrier" refers to a carrier or diluent that does not cause significant irritation to an organism and does not abrogate the biological activity and properties of the administered compound. "Pharmaceutically acceptable salt" refers to those salts that retain the biological effectiveness and properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

Pharmaceutically active compositions and dosage forms of the disclosure include a pharmaceutically acceptable salt of disclosed or a pharmaceutically acceptable polymorph, solvate, hydrate, dehydrate, co-crystal, anhydrous, or amorphous form thereof. Specific salts of disclosed compounds include, but are not limited to, sodium, lithium, potassium salts, and hydrates thereof. Additional examples of pharmaceutically acceptable salts and their methods of preparation and use are presented in Handbook of Pharmaceutical Salts: Properties, and Use (2002), which is incorporated herein by reference. In some cases, compositions can be administered to a subject in need thereof in dosage unit form where each discrete dosage unit contains a predetermined quantity of an active ingredient or compound that was calculated to elicit a desirable therapeutic effect when administered with, in some cases, a pharmaceutically acceptable carrier. The term "pharmaceutically acceptable carriers" as used herein refers to carriers, excipients, or stabilizers that are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The term "therapeutically effective amount" as used herein refers to that amount of a compound, material, composition, medicament, or other material being administered that is effective to achieve a particular biological result or is effective to relieve or prevent to any extent one or more of the symptoms of the disorder being treated or prevented. Biological results to be achieved by administering a therapeutically effective amount include, but are not limited to, one or more of the following: enhancing cognitive function, improving learning (either the rate or ease of learning), improving attention, improving social behavior, improving motor performance, and/or improving cerebrovascular function, particularly in subjects having a condition associated with a fmr1 genetic defect. In various embodiments, "effective amount" refers to an amount suitable to prevent a decline in any one or more of the above qualities, or, in certain embodiments, to improve any one or more of the above qualities, for example, cognitive function or performance, learning rate or ability, problem solving ability, attention span and ability to focus on a task or problem, motor function or performance, social behavior, and the like. Preferably the amelioration or improvement in an individual or population is relative to a cohort, e.g., a control subject or a cohort population that has not received the treatment, or been administered the composition or medicament.

For determining a therapeutically effective dose, it can be advantageous to assess toxicity and therapeutic efficacy of a compound (e.g., an inhibitor of MDM2-p53 binding) in an in vitro assay (e.g., cell cultures) or in experimental animals. For example, the $LD_{50}$ (i.e., the dose lethal to 50% of the population) and $ED_{50}$ (i.e., the dose therapeutically effective in 50% of the population) can be determined. From these calculations, dosage ranges for use in humans can be formulated. Dosage ranges can vary depending on factors such as mode of administration. A therapeutically effective amount of a pharmaceutical composition provided herein can range from about 0.001 to 100 mg of an active ingredient (e.g., compound that inhibits MDM2-p53 binding) per kg body weight of the subject (e.g., about 0.001 to 100 mg/kg body weight; about 0.1 to 40 mg/kg body weight; about 1 to 20 mg/kg body weight). In some cases, an appropriate dose of a pharmaceutical composition can be determined according to body surface area of a subject, calculated using the subject's height and weight, to whom the composition will be administered. In such cases, a dose can be provided as a particular amount of the composition per $m^2$ (e.g., $mg/m^2$). In other cases, dosages and dosage ranges appropriate for a composition provided herein can be determined using pharmacokinetic data (i.e., drug metabolism and clearance). As used herein, "pharmacokinetics" refers to the process by which a drug or pharmaceutical composition is absorbed, distributed, metabolized, and excreted from the body. Additional information about dosage calculation can be found in Center for Drug Evaluation and Research, Center for Biologics Evaluation and Research (2002), *Estimating the safe starting dose in clinical trials for therapeutics in adult healthy volunteers*, U.S. Food and Drug Administration, Rockville, Md., USA.

As stated above, a therapeutically effective dose level will depend on many factors. In addition, it is well within the skill of the art to start doses of the active composition at relatively low levels, and increase the dosage until the desired effect is achieved. Efficacy of the methods provided herein can be determined using any appropriate method. For example, general intellectual functioning is typically measured by an intelligence test that is adjusted for the developmental level to which the test subject is a member. In some cases, a beneficial effect in cognitive deficits can be determined from various standardized tests, such as the Cambridge Neuropsychological Test Automated Battery (CANTAB), which is sensitive to executive function deficits and can report a variety of cognitive impairments, including spatial short-term memory, spatial working memory, set-shifting ability, planning ability, spatial recognition memory, delayed matching to sample, and pattern recognition memory.

Pharmaceutical unit dosage forms of the compounds of this disclosure are suitable for oral, mucosal (e.g., nasal, sublingual, vaginal, buccal, or rectal), parenteral (e.g., intramuscular, subcutaneous, intravenous, intraarterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient. The pharmaceutical compositions may be formulated according to conventional pharmaceutical practice (see, e.g., Remington: *The Science and Practice of Pharmacy,* 20th edition, 2000, ed. A. R. Gennaro, Lippincott Williams & Wilkins, Philadelphia, and *Encyclopedia of Pharmaceutical Technology,* eds. J. Swarbrick and J. C. Boylan, 1988-1999, Marcel Dekker, New York).

The composition, shape, and type of dosage forms of the compositions of the disclosure will typically vary depending on their use. For example, a dosage form used in the acute treatment of a disease or disorder may contain larger amounts of the active ingredient, for example the disclosed compounds or combinations thereof, than a dosage form used in the chronic treatment of the same disease or disorder. Similarly, a parenteral dosage form may contain smaller amounts of the active ingredient than an oral dosage form used to treat the same disease or disorder. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

Clinicians, physicians, and other health care professionals can administer a composition to a subject in need thereof according to a method provided herein. In some cases, a single administration of the composition may be sufficient. In other cases, more than one administration of the composition is performed at various intervals (e.g., once per week, twice per week, daily, monthly) or according to any other appropriate treatment regimen. The duration of treatment can be a single dose or periodic multiple doses for as long as administration of a composition provided herein is tolerated by the subject.

While the present invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents and alternatives falling within the spirit and scope of the invention as defined by the appended claims.

It will be understood that the particular embodiments of the invention are shown by way of illustration and not as limitations of the invention. The principle features of this invention can be employed in various embodiments without departing from the scope of the invention. The invention will be more fully understood upon consideration of the following non-limiting Examples.

EXAMPLES

Example 1—In Vivo Rescue of Cognitive Deficits in FXS

Fragile X syndrome affects 1 in 4000 males and 1 in 6000 females and is the most common form of inherited intellectual disability (1, 2). Fragile X syndrome arises largely due to mutations in the fragile X mental retardation (FMR1) gene, resulting in functional deficiency of fragile X mental retardation protein (FMRP), a brain-enriched RNA-binding protein. Genomewide analyses predict that FMRP regulates many mRNAs (3, 4). FMRP is highly expressed in neurons, and studies show that a loss of FMRP leads to altered expression of many neuronal genes. Therefore, a number of neurotransmitters and neuronal signaling pathways have been intensely investigated as potential therapeutic targets, including pathways associated with group 1 metabotropic glutamate receptor type 5 (mGluR5), N-methyl-D-aspartate receptor subunits, $GABA_A$ receptor, mammalian target of rapamycin, tuberous sclerosis complex 2, and glycogen synthase kinase-3β [reviewed by (1, 5)]. These studies led to a number of potential fragile X syndrome treatments (6). Unfortunately, disappointing results from recent clinical trials of inhibitors of mGluR5, the best known FMRP drug target, underscore a pressing need for innovation in terms of both target selection and consideration of cell types in the central nervous system (CNS) beyond neurons alone (7). Despite the intense interest in fragile X syndrome, especially because of its potential as a gateway to understanding autism, the precise mechanisms behind this unique syndrome remain unclear, and there is still no FDA-approved treatment. Exploring mechanisms to explain the etiology of fragile X syndrome is therefore essential if we are to develop new treatments.

Adult neurogenesis has been explored because of its potential to influence information processing associated with cognitive outcomes (8). Impaired adult neurogenesis is implicated in both neuropsychiatric disorders, such as depression and schizophrenia, and neurodegenerative diseases, such as Alzheimer's and Huntington's disease (9). Interventions aimed at regulating adult neurogenesis are thus being evaluated as potential therapeutic strategies. In many adult organs, both quiescent and activated (actively dividing) stem cells coexist, and the regulation of stem cell activation plays an essential role in tissue maintenance, regeneration, function, plasticity, aging, and disease (10). In the adult hippocampus, quiescent neural stem cells (NSCs) dynamically integrate both extrinsic and intrinsic signals to either maintain their dormant state, or to become activated and give rise to intermediate progenitor cells (IPCs), which subsequently differentiate into postmitotic dentate gyms granule neurons or astrocytes (9). Many studies over the last 20 years have uncovered intracellular factors that regulate the activation of dentate gyms NSCs. Although it is clear that maintaining a balance between quiescence and activation is important for the preservation of adult NSCs, whether this balance directly impacts production of neurons has yet to be explored.

We have shown that FMRP deficiency in adult mouse NSCs leads to increased proliferation of NSCs but reduced differentiation into neurons and impaired hippocampus-dependent learning. Impaired hippocampus-dependent learning can be rescued by either restoring FMRP expression in adult NSCs, or by treating mice with a small molecule that promotes neuronal differentiation (11-13).

Here, we tested the hypothesis that FMRP deficiency leads to activation of adult NSCs, and that rebalancing NSC quiescence and activation could rescue cognitive deficits in a fragile X syndrome mouse model. We show that a loss of FMRP leads to greater activation of adult NSCs. We identified mouse double minute 2 homolog (MDM2), an E3 ubiquitin ligase, as a mediator of FMRP action in adult NSCs. FMRP regulates the expression of MDM2 by reducing the stability of its mRNA. In addition, the absence of FMRP also leads to elevated AKT signaling in NSCs, resulting in enhanced phosphorylation of MDM2. Thus, a lack of FMRP results in increased expression of phosphorylated (activated) MDM2 via two distinct mechanisms. Phosphorylated MDM2 targets and degrades tumor suppressor protein P53. We found that specific inhibition of the MDM2-P53 interaction with a small molecule called Nutlin rescued both the neurogenic and cognitive deficits in fragile X syndrome mice.

Materials and Methods

Study Design:

The purpose of this study was to investigate the role of FMRP in adult NSC activation and whether rebalancing NSC quiescence and activation could rescue both neurogenesis and cognitive deficits in a mouse model of fragile X syndrome. Based on our publications and power analysis, at least 3 to 6 biological replicates were used for each in vitro or in vivo biochemical and histological analysis, whereas a sample size of 9 to 21 per group was used for behavioral testing. The NPCs used for in vitro analyses were isolated independently from different Fmr1 KO and wildtype littermates and were biological replicates. Data collection was carried out for a predetermined period of time, as dictated by literature- or core facility-based standards, and no exclusion criteria were applied. For drug treatment, animals were randomly assigned to treatment arms with approximately equivalent numbers in each group. All cell counting and behavioral analyses were performed by experimenters who were blind to the identity of the samples. All analyses were performed by scientists blinded to genotype and/or treatment arm.

Animal Studies:

All animal procedures were performed according to protocols approved by the University of Wisconsin-Madison Care and Use Committee. All mice were on C57B/L6 genetic background. The Fmr1 KO/Nestin-GFP mice (Fmr1−/y::Nestin-GFP) were created by crossing female Fmr1 heterozygous KO mice (Fmr1+/−) (59) with homozygous Nestin-GFP transgenic males (60). Generation of FMRP inducible conditional mutant mice (Fmr1loxP/y::Nestin-CreERT2::Rosa26-tdt) and tamoxifen injections to induce recombination were performed as described (12). To induce recombination, mice (6-weeks old) received Tamoxifen (Sigma-Aldrich) daily for 5 d (160 mg/kg) as described (12). Nutlin-3 (10 mg/kg) was given to 7-8 week-old mice or 20-week old mice through IP injections every other day for 5 injections and sacrificed at either 24 hours, 4 weeks, 12, or 20 weeks after the last injection. For NSC differentiation analysis, mice also received four BrdU injections (100 mg/kg) between day 2 and 3 of Nutlin-3 injections. To induce recombination in FMRP inducible conditional mutant mice (Fmr1$^{loxP/y}$::Nestin-CreER$^{T2}$::Rosa26-tdt) mice, mice 6-weeks old male mice received Tamoxifen (Sigma-Aldrich) daily for 5 days (160 mg kg-1 i.p., 30 mg ml$^{-1}$ in 10% ethanol mixed with sunflower oil, SigmaAldrich) based on a published procedure (13). BrdU (Sigma-Aldrich, B5002) was made in a concentration of 20 mg/mL in PBS. Nutlin-3 (Nt3, Cayman Chemical, 10004372) was made in a concentration of 100 mg/mL in dimethyl sulfoxide (DMSO).

Tissue Preparation and Immunohistochemistry:

Brain tissue processing and histological analysis of mouse brains were performed as described in our publications (11, 12, 61). Briefly mice were euthanized by IP injection of sodium pentobarbital and then transcardially perfused with saline followed by 4% PFA. Brains were dissected out, post-fixed overnight in 4% PFA, and equilibrated in 30% sucrose. 40 μm brain sections were generated using a sliding microtome and stored as floating sections in cryoprotectant solution (glycerol, ethylene glycol, and 0.1M phosphate buffer, pH 7.4, 1:1:2 by volume). We performed immunohistological analysis on 1-in-6 serial floating brain sections (240 μm apart). After staining with primary and fluorescent secondary antibodies sections were counterstained with DAPI (4',6-diamidine-2'-phenylindole dihydrochloride, 1:2000, Roche Applied Science, Indianapolis, Ind.) and then mounted, coverslipped, and maintained at 4° C. in the dark until analysis.

Antibodies Used in Histological Analysis:

The primary antibodies used were: Chicken-anti-GFP (1:1000, Invitrogen, A10262), rabbit anti-MCM2 (1:500, Cell Signaling, 4007), rabbit anti-GFAP (1:1000, Dako, Z0334), mouse anti-GFAP (1:1000, Millipore, MAB360), mouse anti-Ki67 (1:500, Thermo, 9106S), mouse anti-NeuN (1:500, Millipore, MAB377), rabbit anti-S100β (1:1000, Dako, Z0334), rat anti-BrdU (1:1000, Abcam, ab6326), chicken anti-TBR2 (1:1000, Millipore, AB15894), mouse anti-FMRP (1:1000, Millipore, MAB2106), rabbit anti-P-MDM2 (Ser 166) (1:1000, Novus Biologicals, NBPI-51396).

Fluorescent secondary antibodies used were: goat anti-mouse 568 (1:1000, Invitrogen, A11004), goat anti-rat 568 (1:1000, Invitrogen, A11077), goat anti-rabbit 568 (1:1000, Invitrogen, A11011), goat anti-rabbit 64 7 (1:1000, Invitrogen, A21245), goat anti-mouse 647 (1:1000, Invitrogen, A21235), goat anti-chicken 488 (1:1000, Invitrogen, A11039), goat anti-mouse 488 (1:1000, Invitrogen, A11029).

In Vivo Cell Quantification:

The total numbers of GFP$^+$ or tdT$^+$ cells in the dentate gyrus of each animal were counted on a Zeiss Apotome microscope using unbiased stereology (StereoInvestigator software, MBF Biosciences, Inc). A 5-μm guard zone and exhaustive counting method were used (62). Dentate gyrus volume was measured using StereoInvestigator as described (11, 12). Dorsal (bregma −0.94 to −2.30 mm) and ventral (bregma −2.30 to −3.80 mm) hippocampus regions were defined based on literature Phenotypic analysis was performed as described (12). Briefly, at least 50 GFP$^+$ or BrdU$^+$ cells in the dentate gyrus were randomly selected, and their colocalization with cell-lineage markers was determined using a Nikon A1 confocal microscope and quantified using ImageJ software (NIH).

In Vivo Cell Fate Analysis:

Phenotypic analysis of tdT+ cells was performed as described 3,4. Briefly, at least 50 tdT+ cells in the DG were randomly selected, and their colocalization with cell-lineage markers (e.g., double labeling with GFAP) was determined using Nikon A1 confocal microscope and quantified using Image J software (NIH). Data were presented as the percentage of tdT+ cells. Phenotype analysis of BrdU+ cells was performed as described previously (Luo et al., *PLoS Genet* 6 (2010); Zhao et al., *Proc Natl Acad Sci USA* 100, 6777-6782 (2003); Guo et al., *Hum Mol Genet* 21, 681-691 (2012)). Briefly, at least 50 BrdU+ cells in the DG were randomly selected, and the colocalization of BrdU with cell-lineage markers (NeuN or S100β) was determined using Nikon A1 confocal microscope and quantified using Image J software (NIH). Data were presented as the percentage of BrdU+ cells.

Cell Death Analysis:

Three different methods were used to assay cell death. Fluorescein isothiocyanate and propidium iodide (Annexin V-FITC Apoptosis Detection Kit, Sigma, #APOAF) were used to assess NSC apoptosis. Intact cells were Annexin $V^-PI^-$. Early and late apoptotic cells were Annexin $V^-PI^-$ and Annexin $V^+PI^+$, respectively. Necrotic cells were Annexin V-PI+. The number of early apoptotic cells (Annexin $V^+PI^-$; Phase II) and late apoptotic cells (Annexin $V^+PI^+$, Phase I) were used to calculate the percentage of apoptotic cells. In a second method, propidium iodide (1 mg/mL) and Hoechst43332 (1 mM) were added to cultured cells for 15 min, followed by high content imaging analysis (Oppretta, GE) to quantify the percentage of Hoechst positive (all) cells that are PI positive (dead) cells. In the third method, Cell viability was measured using CellTiter-Glo Luminescent Cell Viability Assay (Promega). 2 μM Nutlin-3 (Nt3, Selleckchem, 51061) was added to proliferating aNPCs at 6 hours post-plating. Cells were then harvested 24 hours later with CellTiter-Glo buffer at room temperature. Signal intensity was immediately measured using a Glomax plate reader (Promega) according to manufacturer's instruction.

Adult NPC Analyses:

NPCs were isolated from the dentate gyms of 8 to 10-week-old male Fmr1 KO mice and wild-type (wildtype) littermate controls based on our published methods (12, 64). Independently isolated cells serve as biological replicates. Proliferation and differentiation of NPCs was analyzed as described (11, 12, 61). We used only early passage cells (between passage 4 and 10) and only the same passage numbers of wildtype and Fmr1 KO cells. For each experiment, triplicate wells of cells were analyzed, and results were averaged as one data point (n=1). At least 3 independent biological replicates were used (n=3) for statistical analyses.

Bioinformatics Analysis:

To select candidate FMRP targets, we utilized FMRP CLIP data from Ascano et al. (3). mRNA transcripts were ranked by the number of reads precipitated in the experiment, and an arbitrary threshold of 1000 reads was chosen to determine the most likely targets of FMRP. This cutoff yielded 417 top genes, or approximately 2% of all probes in the experiment. 16 genes with known roles in adult NSC activation or proliferation were selected from the Mammalian Adult Neurogenesis Gene Ontology (MANGO available at mango.adult-neurogenesis.de on the world wide web) database and literature, and were named "Neurogenic Regulators". For each of these "Neurogenic Regulators", all known physical interactions were mapped by BioGrid 3.4 (http://thebiogrid.org) and GeneMania (http://www.genemania.org), producing 16 networks of 335 unique proteins that interact with neurogenic regulators ("Neurogenic Interactors"). Additionally, the number of articles supporting each interaction as listed by BioGrid 3.4 was used as an indicator of the strength of a given interaction. Overlap was then assessed between candidate FMRP targets and both "Neurogenic Regulators" and "Neurogenic Interactors" to find proteins likely to be regulated by FMRP that influence adult NSC activation.

Proliferation and Differentiation Analyses of Cultured aNPCs:

Proliferation and differentiation of aNPCs were analyzed using our published methods (Guo et al., Nature Med. (2011); Guo et al., Neuron 70, 924-938 (2011); Luo et al., *PLoS Genet* 6 (2010); Liu et al., *Cell Stem Cell* 6 (2010)). We used only early passage cells (between passage 4 and 10) and only the same passage numbers of wild type (WT) and Fmr1 KO cells. For each experiment, triplicate wells of cells were analyzed, and results were averaged as one data point (n=1). At least 3 independent experiments (n=3) were performed and used for statistical analyses for each analysis. To study cell proliferation, we dissociated neural stem cells with trypsin and plated them on poly-L-ornithine and laminin-coated 24 well plate (Scientific fisher, 87721) at a density of 100,000 cells per well in proliferation medium. At 20 h post-plating, 5 μM 5-bromo-2.'-deoxyuridine (BrdU, Sigma-Aldrich) was added into the culture medium for 6 h. NPCs were then washed with PBS and fixed with 4% paraformaldehyde for 30 min at room temperature, followed by immunohistochemical analysis. To detect BrdU incorporation, fixed cells were pretreated with 1M HCl for 30 min at 37° C., and then washed with borate buffer, pH 8.5, for 30 min. We then followed our standard immunohistochemistry protocol[10]. BrdU incorporation assay was determined using an Operetta high content imaging system (PerkinElmer, Inc) and Harmony quantification software (PerkinElmer, Inc). The percentage of proliferating cells was defined as the number of BrdU-labeled cells divided by total DAPI-positive cells. In a preliminary experiment, we found that stereology counting and Operatta imaging yielded consistent results for BrdU proliferation assays. For the differentiation assay, at 24 h post-plating, cells were changed into differentiation medium, Neurobasal A, containing 5 μM forskolin (Sigma-Aldrich, F-6886) and 1 μM retinoic acid (Sigma-Aldrich, R-2625) for 4 d, followed by fixation with 4% paraformaldehyde for 30 min, and then washed with Dulbecco's Phosphate Buffered Saline (DPBS), pH 7.4 for 30 min. Immunocytochemistry staining was carried out as described (Guo et al., Nature Med. (2011); Guo et al., Neuron 70, 924-938 (2011); Luo et al., *PLoS Genet* 6 (2010); Liu et al., *Cell Stem Cell* 6 (2010)). Briefly, cells were preblocked using DPBS containing 5% normal goat serum (VECTOR, S-1000) and 0.1% Triton X-100 for 30 min, followed by overnight incubation with primary antibodies: mouse anti-Tuj1 (1:1000, Promega, G712A) and rabbit anti-S100β (1:1000, Dako, Z0334).

After washing with Dulbecco s Phosphate Buffered Saline (DPBS), cells were incubated with secondary antibodies that included goat anti-mouse 568 (1:1000, Invitrogen, A11031), goat anti-rabbit 488 (1:1000, Invitrogen, A11008) followed by counterstaining with the fluorescent nuclear dye 4',6-diamidino-2'-phenylindole dihydrochloride (DAPI, Sigma-Aldrich, B2261). After the cells were mounted with VECTASHIELD (VECTOR, H-1000), the numbers of Tuj1, GFAP-positive cells were quantified using an Olympus BX51 microscope equipped with a MicroFire digital camera (Optronics) and a motorized stage using a 20× objective lens. The quantification was carried out using an unbiased stereology method with assistance from StereoInvestigator software (MBF Biosciences). The percentage of differentiated cells was calculated as the number of Tuj1- or GFAP-labeled cells divided by the total number of cells stained with DAPI. Quantification was performed by scientists who were blinded to experimental conditions.

Transfection and Luciferase Assay:

NeuroD1-luciferase (ND1-Luc), GFAP-luciferase (GFAP-Luc), and internal control E1α-renilla luciferase (R-Luc) DNA plasmids were described previously (Liu et al., Cell Stem Cell 6 (2010)). Transfection of aNSCs was carried out using Fugene HD (Roche, 04709713001) based on the manufacturer's protocol with modification. Briefly, aNPCs were plated into 24-well P/L coated plate for 24 hours. In a separate tube, 1 µg DNA was added into 50 µl DMEM/F12 medium without phenylsulfonyl fluoride (PMSF), followed by the addition of 3 µl Fugene HD transfection reagent. The mixture was mixed by pipetting 3-5 times, incubated for 30 minute, and then added onto the cells. Sixteen hours later, the transfected cells were changed into differentiation medium for 24-48 hours before harvesting. Luciferase activity was detected using the Dual-Luciferase Reporter 1000 System (Promega, E1980) based on the manufacturer's protocol. Briefly, collected cells were lysed in 100 µl of 1× passive lysis buffer at room temperature for 15 min. Then 20 µL of the lysate was added to 100 µl of Luciferase Assay Buffer II and mixed briefly. ND1-Luc or GFAP-Luc activity was immediately read using a Glomax plate reader (Promega.). Next, 100 µl of Stop & Glo Buffer with Stop & Glo substrate was added and mixed briefly. Renilla luciferase (R-luc) activity was immediately read. ND1-Luc or GFAP-Luc was normalized to R-Luc activity to account for neuronal differentiation or astroglial differentiation of aNPCs.

Chemical Treatment:

For proliferation assay in vitro, 1 µM MK2206 (Selleckchem, S1078) (AKT phosphorylation inhibitor), or 2 µM Nutlin-3 (Nt3, Selleckchem, 51061) (Mdm2 inhibitor), or 1 µM RG7112 (Selleckchem, S7030) (Mdm2 inhibitor) or YH239-EE (Selleckchem 57489) (4 µM) (Mdm2 inhibitor) was added to proliferating NPCs at 6 hours post-plating. Cells were then pulse labeled 18 hours later with 5 µM 5-bromo-2'-deoxyuridine (BrdU, Sigma-Aldrich, B5002) and incubated for 6 hours in the presence of inhibitor, followed by fixation, staining, and quantification. For differentiation assay in vitro, 1 µM MK2206 and 2 µM Nt3 were added to NPCs upon initiation of differentiation with RA/Fsk for 4 days, followed by fixation, staining and stereological quantification.

RNA Immunoprecipitation:

RNA-immunoprecipitation (IP) was performed as described (11, 61). Briefly, wildtype and Fmr1 KO NPCs were harvested and homogenized in 1 ml of ice-cold lysis buffer (10 mM Hepes [pH 7.4], 200 mM NaCl, 30 mM EDTA, and 0.5% Triton X-100) with 2× complete protease inhibitors (Boehringer-Mannheim). Nuclei and debris were pelleted at 3,000×g for 10 min; the supernatant was collected and raised to 300 mM NaCl, and clarified at 14,000×g for 30 min. The resulting supernatant was pre-cleared for 1 h with 100 µL recombinant protein G agarose (Invitrogen) (prewashed with lysis buffer). An aliquot of pre-cleared input was saved for RNA extraction (200 µL) and protein analysis (100 µL). A monoclonal antibody against FMRP (7G1-1, DSHB) or a monoclonal antibody against IgG (5415S, Cell Signaling) was incubated with recombinant protein G dynabeads at 4° C. for 2 h and washed 3 times with lysis buffer. RNase Inhibitors (Roche) were added to the remaining lysates. The pre-cleared lysates were immunoprecipitated with antibody-coated recombinant protein G agarose at 4° C. for 2 hours. After three washes with lysis buffer, 10% of immunoprecipitate was saved for protein analysis. The remainder was washed one more time and the immunoprecipitate was re-suspended into Trizol (Invitrogen) for RNA isolation.

Real-Time PCR Assay:

Real-time PCR was performed using standard methods as described (61). The first-strand cDNA was generated by reverse transcription with Oligo (dT) primer (Roche). To quantify the mRNA expression using real-time PCR, aliquots of first-stranded cDNA were amplified with gene-specific primers and Power SYBR Green PCR Master Mix (Bio-Rad) using a Step-1 Real-Time PCR System (Applied Biosystems). The PCR reactions contained 1 µg of cDNA (except the cDNA for the IP, for which 5% of the cDNA was used for each gene examined), Universal Master Mix (Applied Biosystems), and 10 µM of forward and reverse primers in a final reaction volume of 20 µL. The mRNA expression of different samples was calculated by the data analysis software built in with the 7300 Real-Time PCR System. For RIP-real time PCR, cDNA from IP and input was used and IP samples were normalized to Input samples. The Sequences of primers are provided in supplementary methods.

Real-time PCR were performed using standard methods as described (65). The first-strand cDNA was generated by reverse transcription with Oligo (dT) primer (Roche). To quantify the mRNA levels using real-time PCR, aliquots of first-stranded cDNA were amplified with gene specific primers and Power SYBR Green PCR Master Mix (Bio-Rad) using a Step-I Real-Time PCR System (Applied Biosystems). The PCR reactions contained 1 µg of cDNA (except the cDNA for the IP, for which 5% of the cDNA was used for each gene examined), Universal Master Mix (Applied Biosystems) and 10 µM of forward and reverse primers in a final reaction volume of 20 µL. The mRNA level of different samples was calculated by the data analysis software built in with the 7300 Real-Time PCR System. For RIP-real time PCR, cDNA from IP and input was used and IP samples were normalized to Input samples. The sequences of primers are provided.

Sequences of primers used for Real-time PCR reactions were as follows:

```
Mdm2:
                        (SEQ ID NO: 1)
Forward:       AGCAGCGAGTCCACAGAGA (SEQ ID NO: 2)
Reverse:       ATCCTGATCCAGGCAATCAC Map1b:
                        (SEQ ID NO: 3)
Forward:       GGCAAGATGGGGTATAGAGA (SEQ ID NO: 4)
Reverse:       CCCACCTGCTTTGGTATTTG G5K3β
                        (SEQ ID NO: 5)
Forward:       GGGACAGTGGTGTGGATCAG (SEQ ID NO: 6)
Reverse:       CTTGTTGGTGTTCCTAGGAC Gapdh:
                        (SEQ ID NO: 7)
Forward:       GCTCCTCCCTGTTCCAGAGACGG (SEQ ID NO: 8)
Reverse:       ACAATCTCCACTTTGCCACTGC
```

-continued

Human MDM2

Forward: GCAGTGAATCTACAGGGACGC (SEQ ID NO: 9)

Reverse: ATCCTGATCCAACCAATCACC (SEQ ID NO: 10)

Human Gapdh

Forward: GCTCCTCCCTGTTCCAGAGACGG (SEQ ID NO: 11)

Reverse: ACAATCTCCACTTTGCCACTGC (SEQ ID NO: 12)

Yhwaz

Forward: TCCTTATTCCCTCTTGGCAG (SEQ ID NO: 13)

Reverse: ATGGAAGCTACATTAGCGGTTT (SEQ ID NO: 14)

Mdm2 mRNA Stability Assay:

Dentate gyrus-NPCs from wildtype and Fmr1 KO mice were grown under proliferating conditions, meaning in the presence of growth factors that suppress differentiation. 10 μg/ml of Actinomycin D (Sigma-Aldrich) was added based on published protocol (61) and total RNA was isolated at various time intervals. The Mdm2 mRNA expression was normalized to Gapdh or Ywhaz mRNA as measured by real time PCR. RNA decay kinetics and half-life were analyzed using published methods (62). Briefly, we used the exponential function $M=M0e^{-\lambda t}$ (M: amount of mRNA at t time, M0: amount of mRNA at t time). $\lambda =(ln)/T\frac{1}{2}$ (T½ is the half-life of the mRNA).

Western Blotting Analyses:

Protein samples were separated on SDS-PAGE gels (Bio-Rad), transferred to PVDF membranes (Millipore), and incubated with primary antibodies. After incubation with fluorescence-labeled secondary antibodies (Li—CoR), the membranes were imaged using Li—CoR and quantification was performed using ImageJ software. At least n=3 independent blots were used for statistical analysis.

Antibodies Used in Western Blotting Analysis:

MDM2 (1:1000, Santa Cruz,), P-MDM2 (Ser166) (1:1000, Novus Biologicals, NBP1-51396), P53 (1:1000, Santa Cruz, SC-6243), P-AKT (Ser473) (1:1000, Cell Signaling, 9271 S), AKT (1:1000, Cell Signaling, 9272S), and GAPDH (1:5000, Thermo Scientific, MA5-15738) were used as primary antibodies. For loading controls, membranes were probed with the mouse antibody against GAPDH.

Human Tissues:

Human tissue was obtained from the University of Maryland Brain and Tissue Bank, a Brain and Tissue Repository of the NIH NeuroBioBank. Frozen hippocampal and cortical tissues from two age, gender, and postmortem time-matched patients with fragile X syndrome (80 and 85 years old) and two control male Caucasian individuals (82 and 84 years old) were used for MDM2 mRNA and p-MDM2 (S166) analysis.

Novel Location Test (NLT):

This test measures spatial memory through an evaluation of the ability of mice to recognize the new location of a familiar object with respect to spatial cues. The experimental procedure was performed as previously described (65). The mice were exposed to 2 identical objects for 6 minutes during the acquisition phase 3 times and tested at 3 minutes later. Object preference was evaluated during this session. During the trial session, one of the objects was moved to a novel location, and the mice were allowed to explore the objects for 6 minutes, and the total time spent exploring each object was measured. Exploration was considered as any investigative behavior (i.e., head orientation, sniffing occurring within <1.0 cm) or deliberate contact occurring with each object. The discrimination index was calculated as the percentage of time spent investigating the object in the new location minus the percentage of time spent investigating the object in the old location: discrimination index=(Novel Location exploration time/total exploration time×100)−(old Location exploration time/total exploration time×100). All experiments were videotaped and scored by scientists who were blinded to experimental conditions.

Novel Object Recognition (NOR) Test:

This test is based on the natural propensity of rodents to preferentially explore novel objects over familiar ones. The experimental procedure was performed as previously described (38). On the first day, mice were habituated for 10 min to the maze in which the task was performed. On the second day, mice were put back in the maze for 10 min, and two identical objects were presented. 24 hours later, one of the familiar objects was replaced with a novel object, and the mice were again placed in the maze and were allowed to explore for 10 min, and the total time spent exploring each of the two objects (novel and familiar) was measured. The discrimination index was calculated as the difference between the percentages of time spent investigating the novel object and the time spent investigating the familiar objects: discrimination index=(novel object exploration time/total exploration time×100)−(familiar object exploration time/total exploration time×100). All experiments were videotaped and scored by scientists who were blinded to experimental conditions.

Open Field Activity Test:

Mice were subjected to open field testing for evaluation of locomotor activity and general anxiety. Activity was recorded at 10-min intervals for total 30 min by means of a computer-operated tracking system (Omnitech Electronics Inc, USA) Total distance moved, and ratio of entry time into the Centre and periphery of arena were measured.

Statistical Analysis:

All experiments were randomized and blinded to scientists who performed quantification. Statistical analysis was performed using ANOVA and Student's t-test, unless specified, with the GraphPad software. Two tailed and unpaired t-test was used to compare two conditions. One-Way ANOVA was used for comparison among multiple experimental conditions. Bonferroni post hoc test was used when comparing among each condition. For Mdm2 mRNA stability analysis, Two-Way ANOVA was used for comparison of the different decay rates. All data were shown as mean with standard error of mean (mean±SEM). Probabilities of P<0.05 were considered as significant.

Results

Figures 1A, 1O:
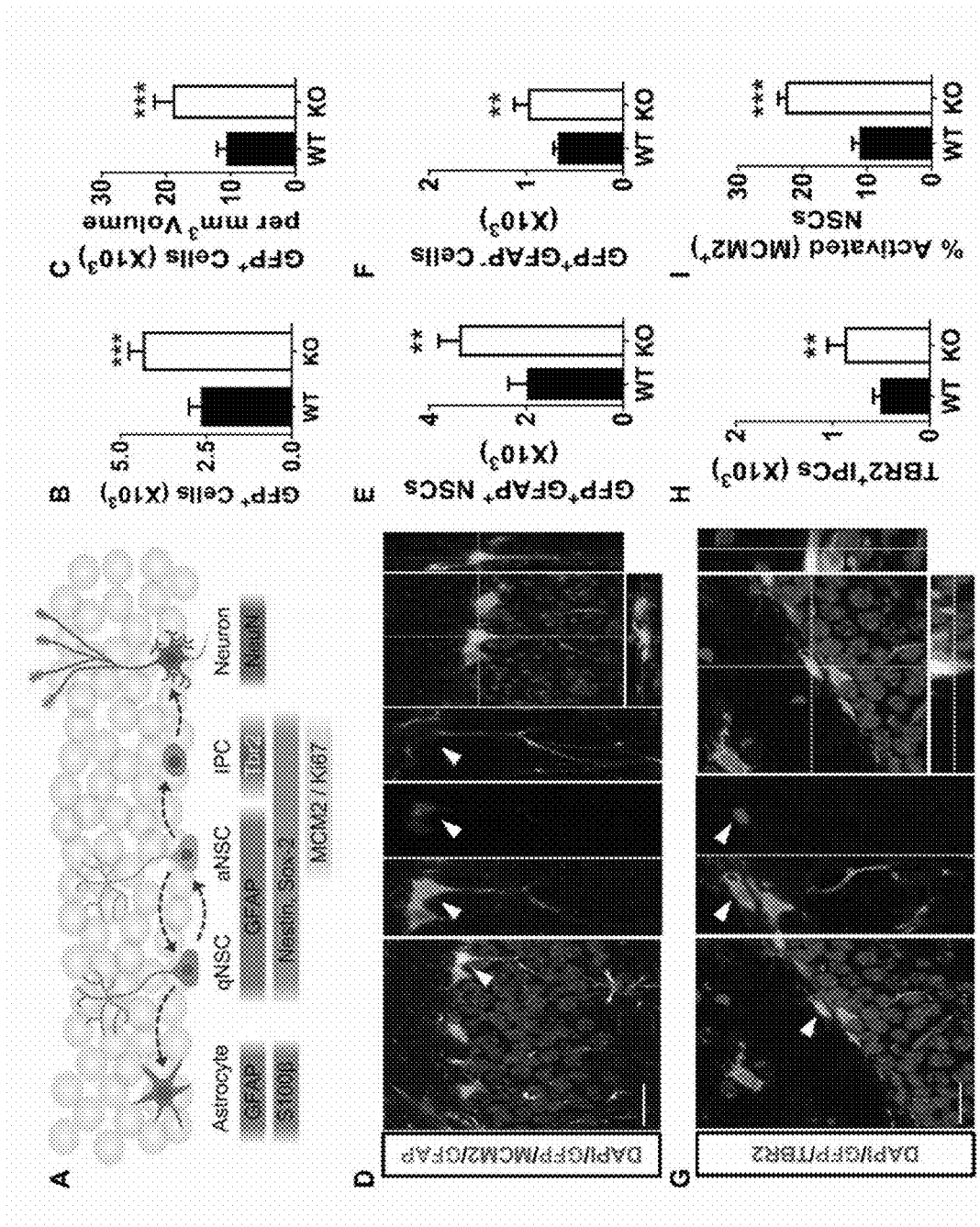
FIGS. 1A-1O demonstrate that FMRP deficiency leads to increased NSC activation in the adult dentate gyms. (A) Schematic diagram showing stages of neurogenesis in the adult dentate gyms and cell lineage-specific markers. qNSC, quiescent NSC. aNSC, activated NSC. (B and C) Quantitative comparison of the number of total GFP+ cells (B) and the density of GFP+ cells (C) in the dentate gyms of adult Fmr1 KO mice and wildtype (WT) littermate controls. (D) Sample confocal images used in E, F and I for identifying NSCs (GFP+GFAP+), progenitors (GFP+GFAP−), activated NSCs (GFP+GFAP+MCM2+) in the dentate gyms of adult Fmr1 KO mice and wildtype (WT) mice bred onto a Nestin-GFP mouse background. Blue, DAPI; Green, GFP; Red, MCM2; white, GFAP. Scale bars: 20 µm. (E and F) Quantitative comparison of the number of NSCs (E) and IPCs (F) in the mouse dentate gyms. (G, H), Sample confocal images (G) and quantitative comparison of the number of IPCs (GFP+TBR2+) in the adult mouse dentate gyms. (I) Comparison of the percentage of activated NSCs (GFP+GFAP+MCM2+) among the total NSCs (GFP+GFAP+) in the mouse dentate gyms. (J) Sample confocal images used in K and L for identifying proliferating (Ki67+) NSCs (GFP+GFAP+Ki67+) and progenitors (GFP+GFAP−Ki67+). Green, GFP; red, Ki67; white, GFAP; white arrow heads indicate proliferating aNSCs; white arrows indicate proliferating IPCs; Scale bars: 20 µm. (K) Comparison of the percentage of proliferating NSCs among total NSCs in the mouse dentate gyms. (L) Comparison of the percentage of proliferating progenitors among total progenitors. (M) Sample confocal images from Fmr1-cKO mice used for identifying activated NSCs (tdT+GFAP+MCM2+). Green, MCM2; red, tdT; white, GFAP. Scale bars: 20 µm. (N) Quantitative comparison of the total numbers of activated NSCs in the dentate gyms of cKO::Cre::Ai14 mice and Cre.
Figures 1A, 1O:
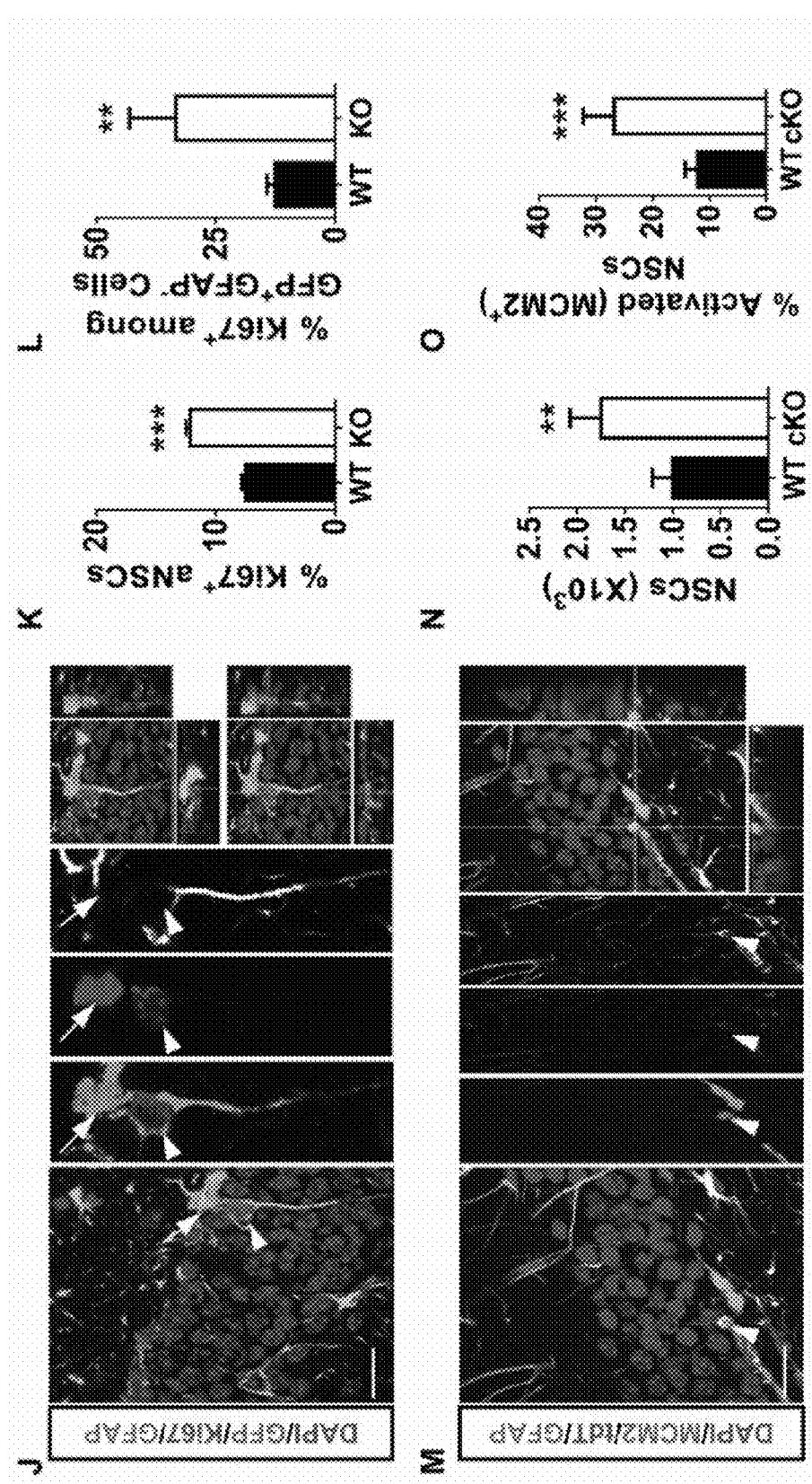

FMRP Deficiency Leads to Increased NSC Activation:

To investigate the role of FMRP in regulating activation of NSCs, we crossed Fmr1 mutant (KO) mice with mice expressing green fluorescent protein (GFP) driven by the promoter of a neural progenitor cell marker Nestin (Nestin-GFP). We thus created both Fmr1 KO (Fmr1$^{-/y}$::Nestin-GFP) and wildtype (Fmr1$^{+/y}$::Nestin-GFP) mice in which adult mouse neural stem cells (NSCs) and intermediate progenitors (IPCs) were labeled by GFP (FIG. 1A, and FIG. 8A). We found that the Fmr1 KO mice had an increased number (FIG. 1B) and density (FIG. 1C) of GFP$^+$ cells in the dentate gyms compared to their wildtype littermates but without significant changes in the overall volume of the dentate gyms (FIG. 8, C, p=0.76 and D, p=0.47, n=5, t-test). We next analyzed different populations of GFP+ cells in the subgranular zone using the radial glia marker glial fibrillary acidic protein (GFAP) for type 1 radial glia-like NSCs (GFP+GFAP+) and the marker TBR2 for IPCs (TBR2+ or GFP+GFAP−). Fmr1 KO mice had a greater number of NSCs (FIGS. 1, D and E, p<0.01, n=5, t-test) and IPCs (FIGS. 1F-H, p<0.0001, n=5, t-test for both F and H) compared to their wildtype littermates. We then used MCM2, a marker for cell cycle initiation and stem cell activation to distinguish activated NSCs (GFP+GFAP+MCM2+) from quiescent NSCs (GFP+GFAP+MCM2−) (FIG. 1D and FIG. 8E). Fmr1 KO mice had a higher percentage of activated NSCs (FIG. 1I, p<0.0001, n=5 t-test) and a higher number of MCM2+ cells (FIG. 8F, p<0.0001, n=5 t-test) in the adult dentate gyms compared to their wildtype littermates. In addition, the total numbers of GFP+ cells, NSCs, and IPCs, as well as activated (MCM2+) cells were elevated in both dorsal and ventral dentate gyms (FIGS. 8G-8O). As expected, both NSCs and progenitor cells exhibited greater proliferation as assessed by the cell cycle marker Ki67 in Fmr1 KO versus wildtype mice (FIGS. 1J to 1L; K, P<0.0001, L, p<0.01; n=5, t-test). Thus, a loss of FMRP leads to increased activation and proliferation of NSCs in the adult dentate gyms.

To determine whether FMRP regulation of NSC activation is intrinsic to NSCs, we created a triple transgenic line (cKO::Cre::Ai14) by crossing Fmr1-floxed (cKO) mice with inducible Nestin promoter (Nes)-driven Cre transgenic mice (Nes-CreERT$^2$) and Rosa26-STOP-tdTOmato (Ai14) reporter mice as described previously (12) (FIG. 9A). We injected adult triple transgenic mice (cKO::Cre::Ai14) and control littermates (Cre::Ai14) with tamoxifen to achieve targeted deletion of FMRP specifically in adult NSCs and their subsequent progenies, and 4 weeks later analyzed the steady-state level of NSC activation by assessing the number of tdTomato-positive (tdT+) cells that both expressed GFAP and met the morphological criteria of NSCs. We found that the cKO::Cre::Ai14 mice had more NSCs (tdT+GFAP+) (FIGS. 1M and 1N and FIG. 9B) and elevated NSC activation compared to Cre::Ai14 littermates (FIG. 1O, p<0.0001, n=6, t-test). Again, the overall volume of the dentate gyms was unchanged (FIG. 9C). These data demonstrate that the NSC activation deficit was the result of an intrinsic deficiency of FMRP expression in NSCs and was not due to a deficiency of FMRP expression in other cell types. These data also suggest that FMRP regulates NSC activation via an intrinsic mechanism within NSCs.

FMRP Regulates MDM2 Expression in Adult Neural Stem/Progenitor Cells:

FMRP is known to bind to a subset of specific mRNAs in the brain and regulate their translation (4, 14). Given that our goal was to discover FMRP targets that regulate NSC activation, we used published FMRP PAR-CLIP data on proliferating cells (HEK 293 cells) (3) to select candidate FMRP targets. Given that the number of FMRP-associated reads precipitated for each mRNA reflects the likelihood of interaction, we chose an arbitrary threshold of 1000 reads, yielding 417 prospective FMRP-regulated mRNAs (FIG. 2A, "FMRP Candidate Targets") (see also Supplementary Table S1 in Li et al., Science Translational Medicine 8(336): 336ra61 (2016), which is incorporated herein by reference in its entirety). We also searched the Mammalian Adult Neurogenesis Gene Ontology (MANGO) database (15) and literature to curate a set of 16 "Neurogenic Regulators" with well-established roles in adult NSC quiescence and activation (FIG. 2A; Table 2). Among them, only MDM2 (murine double minute-2 protein) also appeared as one of the 417 FMRP Candidate Targets. Since FMRP may influence neurogenesis by acting either directly on these 16 Neurogenic Regulators or on related proteins participating in their functional pathways, we used the BioGRID 3.4 protein interaction database and GeneMania to identify 322 proteins that have literature-supported physical interactions with the 16 Neurogenic Regulators, including some of the core Neurogenic Regulators themselves (see Supplementary Table S3 in Li et al., Science Translational Medicine 8(336): 336ra61 (2016), which is incorporated herein by reference in its entirety). Comparing these 335 "Neurogenic Interactors" to the 417 candidate FMRP targets revealed an intersection of 29 putative FMRP targets known to participate in neurogenic pathways. Candidates were ranked by the number of pathways in which they participated, and MDM2 ranked first with four interactions supported by twenty-five publications (Table 1). Importantly, the known interaction between MDM2 and its target P53, is an established mechanism for regulating NSC activation (16). Because MDM2 was among our core Neurogenic Regulators and exhibited the highest degree of interaction with strongly supported neurogenic pathways, we chose to focus on MDM2 as the mediator of FMRP-regulated NSC activation.

Figures 2A, 2B, 2C, 2D, 2E, 2F, 2G, 2H:
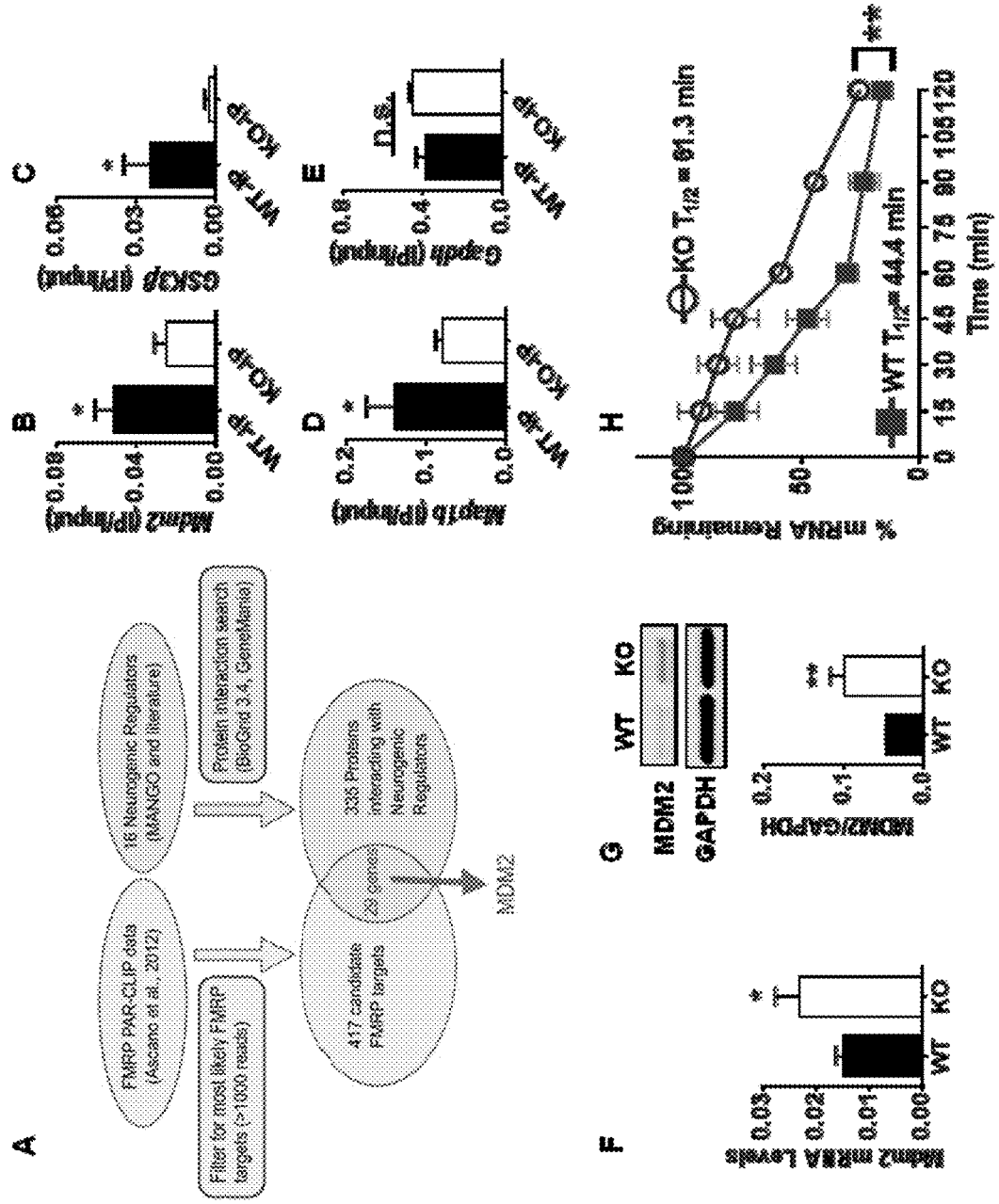

Next, we used primary neural stem/progenitor cells (NPCs) isolated from the adult dentate gyms as a model system to interrogate the mechanism behind FMRP's regulation of aNSC activation. We confirmed that Fmr1 KO NPCs indeed exhibited increased proliferation and astroglial production but reduced neuronal differentiation (FIG. 10), as described previously (11-13). To determine whether FMRP regulates MDM2, we performed RNA binding protein immunoprecipitation and identification of co-precipitated RNA (RNA-IP) with an FMRP antibody coupled with real-time PCR analysis of Mdm2 mRNA. We confirmed that FMRP associated with Mdm2 mRNA in NPCs (FIG. 2B). We also detected the association of FMRP with Gsk3β and Map1b mRNAs, two known targets of FMRP (11, 17), but not with Gapdh mRNA (18) (FIG. 2, C to E), validating the specificity of our assay.

Figure 13A:
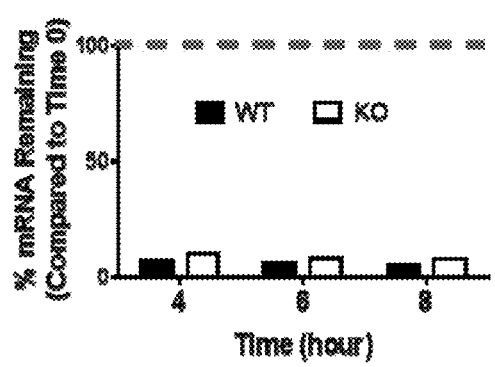
Figure 13B:
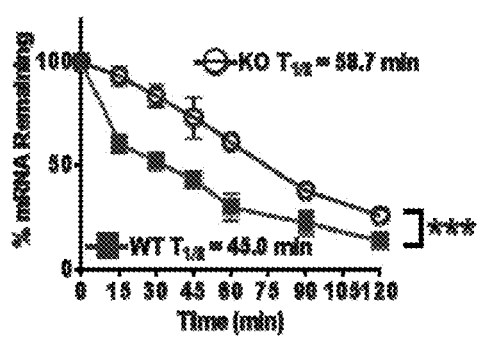
Figure 13C:
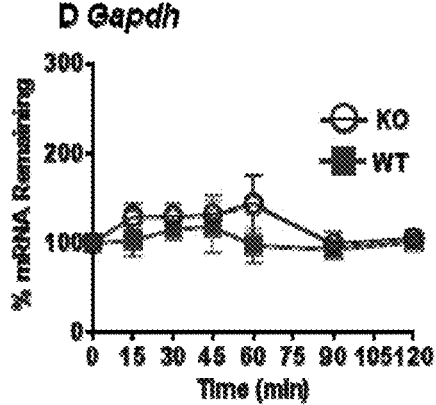
Figure 13D:
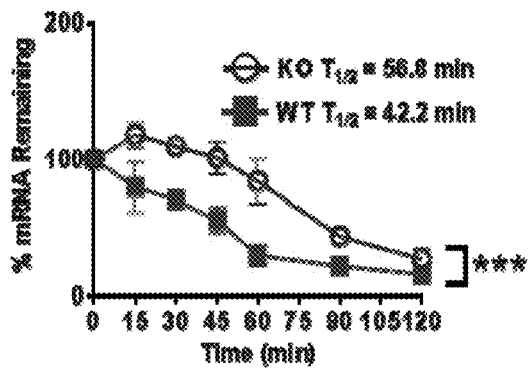
Figure 13E:
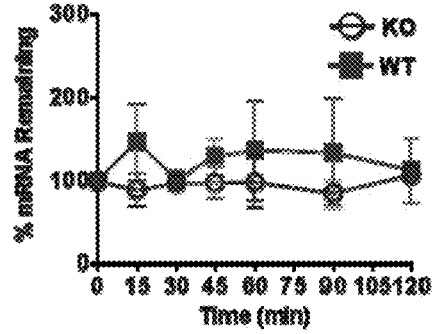

We next found that both Mdm2 mRNA and MDM2 protein expression were higher in Fmr1 KO NPCs compared to wildtype NPCs (FIGS. 2F and 2G; FIG. 11 and FIG. 12A). The higher Mdm2 mRNA expression could be due to either increased gene transcription or increased mRNA stability. Because FMRP is known to associate with target mRNAs and modulate mRNA stability (19), we evaluated Mdm2 mRNA decay kinetics over an 8-hour period in Fmr1 KO and wildtype NPCs in the presence of an inhibitor of transcription, actinomycin D. We found that Mdm2 mRNA exhibited fast decay kinetics, with most (>90%) RNA disappearing within 4 hours in both wildtype and KO NSCs (FIG. 13A). We then repeated this experiment by analyzing mRNA over a 120-minute period. We found that Mdm2 mRNA had a longer half-life in Fmr1 KO ($T_{1/2}$=58.7–61.3 minutes) versus wildtype ($T_{1/2}$=44.4–45.0 minutes) NPCs (FIG. 2H, FIGS. 13B and 13C), whereas the decay of control Gapdh and Ywhaz mRNA exhibited no difference between genotypes (FIGS. 13D-13E). Therefore, FMRP controls MDM2 expression in NPCs at least in part by reducing the half-life of Mdm2 mRNA.

TABLE 1

Number of physical interactions between FMRP candidate targets and neurogenesis regulators with role in NSC activation

| FMRP candidate targets | Number of interactions with neurogenesis regulators | Number of published evidence for interactions (provided by BioGrid) |
| --- | --- | --- |
| MDM2 | 4 | 25 |
| EP300 | 3 | 4 |
| PPP2CA | 2 | 2 |
| HUWE1 | 2 | 1 |
| PRKDC | 2 | 1 |
| CTNNB1 | 1 | 2 |
| APC | 1 | 2 |
| HSP90AA1 | 1 | 2 |
| POLE | 1 | 2 |
| PARP1 | 1 | 2 |
| RAD21 | 1 | 1 |
| IGF1R | 1 | 1 |
| KCTD20 | 1 | 1 |
| NOTCH2 | 1 | 1 |
| HIPK2 | 1 | 1 |
| HIPK1 | 1 | 1 |
| PPP1CC | 1 | 1 |
| LIFR | 1 | 1 |
| VAPB | 1 | 1 |
| UBA2 | 1 | N/A |
| CCP110 | 1 | N/A |
| XPO1 | 1 | N/A |
| YY1 | 1 | N/A |
| CHD4 | 1 | N/A |
| CDK6 | 1 | N/A |
| JMY | 1 | N/A |
| EEF1A1 | 1 | N/A |
| PRKAA2 | 1 | N/A |
| BACH1 | 1 | N/A |

N/A: No published literature provided by BioGrid analysis. The interaction was supported by GeneMania analyses.

TABLE 2

Neurogenic Regulators that Regulate Adult Neural Stem Cell Quiescence and Activation

| Gene | References |
| --- | --- |
| P53 | (66) |
| AKT1 | (67) |
| TLX | (67) |
|  | (68) |
| SOX2 | (69) |
| SHH | (70) |
| NOTCH1 | (71) |
|  | (72) |
| RBPJ | (73) |
| MDM2 | (74) |
| EPHA4 | (75) |
| PROX1 | (76) |
| STAT3 | (77) |
|  | (78) |
| PEDF | (78) |
|  | (79) |
| CNTF | (80) |
| SMO | (81) |
| P73 | (82) |
| PTEN | (24) |

(Note: The list was created by searching both the MANGO data base (15) and literature)

Figures 3A, 3B, 3C, 3D, 3E, 3F, 3G, 3H, 3I, 3J, 3K, 3L, 3M:
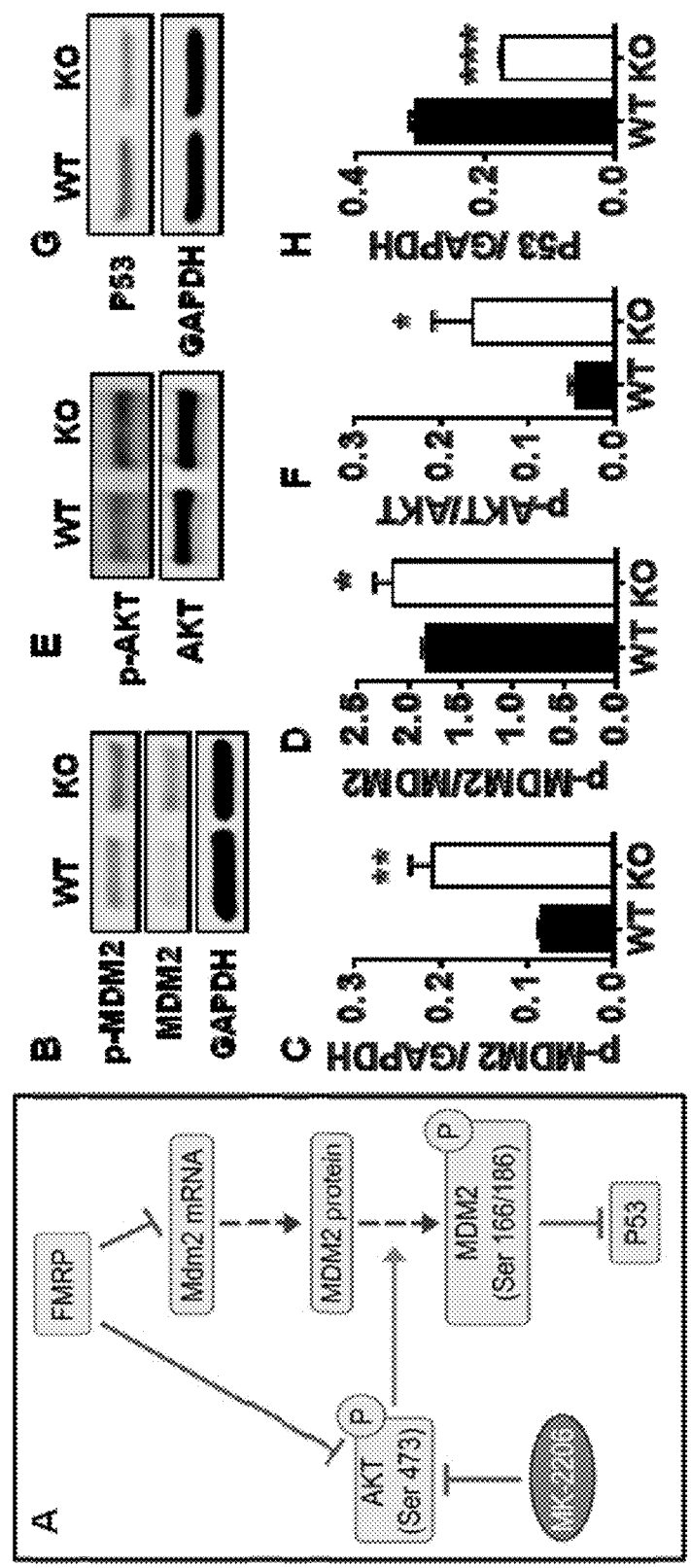

FMRP Regulates MDM2 Phosphorylation Through AKT Pathway:

The elevated MDM2 protein expression in Fmr1 KO NPCs prompted us to assess phosphorylated MDM2 (p-MDM2), the active form of MDM2 (FIG. 3A). MDM2 has multiple phosphorylation sites. Phosphorylation on serine 395 and 407 is known to regulate cell death (20), whereas phosphorylation of MDM2 on serine 166 and 186 is related to cell growth (21). Since we found no altered cell death or survival in Fmr1 KO NPCs compared to wildtype NPCs (FIG. 14), we assessed the phosphorylation of serine 166, which is known to be simultaneously phosphorylated with serine 186 by p-AKT in response to cell growth signals (22). We found that Fmr1 KO NPCs had more p-MDM2 (FIGS. 3B and 3C, p=0.0015, n=3, t-test) and a higher p-MDM2 to total MDM2 ratio (FIG. 3D) compared to wildtype NPCs, suggesting that increased p-MDM2 in Fmr1 KO NPCs may result from both increased total MDM2 protein expression and elevated phosphorylation. Activated AKT (AKT phosphorylated at serine 473 or threonine 308) is known to phosphorylate MDM2 at serine 166 and 186 (22), and FMRP deficiency results in increased AKT phosphorylation at Serine 473 in neurons (23). Elevated PI3K/AKT signaling in adult NSCs leads to increased NSC activation (24). We found that Fmr1 KO NPCs had a higher ratio of p-AKT to total AKT than wildtype NPCs (FIGS. 3E and 3F, p=0.013, n=3, t-test). Thus, Fmr1 KO NPCs have increased p-MDM2 due to both increased total MDM2 expression and elevated phosphorylation, possibly by p-AKT.

Figures 3A, 3B, 3C, 3D, 3E, 3F, 3G, 3H, 3I, 3J, 3K, 3L, 3M:
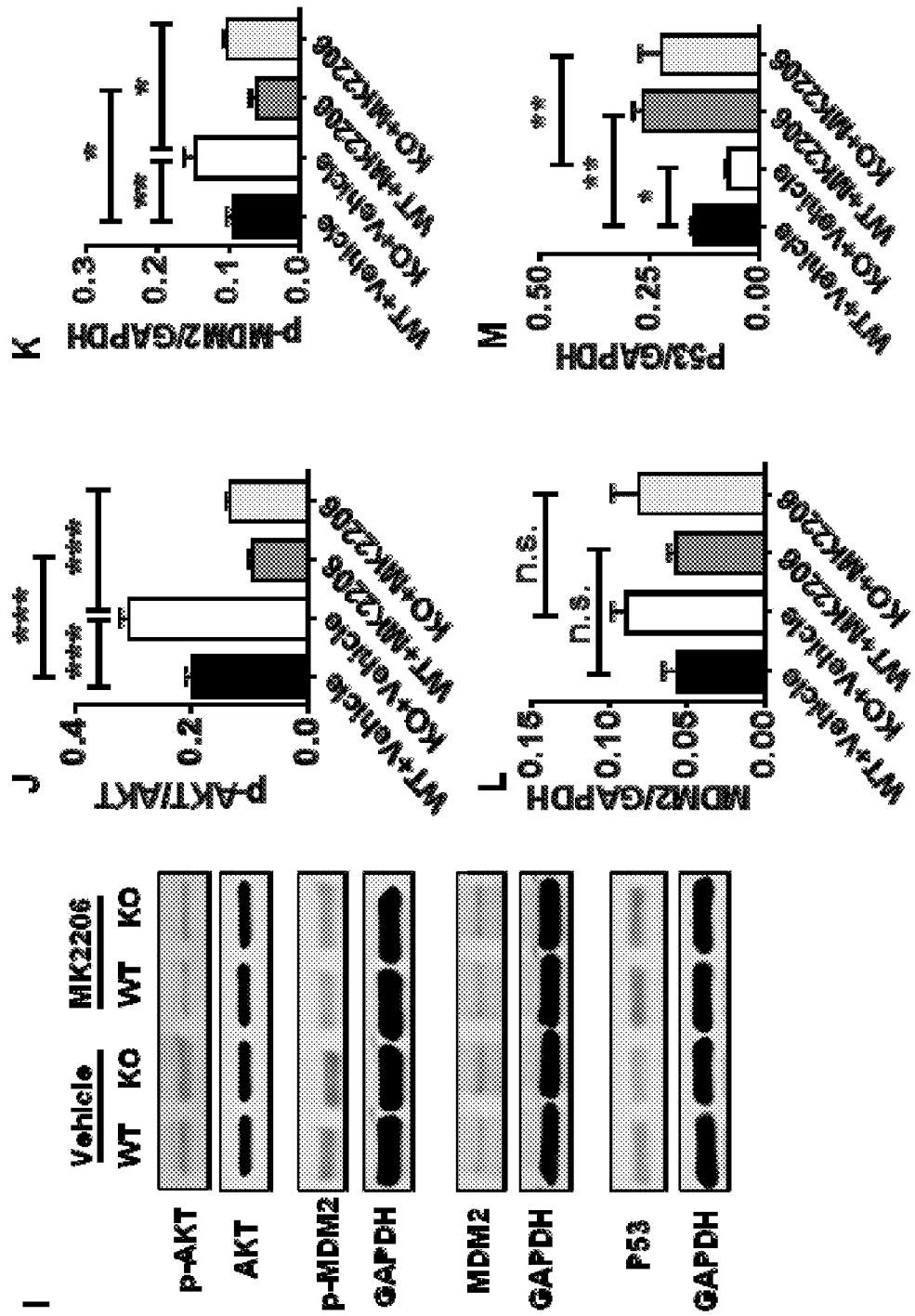

MDM2 is phosphorylated on Serine 166 in response to growth factor and mitogenic signaling, leading to increased MDM2-mediated ubiquitylation and degradation of P53 (25, 26). P53 is known to repress NSC activation (27), and we found that Fmr1 KO NPCs had reduced expression of P53 (FIGS. 3, G and H, p<0.0001, n=3, t-test). Treatment with MK-2206, a specific inhibitor of AKT phosphorylation (28) (FIG. 3A) led to reduced p-AKT (FIGS. 3I-3J) and reduced p-MDM2 (FIGS. 3I and 3K), without affecting total MDM2 (FIGS. 3I and 3L) in both KO and wildtype NPCs. Also, MK-2206 treatment enhanced P53 expression in Fmr1 KO NPCs (FIGS. 3I and 3M). Thus, in addition to controlling MDM2 expression through mRNA stability, FMRP also restricted the amount of p-MDM2 through the AKT pathway. The absence of FMRP led to increased p-MDM2 and subsequently reduced P53 in NPCs.

Figures 15A, 15B, 15C, 15D, 15E:
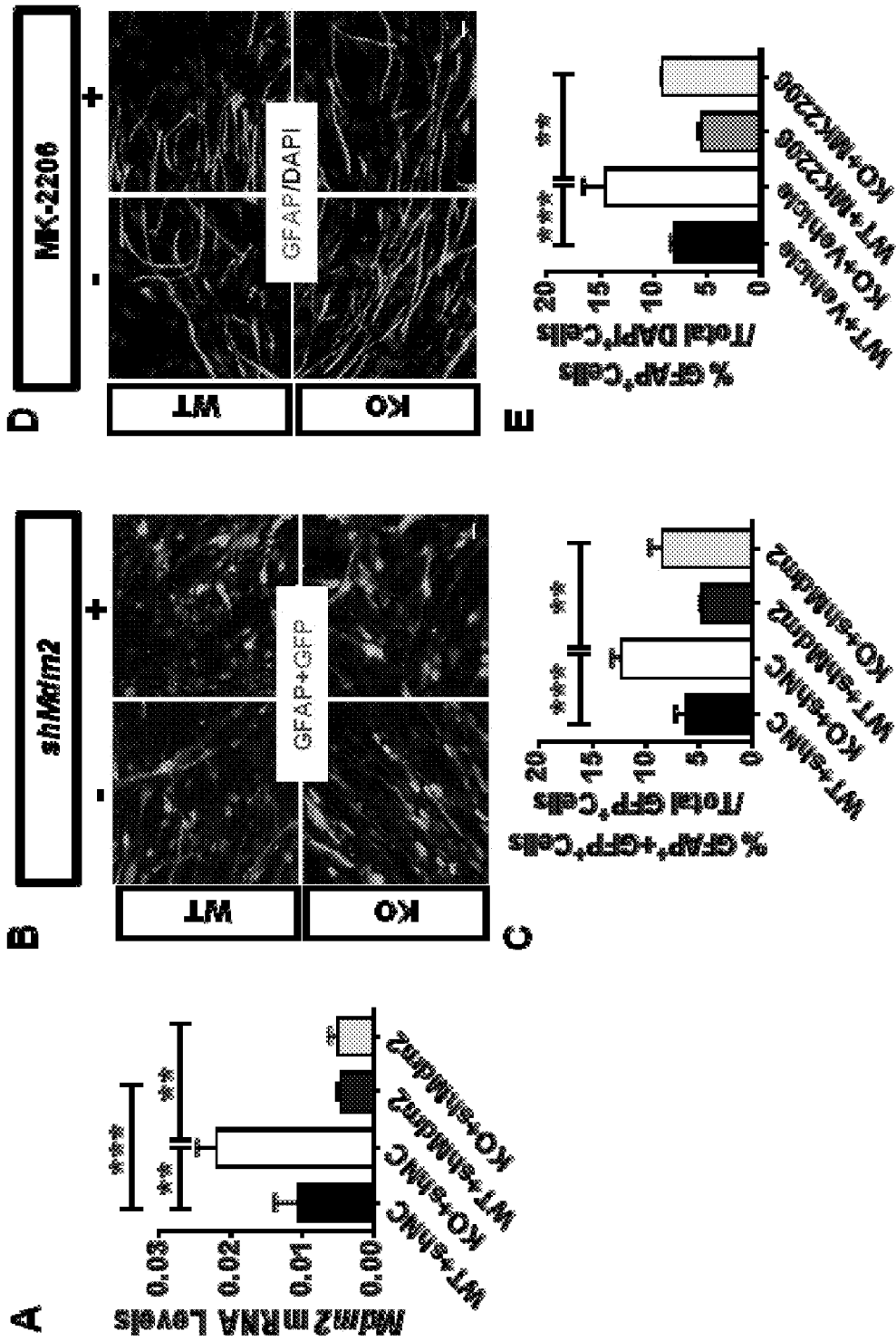
Figures 16A, 16B, 16C, 16D, 16E, 16F:
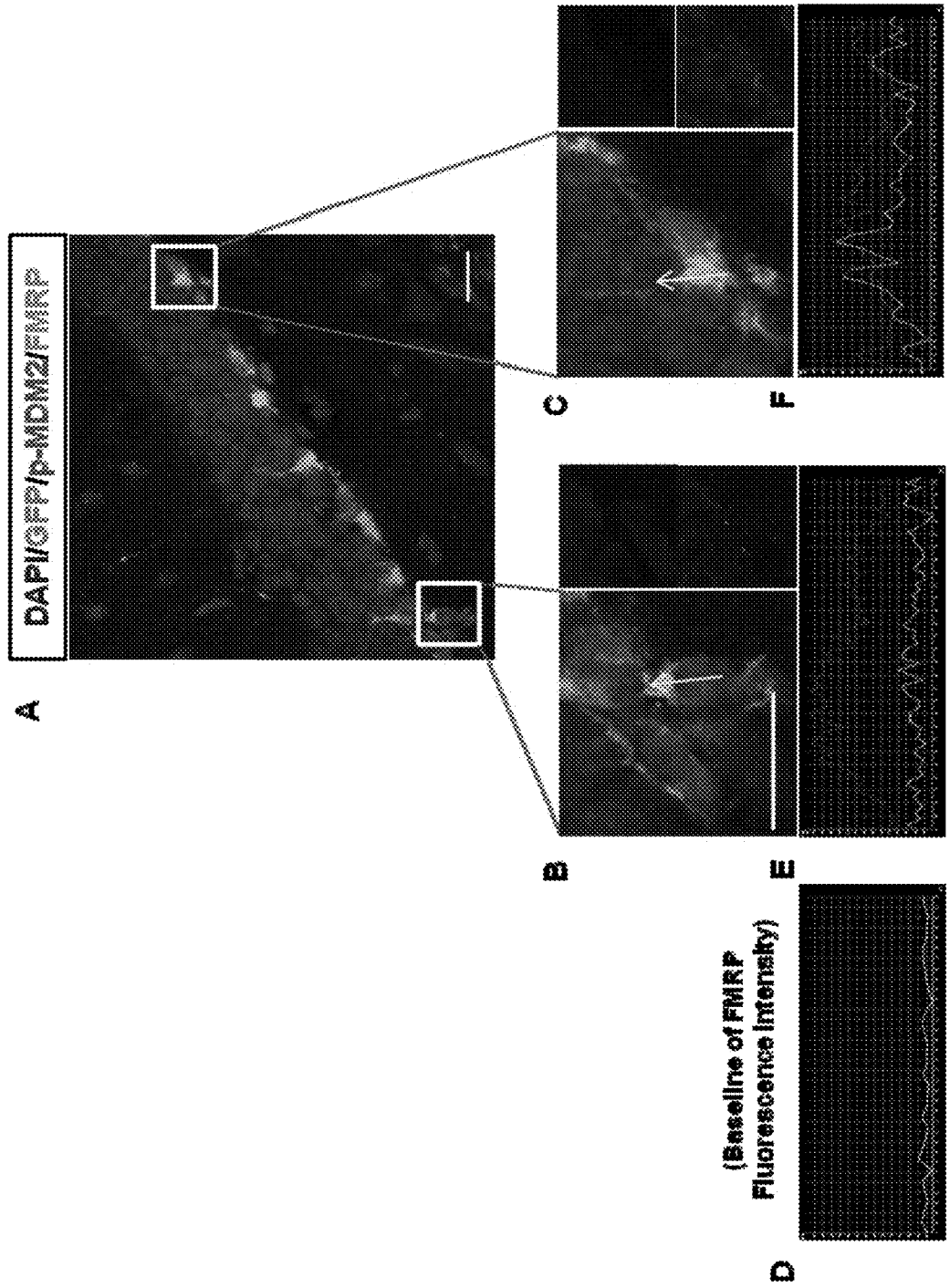
Figures 17A, 17B, 17C, 17D:
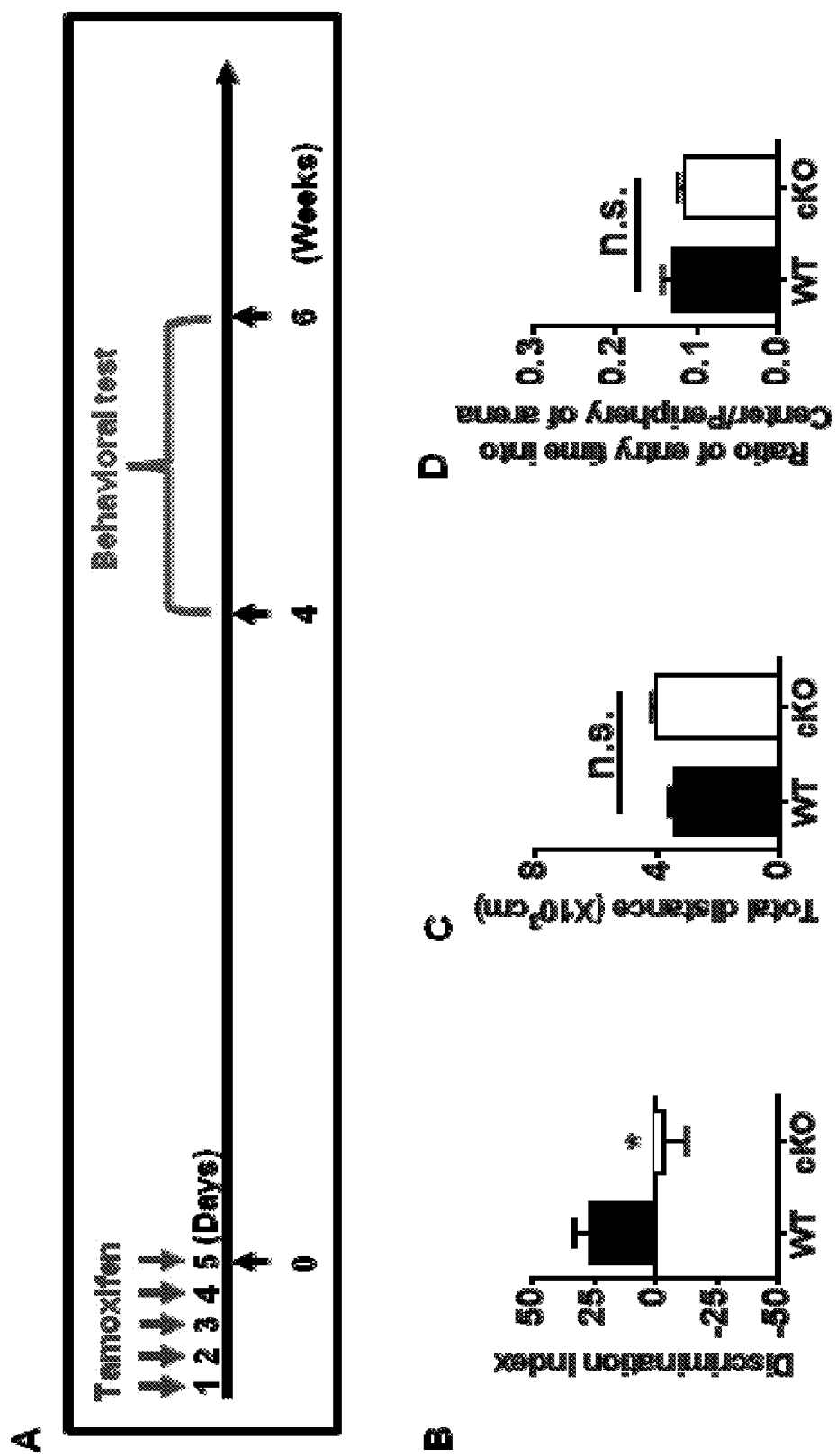

The Levels of MDM2 and p-MDM2 Directly Impact the Proliferation and Differentiation of aNPCs:

To investigate the effect of elevated p-MDM2 on the proliferation and differentiation of NPCs, we acutely knocked down MDM2 expression in NPCs using lentivirus expressing shRNA against Mdm2 (shMdm2, FIG. 4A and FIG. 15A). Lenti-shMdm2-treated NPCs had decreased total amounts of MDM2 and p-MDM2 (FIGS. 4B to 4E; C, P<0.01; D, p<0.05; E, p<0.05, n=3, One-Way ANOVA) and increased P53 (FIGS. 4F and 4G, p<0.01, n=3, One-Way ANOVA) compared to lenti-shNC (non-silencing control shRNA)-treated NPCs. We next investigated the impact of MDM2 knockdown on aNPC proliferation as assessed by BrdU pulse-labeling, and differentiation as assessed by cell lineage-specific antibodies, β-tubulin III (Tuj1) for neurons and GFAP for astrocytes. Acute knockdown of MDM2 (shMdm2) led to reduced cell proliferation in both wildtype and Fmr1 KO NPCs (FIGS. 4H-4I), increased neuronal differentiation (FIGS. 4J and 4K) and reduced astroglial differentiation (FIGS. 15B-15C) in both wildtype and Fmr1 KO NPCs. More importantly, the shMdm2 treatment restored the proliferation and differentiation of Fmr1 KO NPCs to that of wildtype (Lenti-shNC-treated) NPCs (FIGS. 4I and 4K). Thus, reducing MDM2 in NPCs rescued proliferation and differentiation deficits of FMRP-deficient NPCs.

We next investigated whether reducing MDM2 phosphorylation alone could also rescue the proliferation and differentiation of Fmr1 KO NPCs. We found that MK-2206 treatment resulted in decreased cell proliferation (FIGS. 4L and 4M) and astroglial differentiation (FIGS. 15D and 15E), but increased neuronal differentiation (FIGS. 4N and 4O) in both wildtype and Fmr1 KO NPCs. More importantly, MK-2206-treated Fmr1 KO NPCs exhibited similar proliferation and differentiation as vehicle-treated wildtype NPCs. Therefore, both reducing the expression of MDM2 and blocking MDM2 phosphorylation can rescue the proliferation and differentiation deficits of Fmr1 KO NPCs.

Figures 5A, 5B, 5C, 5D, 5E, 5F, 5G, 5H, 5I, 5J, 5K:
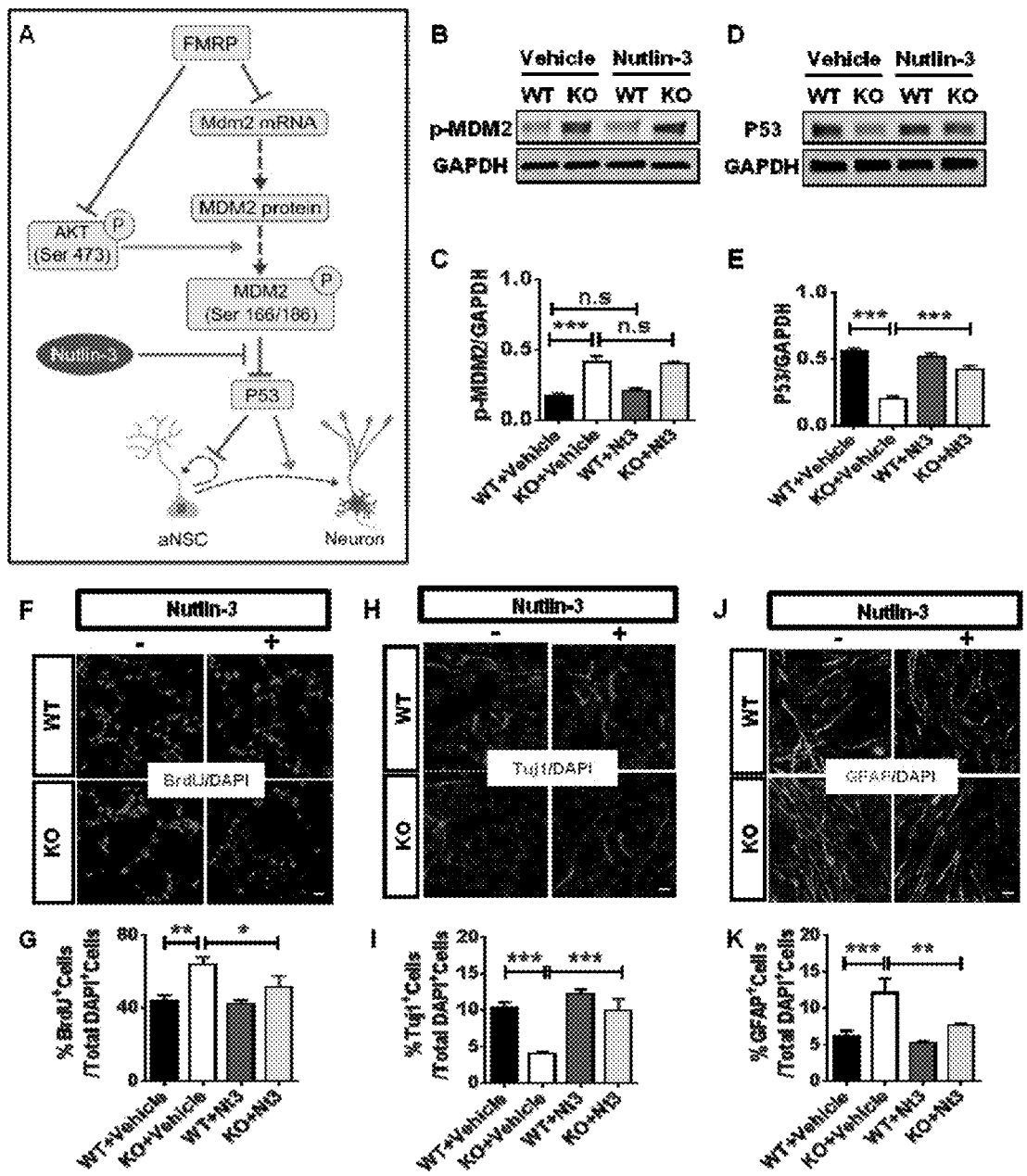
Figures 14A, 14B, 14C, 14D, 14E, 14F:
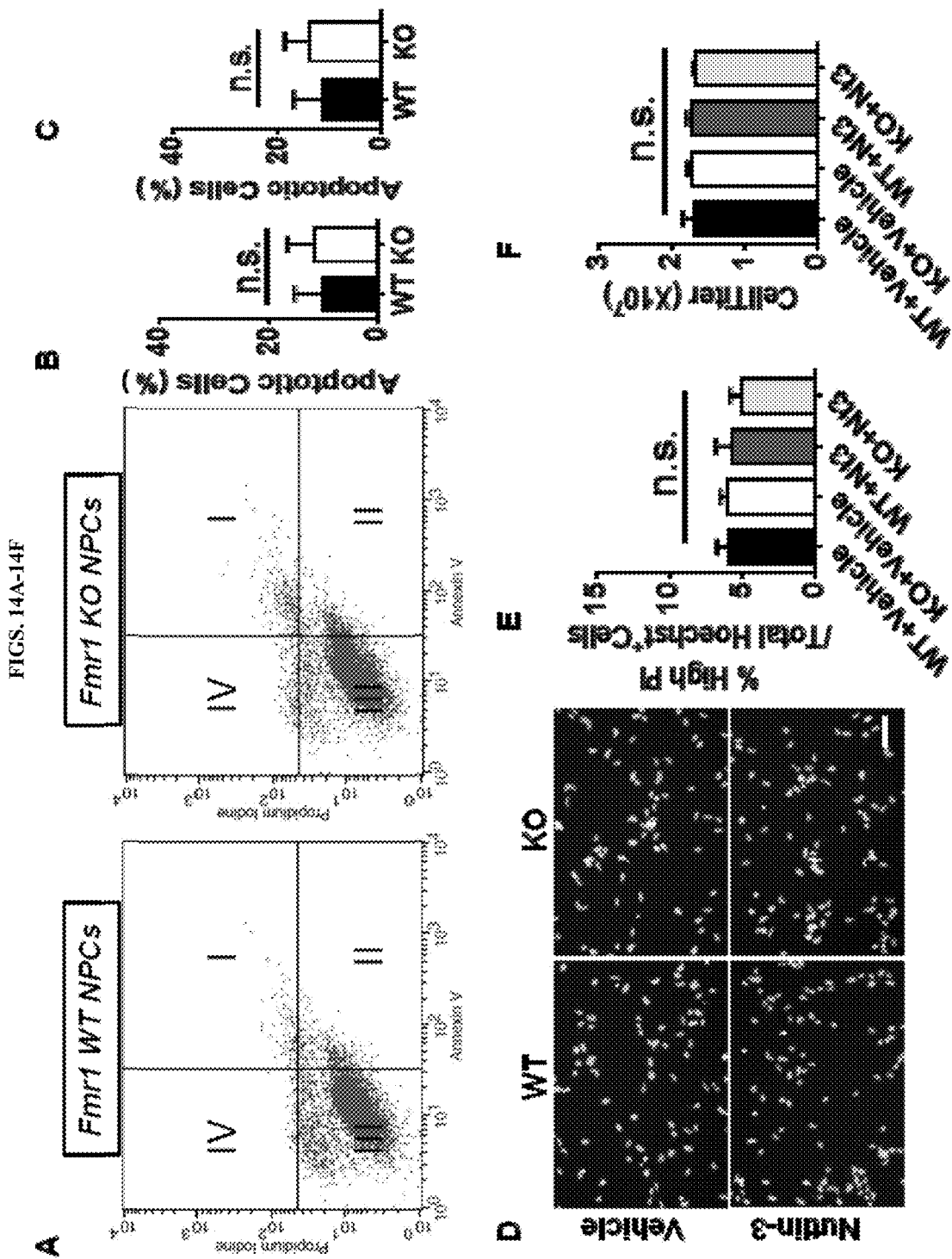

Nutlin-3 Treatment Rescues the Proliferation and Differentiation of aNPCs:

Although MK-2206 could correct the deficits of Fmr1 KO NPCs, its effects on wildtype NPCs raised concerns over potentially broad effects resulting from AKT pathway inhibition, with obvious potential therapeutic complications. We therefore searched for a specific inhibitor of MDM2 and found Nutlin-3, a potent MDM2 inhibitor that specifically interrupts MDM2 and P53 interactions (29, 30). Nutlin-3 has been evaluated extensively for its therapeutic potential and mechanism of action in human cancer and is currently in a phase 1 clinical trial for the treatment of retinoblastoma (31). We found that Nutlin-3 treatment did not affect p-MDM2 levels in either Fmr1 KO or wildtype cells (FIGS. 5A-5C), but led to increased P53 in KO cells with no significant effect on wildtype cells (FIGS. 5D and 5E). These data suggest that Nutlin3 treatment does not affect P-MDM2 protein levels but rather inhibits the activity of p-MDM2 towards its downstream targets such as P53. Next, we found that Nutlin-3 treatment reduced the proliferation and differentiation of Fmr1 KO NPCs without a significant effect on wildtype NPCs (FIGS. 5F-5K). Nutlin-3 also did not exhibit significant effects on cell death and survival of either KO or wildtype NPCs (FIGS. 14D-14F). Thus, Nutlin-3, a specific inhibitor of the MDM2-P53 interaction, can rescue the proliferation and differentiation of Fmr1 KO NPCs without affecting wildtype NPCs.

Figures 6A, 6B, 6C, 6D, 6E, 6F, 6G, 6H, 6I, 6J, 6K:
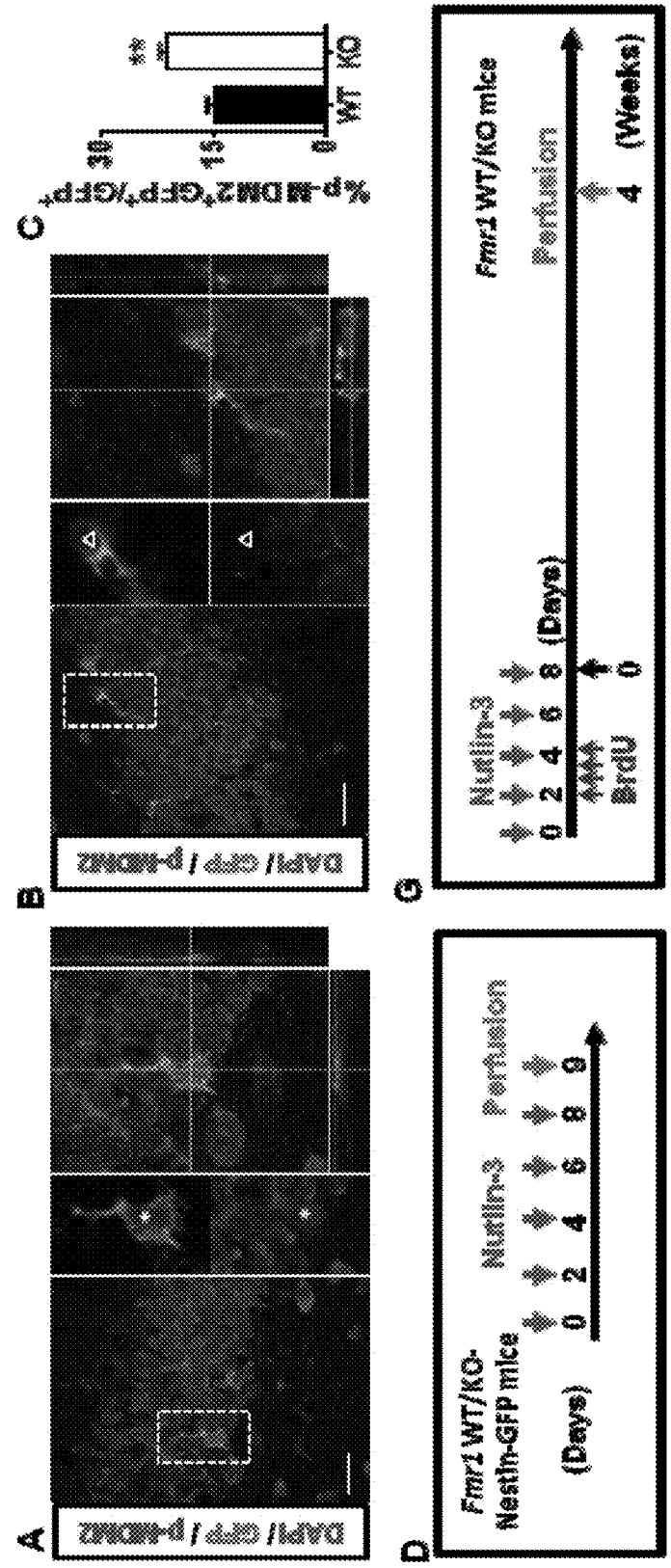
Figures 6A, 6B, 6C, 6D, 6E, 6F, 6G, 6H, 6I, 6J, 6K:
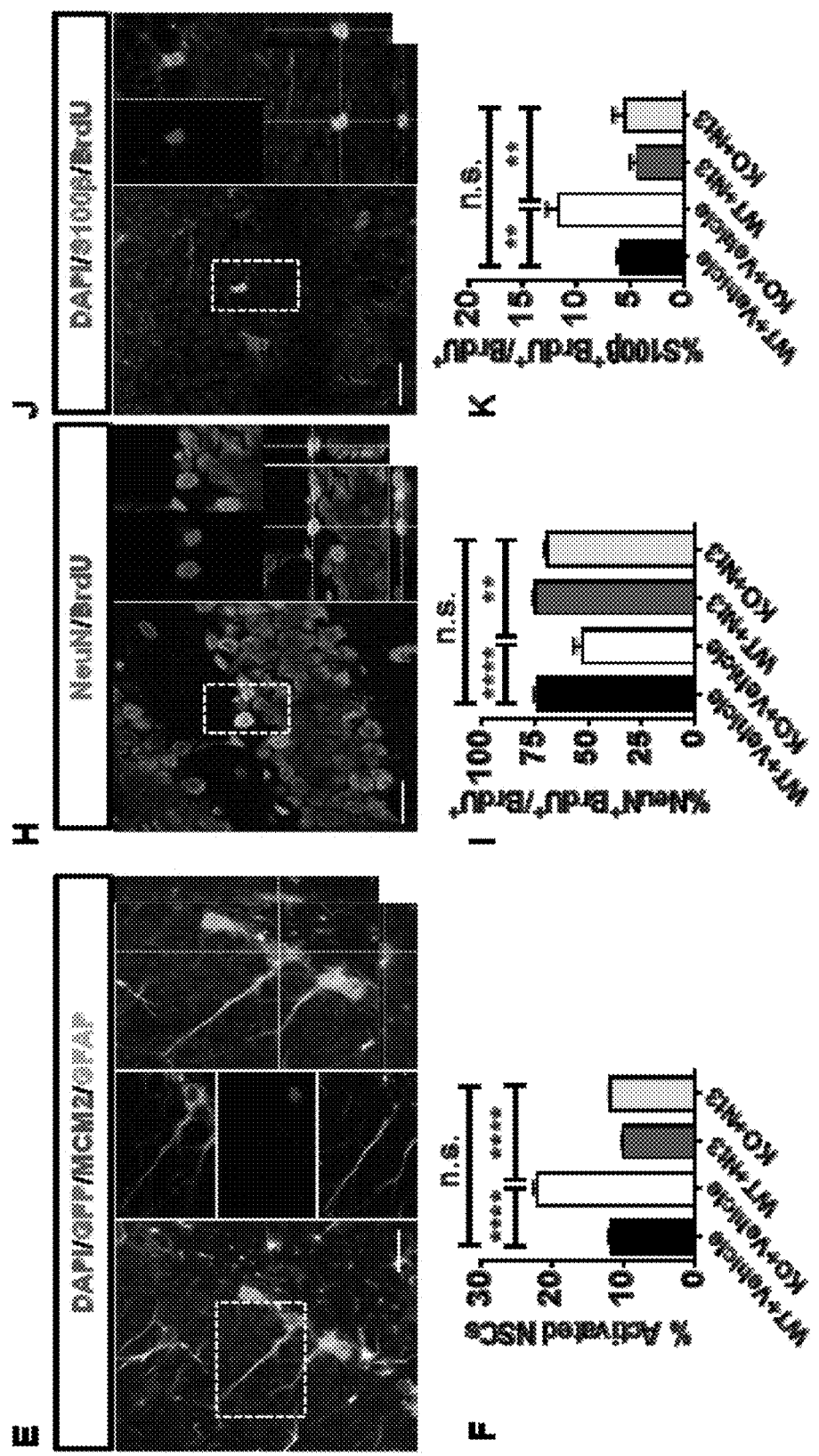

Nutlin-3 Treatment Rescues Neurogenic Deficits in Fmr1 KO Mice:

We next investigated whether Nutlin-3 could rescue the neurogenic deficits in Fmr1 KO mice. We found that in Fmr1 KO mice, the percentage of p-MDM2$^+$ cells among GFP$^+$ cells was significantly higher than that in Fmr1 wildtype mice (FIGS. 6A-6C, p=0.003, n=3, t-test). In addition, we found that in the brain of a female Fmr1$^{+/-}$::Nestin-GFP mouse in which half of the cells expressed FMRP while the other half of the cells did not due to X chromosome inactivation, FMRP and p-MDM2 expression exhibited an inverse relationship (FIG. 16). Nutlin-3 has been used in mice at high dosages (50 to 200 mg/kg) for 2 weeks or longer to examine its ability to block cancer cell growth in vivo (32-35). Since our goal was to correct rather than totally abolish NSC activation in the adult brain, we chose a 10 mg/kg dosage, which is the lowest dosage with known effects on in vivo cell proliferation (36). We also chose a shortened injection period based on the literature (37) and our experience (13). We treated Fmr1 KO and littermate wildtype mice with either vehicle or Nutlin-3 (10 mg/kg) every other day for 5 injections over 9 days. We found that Nutlin-3 treatment specifically reduced NSC activation in Fmr1 KO mice to wildtype levels (p<0.0001, n=3, One-Way ANOVA), with no significant effect on wildtype mice (n.s., n=3, One-Way ANOVA) (FIGS. 6E and 6F). Since FMRP deficiency impairs adult neurogenesis (11, 12), we next determined whether rebalancing NSC activation via Nutlin-3 treatment could rescue neuronal production (FIG. 6G). Mice received both Nutlin-3 treatment and BrdU injections to label dividing neural progenitors and were analyzed 4 weeks after the last Nutlin-3 treatment. Nutlin-3 treatment rescued both neuronal and astroglial differentiation in Fmr1 KO mice and brought them to levels similar to those of wildtype (vehicle-treatment) mice, without any significant effect on wildtype mice (FIGS. 6H-6K). These results suggest that Nutlin-3 treatment can correct NSC activation and rescue adult neurogenesis deficits in Fmr1 KO mice.

Figures 7A, 7B, 7C, 7D, 7E:
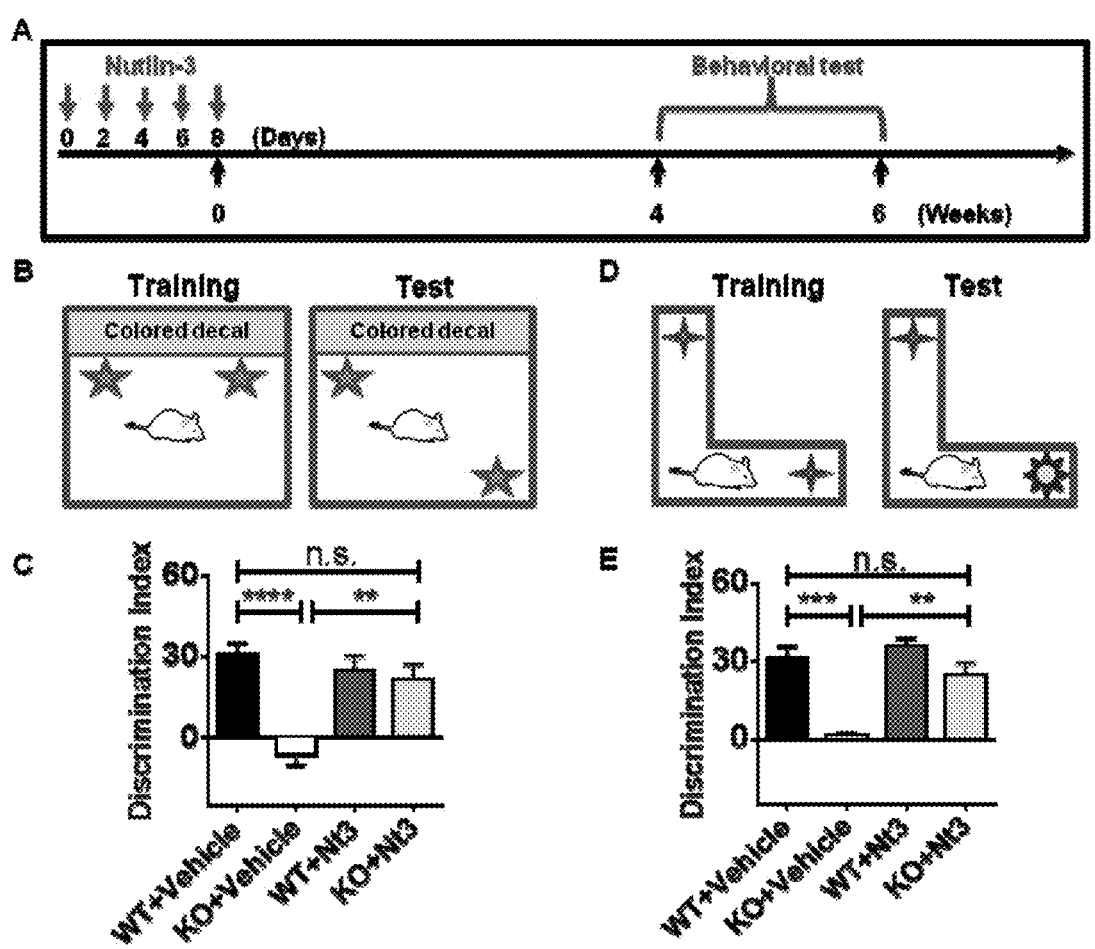
Figures 18A, 18B, 18C, 18D:
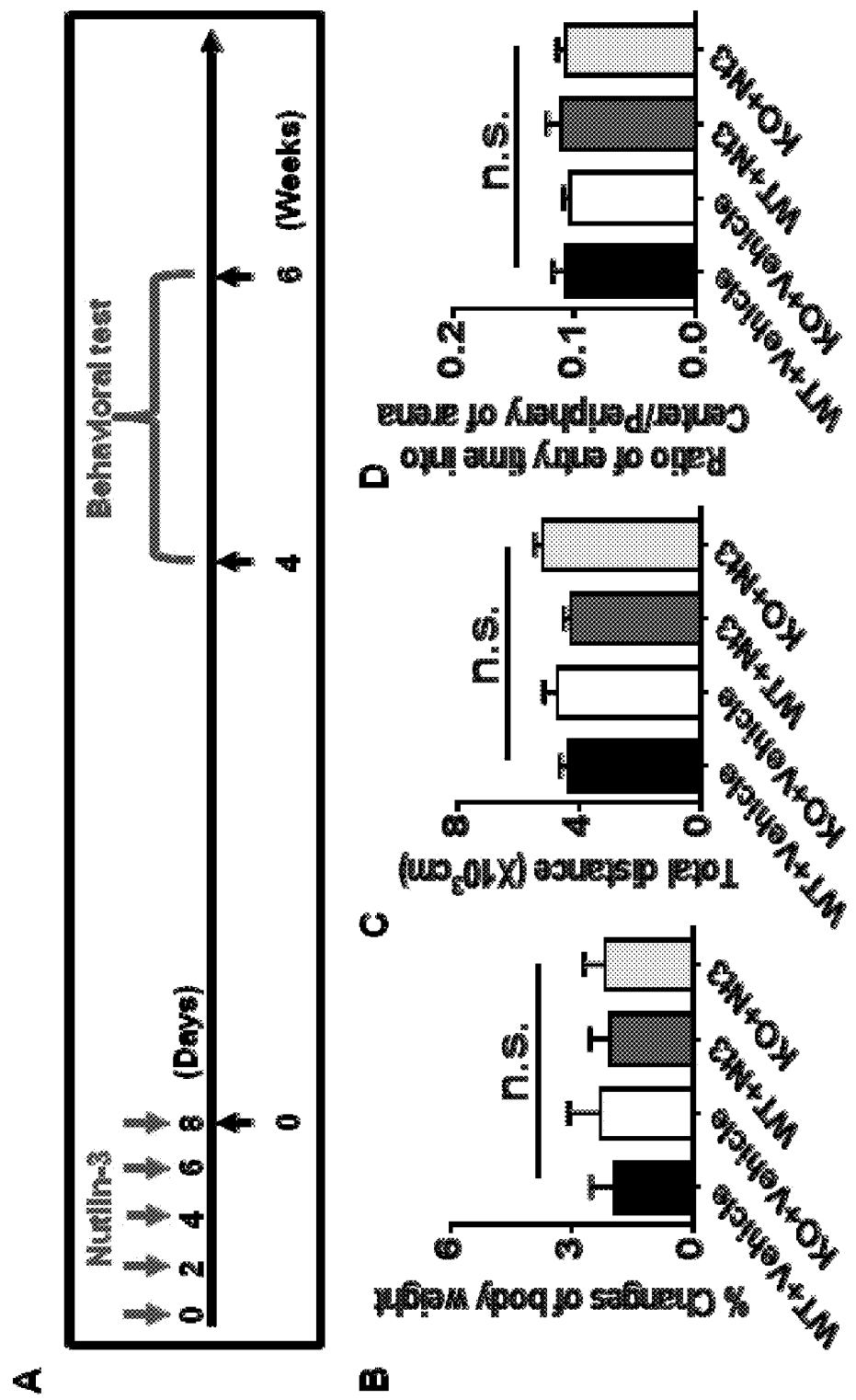
Figures 19A, 19B, 19C, 19D, 19E, 19F, 19G, 19H, 19I, 19J, 19K, 19L:
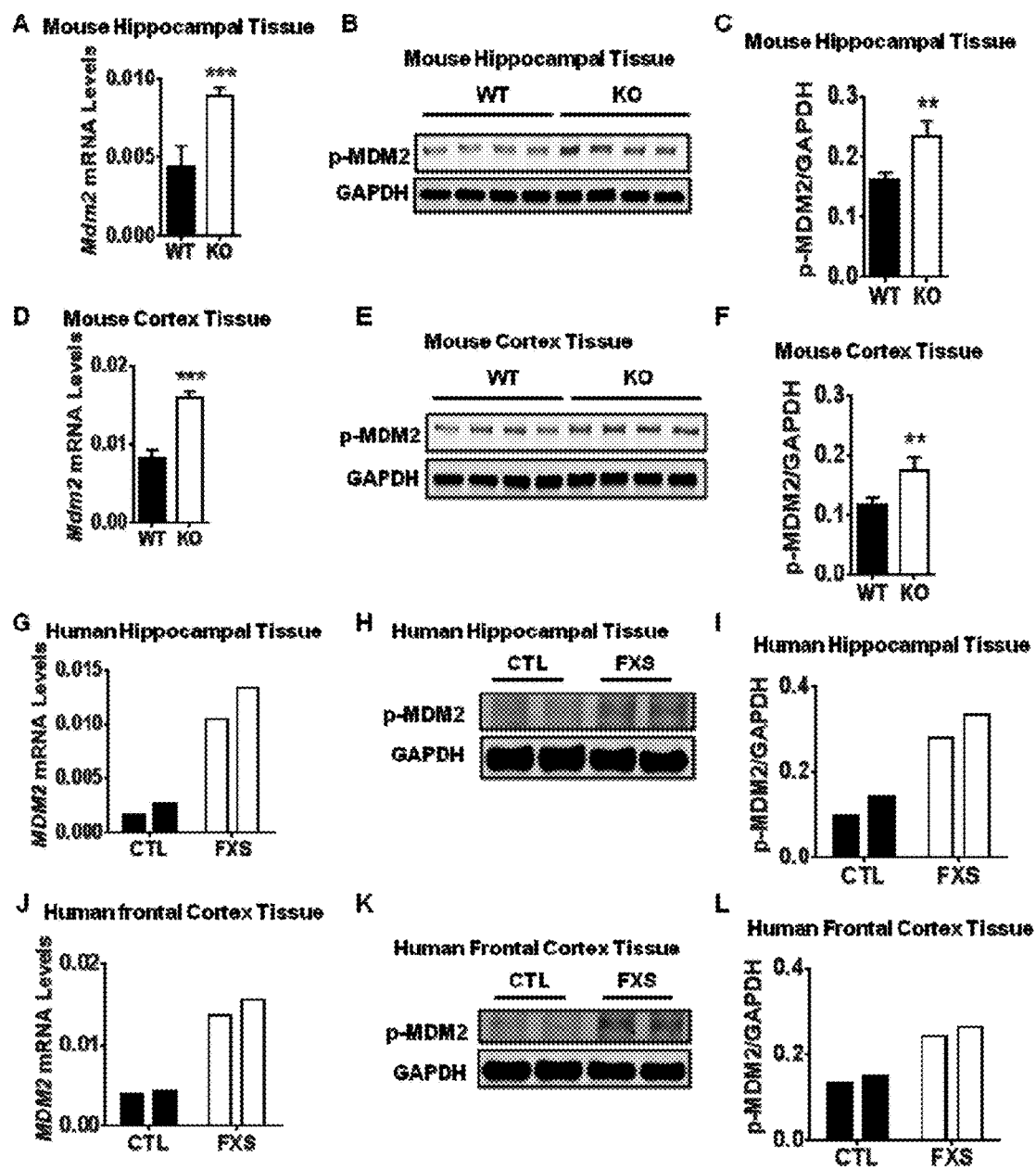

Nutlin-3 Treatment Rescues Cognitive Deficits in Fmr1 KO Mice:

We next investigated whether Nutlin-3 could reverse the behavioral deficits of Fmr1 KO mice. We showed previously that Fmr1 KO mice exhibited deficits in two hippocampus-dependent learning tasks: the delayed non-match to place radial arm maze (RAM) and trace conditioning (12, 13). However, these tests require stressful food restriction or electric shock, so we decided to employ two cognitive tests with minimal stress on the mice: the novel object recognition test and novel location test. First, using Fmr1 cKO::Cre::Ai14 triple transgenic mice (FIG. 9), we confirmed that mice with selective deletion of FMRP from adult NSCs and their progenies exhibited deficits in the novel location test (FIG. 17). This result corroborated our previous findings using the RAM test (12, 13) and validated the use of the novel location test for assessing spatial memory of FMRP-deficient mice. We then treated Fmr1 KO mice and their wildtype littermates with either vehicle or Nutlin-3 and analyzed their cognition 4 weeks later (FIG. 7A). Nutlin-3 had no significant effect on overall health and body weight (FIGS. 18A-18B) or locomotor activity and anxiety (FIGS. 18C-18D). Consistent with previous studies (18, 38, 39), Fmr1 KO mice exhibited both impaired spatial learning on the novel location test (FIGS. 7C-7D) and defective learning on the novel object recognition test (FIGS. 7D and 7E) compared to wildtype mice. Administration of Nutlin-3 rescued performance on both the novel location test (FIG. 7C, p<0.01, n=9 to 13/group, One-Way ANOVA) and the novel object recognition test (FIG. 7E, p<0.01, n=9 to 13/group, One-Way ANOVA) in Fmr1 KO mice, with no significant effect on wildtype mice. Therefore, Nutlin-3 treatment could rescue cognitive deficits of Fmr1 KO mice on these two tests. We found that, similar to Fmr1 KO mice, postmortem hippocampal and cortical tissues from patients with fragile X syndrome also exhibited higher MDM2 mRNA expression and p-MDM2 protein levels compared to those from age and gender-matched healthy controls (FIG. 19).

Discussion

In this study, we showed that FMRP plays an important role in adult NSC activation via MDM2 level control. We further demonstrated that specific inhibition of MDM2-P53 interaction with an FDA-approved small molecule rescues both the neurogenic and cognitive deficits of FXS mice. Our findings show for the first time that manipulating NSC activation can directly impact the production of mature neurons contributing to cognition. More importantly, since most adult brain cells are postmitotic, targeting a cell proliferation pathway in NSCs provides the much-needed specificity for therapeutic application.

Despite great efforts, there is no FDA-approved treatment for fragile X syndrome. Since FMRP is highly expressed in neurons, extensive research has naturally focused on neurons and has identified a number of neurotransmitter receptors and signaling pathways that are either targets or regulators of FMRP (2, 5). These discoveries led to the exciting development of potential drugs for fragile X syndrome. For example, lithium attenuates GSK3β activity, which reduces group 1 mGluR-dependent activation of protein translation (40). GSK3β inhibitors have been shown to improve cognition in a mouse model of fragile X syndrome (13, 41). GABA$_A$ receptor agonists reduce anxiety and audiogenic seizures in Fmr1 KO mice (42). Several mGluR5 antagonists, including Fenobam, RG7090 (Roche), AFQ056 (Novartis), CTEP, MPEP, and STX107 (Seaside Therapeutics), reverse multiple phenotypes in mouse models of fragile X syndrome (6). However, human clinical trials have yielded disappointing results. Although earlier open-label studies (e.g., Fenobam) showed promising effects, recent double-blind clinical trials for inhibitors of mGluR5 (RG7090, AFQ056, STX107), the best known fragile X drug target, yielded inconclusive results [summarized in (7)], highlighting the importance of searching for other cellular mechanisms and pathways. The contributions to fragile X syndrome of other cell types in the brain, such as glia and immune cells, are being actively pursued (1, 43). We have focused on the involvement of adult neurogenesis in fragile X syndrome. Although aNSCs constitute a small number of cells in the adult brain, FMRP deficiency in adult-born new neurons directly impacts cognition, and restoration of FMRP in adult new neurons rescues these deficits (12) (FIG. 15B). We further showed that inhibition of GSK3β, an FMRP target, rescues adult neurogenesis and learning deficits (44). These data suggest that targeting adult neurogenesis might be an effective treatment for certain cognition deficits in adult fragile X syndrome. However, GSK3β is involved in diverse biological processes in many types of brain cells, making drug specificity a major concern. A critical question has been whether treatment aimed at targeting adult NSCs could be an effective therapy for fragile X syndrome. In this study, we discovered that administration of a small molecule designed for cancer treatment, but used at a much lower dosage, could rebalance NSC activation and rescue the cognitive deficits in a mouse model of fragile X syndrome but with no apparent effect on wildtype mice.

Adult NSC activation is highly regulated; studies over the past two decades have identified a number of intrinsic regulators within NSCs and extrinsic factors provided by stem cell niche (8, 9). Most studies have focused on the role of NSC activation in the maintenance of NSCs, whereas the impact of NSC activation on mature neuron production has gone unexplored. We found that rebalancing NSC activation during the initial neurogenic phase could change terminal differentiation of NSCs into neurons and astrocytes (analyzed 30 days later). Therefore, correcting the imbalance in NSC activation versus-quiescence during the early stage of neurogenesis could have long-lasting effects on cell fate. Since most adult brain cells are postmitotic, targeting a cell proliferation pathway may restrict drug action largely to NSCs without significantly affecting postmitotic cells, yielding the desired specificity for therapy. There are, however, several limitations to our study. Complex social and language deficits in fragile X syndrome are ambiguously modeled in mice, and the effect of Nutlin-3 on these behaviors has not been evaluated. Although the Fmr1 KO mice used in our study recapitulate several key deficits in human fragile X syndrome, the neurocognitive impairment in mouse models of this disease is much milder than those seen in human patients, making it difficult to predict the therapeutic efficacy of Nutlin-3 treatment in preclinical trials.

MDM2 is an E3 ubiquitin ligase with many biological functions, from wound healing and carcinogenesis to tissue regeneration. MDM2 is activated via phosphorylation at multiple sites and the sites of phosphorylation are linked to distinct functions (45). Phosphorylation of MDM2 at Tyr394, Ser395, and Ser407 by ATM/ATR is stimulated by DNA damage, leading to inhibition of MDM2, which results in apoptosis. We found no significant difference in cell death between Fmr1 wildtype and KO NPCs. Therefore, we decided that MDM2 phosphorylation by ATM/ATR may have no significant role in Fmr1 KO NPCs. On the other hand, growth factor and mitogenic signaling trigger AKT phosphorylation of MDM2 at Ser166 and Ser186, leading to MDM2 activation and subsequent P53 ubiquitylation and degradation (25, 45). AKT activity is elevated in FMRP-deficient mouse brains and Drosophila neuroblasts (46-48), as well as in lymphoblastoid cells derived from patients with fragile X syndrome (47). Here, we found a dysregulated AKT-MDM2-P53 pathway in Fmr1 KO NPCs, and that inhibiting either AKT or the interaction of MDM2 with P53 restored P53 expression and rescued NPC proliferation and differentiation deficits in Fmr1 KO NPCs. AKT signaling is frequently dysregulated in human cancers, and MK-2206, a potent allosteric inhibitor of all AKT isoforms, has been used to treat patients with tumors in several clinical trials (49, 50). Although our study might extend the reach of MK-2206 to fragile X syndrome, one concern is the molecule's broad effects on many cellular processes in many types of cells. This concern is substantiated by our own observation that, although MK-2206 is highly effective in rescuing Fmr1 KO NPCs, it also has potent effects on NPCs in wildtype mice.

The MDM2-P53 interaction is not only necessary for early embryonic development (51, 52), but also is crucial for stem cell maintenance in adults (20). Particularly relevant to the present study, MDM2 is known to inhibit P53 activity and regulate adult NSC activation (16). Besides its well-described proapoptotic effect, P53 is implicated in nervous system development (53), and P53 null mice show deficits in learning and memory and behavioral alterations (54). We selected Nutlin-3 because it is a potent inhibitor specifically designed to inhibit MDM2-P53 interactions (29), has been evaluated extensively for its therapeutic potential and mechanism of action in human cancer (55), and is currently in phase 1 clinical trials for treating retinoblastoma (31). To limit the effect of Nutlin-3 on proliferating cells in mice, we chose a significantly lower dosage (10× lower) and shorter treatment scheme compared to those used for cancer treatment; our mice showed no obvious changes in health and behavior. We also observed that, unlike with MK-2206, Nutlin-3 treatment exhibited no effect on the NPCs of wildtype mice. Interestingly, although both Fmr1 KO mice and patients with fragile X syndrome exhibited elevated P-MDM2 in hippocampal and cortical brain tissues, similar to what we have seen in aNSCs, P53 expression was similar in mouse cortex and hippocampal tissues. Note that p53 expression was too low to be reliably assessed in human tissues. Therefore, it is likely that P53 is not a major target for MDM2 in mature neurons, which comprise a large proportion of cells in the brain tissue. It is not surprising that we found very low levels of P53 in cortex and hippocampus, especially in humans, because it has been shown that P53 expression is low in mature neurons and that elevated P53 in response to stress can lead to neuronal death (56). Therefore, our discovery of the widespread upregulation of P-MDM2 in fragile X syndrome human and mouse tissues with no apparent impact on P53 expression in neurons suggested that targeting p-MDM2 might be a promising new therapeutic method for treating fragile X syndrome. MDM2 has other substrates (57), such as PSD95 in neurons (58). Comprehensive identification of P-MDM2 targets in neurons and specific inhibitors for p-MDM2's interaction with these targets will be a fruitful area for translational research in fragile X syndrome. We do not rule out that in treated mice, Nutlin-3 may inhibit p-MDM2's interaction with targets other than P53 and may exert effects on other types of cells besides aNSCs, including mature neurons. However, Nutlin-3 was designed specifically to inhibit MDM2-P53 interactions, and much higher dosages would be needed before there will be an effect on other MDM2 targets (57). Since we used a low dose of Nutlin-3 in our study, the effects we observed are most likely to be through P53 inhibition in aNSCs compared to other targets or in mature cell types. Cell type-specific targeting of Nutlin-3 action will be required to validate the direct link between restoration of aNSC activity and cognitive rescue, however such methods are not yet available. The high specificity of Nutlin-3 towards FMRP-deficient NPCs without apparent effect on wildtype NPCs, along with the fact that most brain cells are postmitotic and therefore likely to be less sensitive to Nutlin-3, make it an attractive potential candidate for treating fragile X syndrome.

As shown in FIGS. 21A-21D, P53 protein expression was not significantly changed in the hippocampal and cortical tissues from Fmr1 KO mice. These results demonstrate that, in both Fmr1 KO mouse and human fragile X patient cortex, P53 down regulation is specific to NSCs.

By assessing cognitive functions in WT and Fmr1 knockout (KO) mice and Fmr1 conditional knockout mice (cKO) treated with Nutlin-3 at different time points (see FIGS. 22A-22H), we determined that Nutlin-3 treatment at 8 weeks of age had long lasting effects even when mice were assessed at 20 weeks of age (when mice are considered to be "middle aged"). These data build upon the results described above for assessment after four weeks and demonstrate that correcting NSCs by Nutlin-3 treatment has pronounced long term effects. Nutlin-3 treatment of 20 week old mice was also therapeutic for the fragile x mice, thus expanding the therapeutic age range of Nutlin-3.

As shown in FIGS. 23A-23C, Nutlin-3 derivative RG7112 was as effective as Nutlin-3 to rescue the proliferation and differentiation of FMRP-deficient NPCs in vitro. These data suggest that other Nutlin-3 derivatives or similar compounds may be efficacious for treatment of Fragile X. Moreover, as shown in FIG. 24, small molecules that are not Nutlin-3 derivatives but that act as inhibitors of MDM2 also have similar efficacy as Nutlin-3. These data suggest that other MDM2 inhibitors can be used for treatment of Fragile X syndrome.

REFERENCES

1. R. J. Hagerman, J. Polussa, Treatment of the psychiatric problems associated with fragile X syndrome. Curr Opin Psychiatry 28, 107-112 (2015).
2. T. Wang, S. M. Bray, S. T. Warren, New perspectives on the biology of fragile X syndrome. Curr Opin Genet Dev 22, 256-263 (2012).
3. M. Ascano, N. Mukherjee, P. Bandaru, J. B. Miller, J. D. Nusbaum, D. L. Corcoran, C. Langlois, M. Munschauer, S. Dewell, M. Hafner, Z. Williams, U. Ohler, T. Tuschl, FMRP targets distinct mRNA sequence elements to regulate protein expression. Nature 492, 382-+ (2012).
4. J. C. Darnell, S. J. Van Driesche, C. L. Zhang, K. Y. S. Hung, A. Mele, C. E. Fraser, E. F. Stone, C. Chen, J. J. Fak, S. W. Chi, D. D. Licatalosi, J. D. Richter, R. B. Darnell, FMRP Stalls Ribosomal Translocation on mRNAs Linked to Synaptic Function and Autism. Cell 146, 247-261 (2011).
5. A. Contractor, V. A. Klyachko, C. Portera-Cailliau, Altered Neuronal and Circuit Excitability in Fragile X Syndrome. Neuron 87, 699-715 (2015).
6. E. Berry-Kravis, Mechanism-Based Treatments in Neurodevelopmental Disorders: Fragile X Syndrome. Pediatr Neurol 50, 297-302 (2014).
7. A. Mullard, Fragile X disappointments upset autism ambitions. Nat Rev Drug Discov 14, 151-153 (2015).
8. S. Jessberger, F. H. Gage, Adult neurogenesis: bridging the gap between mice and humans. Trends Cell Biol 24, 558-563 (2014).
9. K. M. Christian, H. J. Song, G. L. Ming, Functions and Dysfunctions of Adult Hippocampal Neurogenesis. Annu Rev Neurosci 37, 243-262 (2014).
10. L. H. Li, H. Clevers, Coexistence of Quiescent and Active Adult Stem Cells in Mammals. Science 327, 542-545 (2010).
11. Y. P. Luo, G. Shan, W. X. Guo, R. D. Smrt, E. B. Johnson, X. K. Li, R. L. Pfeiffer, K. E. Szulwach, R. H. Duan, B. Z. Barkho, W. D. Li, C. M. Liu, P. Jin, X. Y. Zhao, Fragile X Mental Retardation Protein Regulates Proliferation and Differentiation of Adult Neural Stem/Progenitor Cells. PLoS Genet 6, (2010).
12. W. X. Guo, A. M. Allan, R. T. Zong, L. Zhang, E. B. Johnson, E. G. Schaller, A. C. Murthy, S. L. Goggin, A. J. Eisch, B. A. Oostra, D. L. Nelson, P. Jin, X. Y. Zhao, Ablation of Fmrp in adult neural stem cells disrupts hippocampus-dependent learning. Nat Med 17, 559-U575 (2011).
13. W. X. Guo, A. C. Murthy, L. Zhang, E. B. Johnson, E. G. Schaller, A. M. Allan, X. Y. Zhao, Inhibition of GSK3 beta improves hippocampus-dependent learning and rescues neurogenesis in a mouse model of fragile X syndrome. Hum Mol Genet 21, 681-691 (2012).
14. V. Brown, P. Jin, S. Ceman, J. C. Darnell, W. T. O'Donnell, S. A. Tenenbaum, X. K. Jin, Y. Feng, K. D. Wilkinson, J. D. Keene, R. B. Darnell, S. T. Warren, Microarray identification of FMRP-associated brain mRNAs and altered mRNA translational profiles in fragile X syndrome. Cell 107, 477-487 (2001).
15. R. W. Overall, M. Paszkowski-Rogacz, G. Kempermann, The mammalian adult neurogenesis gene ontology (MANGO) provides a structural framework for published information on genes regulating adult hippocampal neurogenesis. PLoS One 7, e48527 (2012).
16. S. Francoz, P. Froment, S. Bogaerts, S. De Clercq, M. Maetens, G. Doumont, E. Bellefroid, J. C. Marine, Mdm4 and Mdm2 cooperate to inhibit p53 activity in proliferating and quiescent cells in vivo. Proc Natl Acad Sci USA 103, 3232-3237 (2006).
17. R. Lu, H. P. Wang, Z. Liang, L. Ku, W. T. O'Donnell, W. Li, S. T. Warren, Y. Feng, The fragile X protein controls microtubule-associated protein 1B translation and microtubule stability in brain neuron development. Proc Natl Acad Sci USA 101, 15201-15206 (2004).
18. T. Udagawa, N. G. Fully, M. Jakovcevski, H. Kaphzan, J. M. Alarcon, S. Anilkumar, M. Ivshina, J. A. Hurt, K. Nagaoka, V. C. Nalavadi, L. J. Lorenz, G. J. Bassell, S. Akbarian, S. Chattarji, E. Klann, J. D. Richter, Genetic and acute CPEB1 depletion ameliorate fragile X pathophysiology. Nat Med 19, 1473-+ (2013).
19. S. De Rubeis, C. Bagni, Fragile X mental retardation protein control of neuronal mRNA metabolism: Insights into mRNA stability. Molecular and Cellular Neuroscience 43, 43-50 (2010).

20. H. S. Gannon, B. A. Woda, S. N. Jones, ATM phosphorylation of Mdm2 Ser394 regulates the amplitude and duration of the DNA damage response in mice. Cancer Cell 21, 668-679 (2012).
21. T. M. Gottlieb, J. F. M. Leal, R. Seger, Y. Taya, M. Oren, Cross-talk between Akt, p53 and Mdm2: possible implications for the regulation of apoptosis. Oncogene 21, 1299-1303 (2002).
22. L. D. Mayo, D. B. Donner, A phosphatidylinositol 3-kinase/Akt pathway promotes translocation of Mdm2 from the cytoplasm to the nucleus. Proc Natl Acad Sci USA 98, 11598-11603 (2001).
23. C. Gross, M. Nakamoto, X. D. Yao, C. B. Chan, S. Y. Yim, K. Q. Ye, S. T. Warren, G. J. Bassell, Excess Phosphoinositide 3-Kinase Subunit Synthesis and Activity as a Novel Therapeutic Target in Fragile X Syndrome. Journal of Neuroscience 30, 10624-10638 (2010).
24. M. A. Bonaguidi, M. A. Wheeler, J. S. Shapiro, R. P. Stadel, G. J. Sun, G. L. Ming, H. Song, In vivo clonal analysis reveals self-renewing and multipotent adult neural stem cell characteristics. Cell 145, 1142-1155 (2011).
25. Y. Ogawara, S. Kishishita, T. Obata, Y. Isazawa, T. Suzuki, K. Tanaka, N. Masuyama, Y. Gotoh, Akt enhances Mdm2-mediated ubiquitination and degradation of p53. Journal of Biological Chemistry 277, 21843-21850 (2002).
26. B. P. Zhou, Y. Liaq, W. Y. Xia, Y. Y. Zou, B. Spohn, M. C. Hung, HER-2/neu induces p53 ubiquitination via Akt-mediated MDM2 phosphorylation (vol 3, pg 973, 2001). Nat Cell Biol 4, 736-736 (2002).
27. Y. Wang, J. Yang, H. R. Zheng, G. J. Tomasek, P. Zhang, P. E. McKeever, E. Y. H. P. Lee, Y. Zhu, Expression of Mutant p53 Proteins Implicates a Lineage Relationship between Neural Stem Cells and Malignant Astrocytic Glioma in a Murine Model. Cancer Cell 15, 514-526 (2009).
28. V. A. Rafalski, P. P. Ho, J. O. Brett, D. Ucar, J. C. Dugas, E. A. Pollina, L. M. L. Chow, A. Ibrahim, S. J. Baker, B. A. Barres, L. Steinman, A. Brunet, Expansion of oligodendrocyte progenitor cells following SIRT1 inactivation in the adult brain. Nat Cell Biol 15, 614-+ (2013).
29. J. J. Manfredi, The Mdm2-p53 relationship evolves: Mdm2 swings both ways as an oncogene and a tumor suppressor. Genes Dev 24, 1580-1589 (2010).
30. L. T. Vassilev, B. T. Vu, B. Graves, D. Carvajal, F. Podlaski, Z. Filipovic, N. Kong, U. Kammlott, C. Lukacs, C. Klein, N. Fotouhi, E. A. Liu, In vivo activation of the p53 pathway by small-molecule antagonists of MDM2. Science 303, 844-848 (2004).
31. P. Secchiero, R. Bosco, C. Celeghini, G. Zauli, Recent advances in the therapeutic perspectives of Nutlin-3. Current pharmaceutical design 17, 569-577 (2011).
32. T. Zheng, D. Yin, Z. Lu, J. Wang, Y. Li, X. Chen, Y. Liang, X. Song, S. Qi, B. Sun, C. Xie, X. Meng, S. Pan, J. Liu, H. Jiang, L. Liu, Nutlin-3 overcomes arsenic trioxide resistance and tumor metastasis mediated by mutant p53 in Hepatocellular Carcinoma. Mol Cancer 13, 133 (2014).
33. A. Kunkele, K. De Preter, L. Heukamp, T. Thor, K. W. Pajtler, W. Hartmann, M. Mittelbronn, M. A. Grotzer, H. E. Deubzer, F. Speleman, A. Schramm, A. Eggert, J. H. Schulte, Pharmacological activation of the p53 pathway by nutlin-3 exerts anti-tumoral effects in medulloblastomas. Neuro Oncol 14, 859-869 (2012).
34. C. Tovar, J. Rosinski, Z. Filipovic, B. Higgins, K. Kolinsky, H. Hilton, X. Zhao, B. T. Vu, W. Qing, K. Packman, O. Myklebost, D. C. Heimbrook, L. T. Vassilev, Small-molecule MDM2 antagonists reveal aberrant p53 signaling in cancer: implications for therapy. Proc Natl Acad Sci USA 103, 1888-1893 (2006).
35. F. Ye, A. A. Lattif, J. Xie, A. Weinberg, S. Gao, Nutlin-3 induces apoptosis, disrupts viral latency and inhibits expression of angiopoietin-2 in Kaposi sarcoma tumor cells. Cell Cycle 11, 1393-1399 (2012).
36. N. Mouraret, E. Marcos, S. Abid, G. Gary-Bobo, M. Saker, A. Houssaini, J. L. Dubois-Rande, L. Boyer, J. Boczkowski, G. Derumeaux, V. Amsellem, S. Adnot, Activation of lung p53 by Nutlin-3a prevents and reverses experimental pulmonary hypertension. Circulation 127, 1664-1676 (2013).
37. M. O. Zhou, W. D. Li, S. Huang, J. Song, J. Y. Kim, X. L. Tian, E. C. Kang, Y. Sano, C. Liu, J. Balaji, S. M. Wu, Y. Zhou, Y. Zhou, S. N. Parivash, D. Ehninger, L. He, H. J. Song, G. L. Ming, A. J. Silva, mTOR Inhibition Ameliorates Cognitive and Affective Deficits Caused by Disc1 Knockdown in Adult-Born Dentate Granule Neurons. Neuron 77, 647-654 (2013).
38. A. Busquets-Garcia, M. Gomis-Gonzalez, T. Guegan, C. Agustin-Pavon, A. Pastor, S. Mato, A. Perez-Samartin, C. Matute, R. de la Torre, M. Dierssen, R. Maldonado, A. Ozaita, Targeting the endocannabinoid system in the treatment of fragile X syndrome. Nat Med 19, 603-607 (2013).
39. M. K. King, R. S. Jope, Lithium treatment alleviates impaired cognition in a mouse model of fragile X syndrome. Genes Brain and Behavior 12, 723-731 (2013).
40. C. J. Yuskaitis, M. A. Mines, M. K. King, J. D. Sweatt, C. A. Miller, R. S. Jope, Lithium ameliorates altered glycogen synthase kinase-3 and behavior in a mouse model of Fragile X syndrome. Biochem Pharmacol 79, 632-646 (2010).
41. A. V. Franklin, M. K. King, V. Palomo, A. Martinez, L. L. McMahon, R. S. Jope, Glycogen synthase kinase-3 inhibitors reverse deficits in long-term potentiation and cognition in fragile X mice. Biol Psychiatry 75, 198-206 (2014).
42. I. Heulens, C. D'Hulst, D. Van Dam, P. P. De Deyn, R. F. Kooy, Pharmacological treatment of fragile X syndrome with GABAergic drugs in a knockout mouse model. Behav Brain Res 229, 244-249 (2012).
43. Y. Li, X. Zhao, Concise review: Fragile X proteins in stem cell maintenance and differentiation. Stem Cells 32, 1724-1733 (2014).
44. W. Guo, A. C. Murthy, L. Zhang, E. B. Johnson, E. G. Schaller, A. M. Allan, X. Zhao, Inhibition of GSK3beta improves hippocampus-dependent learning and rescues neurogenesis in a mouse model of fragile X syndrome. Hum Mol Genet 21, 681-691 (2012).
45. D. W. Meek, T. R. Hupp, The regulation of MDM2 by multisite phosphorylation—opportunities for molecular-based intervention to target tumours? Semin Cancer Biol 20, 19-28 (2010).
46. C. Gross, N. Raj, G. Molinaro, A. G. Allen, A. J. Whyte, J. R. Gibson, K. M. Huber, S. L. Gourley, G. J. Bassell, Selective role of the catalytic PI3K subunit p110beta in impaired higher order cognition in fragile X syndrome. Cell Rep 11, 681-688 (2015).
47. C. Gross, G. J. Bassell, Excess protein synthesis in FXS patient lymphoblastoid cells can be rescued with a p110beta-selective inhibitor. Mol Med 18, 336-345 (2012).
48. M. A. Callan, N. Clements, N. Ahrendt, D. C. Zarnescu, Fragile X Protein is required for inhibition of insulin signaling and regulates glial-dependent neuroblast reactivation in the developing brain. Brain Res 1462, 151-161 (2012).
49. D. H. Ahn, J. Li, L. Wei, A. Doyle, J. L. Marshall, L. J. Schaaf, M. A. Phelps, M. A. Villalona-Calero, T. Bekaii-Saab, Results of an abbreviated phase-II study with the Akt Inhibitor MK-2206 in Patients with Advanced Biliary Cancer. Sci Rep 5, 12122 (2015).
50. P. N. Lara, Jr., J. Longmate, P. C. Mack, K. Kelly, M. A. Socinski, R. Salgia, B. Gitlitz, T. Li, M. Koczywas, K. L. Reckamp, D. R. Gandara, Phase II Study of the AKT inhibitor MK-2206 plus Erlotinib in Patients with Advanced Non-Small Cell Lung Cancer who Previously Progressed on Erlotinib. Clin Cancer Res, (2015).
51. S. N. Jones, A. E. Roe, L. A. Donehower, A. Bradley, Rescue of embryonic lethality in Mdm2-deficient mice by absence of p53. Nature 378, 206-208 (1995).
52. R. Montes de Oca Luna, D. S. Wagner, G. Lozano, Rescue of early embryonic lethality in mdm2-deficient mice by deletion of p53. Nature 378, 203-206 (1995).
53. A. Tedeschi, S. Di Giovanni, The non-apoptotic role of p53 in neuronal biology: enlightening the dark side of the moon. EMBO Rep 10, 576-583 (2009).
54. R. Amson, J. M. Lassalle, H. Halley, S. Prieur, F. Lethrosne, J. P. Roperch, D. Israeli, M. C. Gendron, C. Duyckaerts, F. Checler, J. Dausset, D. Cohen, M. Oren, A. Telerman, Behavioral alterations associated with apoptosis and down-regulation of presenilin 1 in the brains of p53-deficient mice. Proc Natl Acad Sci USA 97, 5346-5350 (2000).
55. J. C. Carry, C. Garcia-Echeverria, Inhibitors of the p53/hdm2 protein-protein interaction-path to the clinic. Bioorg Med Chem Lett 23, 2480-2485 (2013).
56. R. S. Morrison, Y. Kinoshita, The role of p53 in neuronal cell death. Cell Death Differ 7, 868-879 (2000).
57. S. Wang, Y. Zhao, D. Bernard, A. Aguilar, S. Kumar, in Protein-Protein Interactions, M. D. Wendt, Ed. (Springer Berlin Heidelberg, 2012), pp. pp 57-79.
58. N. P. Tsai, J. R. Wilkerson, W. Guo, M. A. Maksimova, G. N. DeMartino, C. W. Cowan, K. M. Huber, Multiple autism-linked genes mediate synapse elimination via proteasomal degradation of a synaptic scaffold PSD-95. Cell 151, 1581-1594 (2012).
59. T. D.-B. F. X. Consortium, Fmr1 knockout mice: a model to study fragile X mental retardation. The Dutch-Belgian Fragile X Consortium. Cell 78, 23-33 (1994).
60. M. Yamaguchi, H. Saito, M. Suzuki, K. Mori, Visualization of neurogenesis in the central nervous system using nestin promoter-GFP transgenic mice. Neuroreport 11, 1991-1996 (2000).
61. W. X. Guo, L. Zhang, D. M. Christopher, Z. Q. Teng, S. R. Fausett, C. M. Liu, O. L. George, J. Klingensmith, P. Jin, X. Y. Zhao, RNA-Binding Protein FXR2 Regulates Adult Hippocampal Neurogenesis by Reducing Noggin Expression. Neuron 70, 924-938 (2011).
62. W. X. Guo, E. D. Polich, J. Su, Y. Gao, D. M. Christopher, A. M. Allan, M. Wang, F. F. Wang, G. F. Wang, X. Y. Zhao, Fragile X Proteins FMRP and FXR2P Control Synaptic GluA1 Expression and Neuronal Maturation via Distinct Mechanisms. Cell Rep 11, 1651-1666 (2015).
63. B. D. Eadie, W. N. Zhang, F. Boehme, J. Gil-Mohapel, L. Kainer, J. M. Simpson, B. R. Christie, Fmr1 knockout mice show reduced anxiety and alterations in neurogenesis that are specific to the ventral dentate gyrus. Neurobiol Dis 36, 361-373 (2009).
64. W. X. Guo, N. E. Patzlaff, E. M. Jobe, X. Y. Zhao, Isolation of multipotent neural stem or progenitor cells from both the dentate gyrus and subventricular zone of a single adult mouse. Nat Protoc 7, 2005-2012 (2012).
65. A. Contestabile, B. Greco, D. Ghezzi, V. Tucci, F. Benfenati, L. Gasparini, Lithium rescues synaptic plasticity and memory in Down syndrome mice. J Clin Invest 123, 348-361 (2013).
66. Y. Wang, J. Yang, H. Zheng, G. J. Tomasek, P. Zhang, P. E. McKeever, E. Y. Lee, Y. Zhu, Expression of mutant p53 proteins implicates a lineage relationship between neural stem cells and malignant astrocytic glioma in a murine model. Cancer cell 15, 514-526 (2009).
67. E. Bruel-Jungerman, A. Veyrac, F. Dufour, J. Horwood, S. Laroche, S. Davis, Inhibition of PI3K-Akt signaling blocks exercise-mediated enhancement of adult neurogenesis and synaptic plasticity in the dentate gyrus. PloS one 4, e7901 (2009).
68. K. Shimozaki, C. L. Zhang, H. Suh, A. M. Denli, R. M. Evans, F. H. Gage, SRY-box-containing gene 2 regulation of nuclear receptor tailless (Tlx) transcription in adult neural stem cells. The Journal of biological chemistry 287, 5969-5978 (2012).
69. R. Favaro, M. Valotta, A. L. Ferri, E. Latorre, J. Mariani, C. Giachino, C. Lancini, V. Tosetti, S. Ottolenghi, V. Taylor, S. K. Nicolis, Hippocampal development and neural stem cell maintenance require Sox2-dependent regulation of Shh. Nature neuroscience 12, 1248-1256 (2009).
70. S. Ahn, A. L. Joyner, In vivo analysis of quiescent adult neural stem cells responding to Sonic hedgehog. Nature 437, 894-897 (2005).
71. K. Mizutani, K. Yoon, L. Dang, A. Tokunaga, N. Gaiano, Differential Notch signalling distinguishes neural stem cells from intermediate progenitors. Nature 449, 351-355 (2007).
72. J. L. Ables, N. A. Decarolis, M. A. Johnson, P. D. Rivera, Z. Gao, D. C. Cooper, F. Radtke, J. Hsieh, A. J. Eisch, Notch1 is required for maintenance of the reservoir of adult hippocampal stem cells. The Journal of neuroscience: the official journal of the Society for Neuroscience 30, 10484-10492 (2010).
73. O. Ehm, C. Goritz, M. Covic, I. Schaffner, T. J. Schwarz, E. Karaca, B. Kempkes, E. Kremmer, F. W. Pfrieger, L. Espinosa, A. Bigas, C. Giachino, V. Taylor, J. Frisen, D. C. Lie, RBPJkappa-dependent signaling is essential for long-term maintenance of neural stem cells in the adult hippocampus. The Journal of neuroscience: the official journal of the Society for Neuroscience 30, 13794-13807 (2010).
74. S. Francoz, P. Froment, S. Bogaerts, S. De Clercq, M. Maetens, G. Doumont, E. Bellefroid, J. C. Marine, Mdm4 and Mdm2 cooperate to inhibit p53 activity in proliferating and quiescent cells in vivo. Proceedings of the National Academy of Sciences of the United States of America 103, 3232-3237 (2006).
75. K. Khodosevich, Y. Watanabe, H. Monyer, EphA4 preserves postnatal and adult neural stem cells in an undifferentiated state in vivo. Journal of cell science 124, 1268-1279 (2011).
76. A. Lavado, O. V. Lagutin, L. M. Chow, S. J. Baker, G. Oliver, Prox1 is required for granule cell maturation and intermediate progenitor maintenance during brain neurogenesis. PLoS biology 8, (2010).
77. T. Yoshimatsu, D. Kawaguchi, K. Oishi, K. Takeda, S. Akira, N. Masuyama, Y. Gotoh, Non-cell-autonomous action of STAT3 in maintenance of neural precursor cells in the mouse neocortex. Development 133, 2553-2563 (2006).

78. P. Zhu, R. Hata, F. Cao, F. Gu, Y. Hanakawa, K. Hashimoto, M. Sakanaka, Ramified microglial cells promote astrogliogenesis and maintenance of neural stem cells through activation of Stat3 function. FASEB journal: official publication of the Federation of American Societies for Experimental Biology 22, 3866-3877 (2008).
79. C. Andreu-Agullo, J. M. Morante-Redolat, A. C. Delgado, I. Farinas, Vascular niche factor PEDF modulates Notch-dependent stemness in the adult subependymal zone. Nature neuroscience 12, 1514-1523 (2009).
80. S. Muller, B. P. Chakrapani, H. Schwegler, H. D. Hofmann, M. Kirsch, Neurogenesis in the dentate gyms depends on ciliary neurotrophic factor and signal transducer and activator of transcription 3 signaling. Stem cells 27, 431-441 (2009).
81. Y. G. Han, N. Spassky, M. Romaguera-Ros, J. M. Garcia-Verdugo, A. Aguilar, S. Schneider-Maunoury, A. Alvarez-Buylla, Hedgehog signaling and primary cilia are required for the formation of adult neural stem cells. Nature neuroscience 11, 277-284 (2008).
82. F. Talos, A. Abraham, A. V. Vaseva, L. Holembowski, S. E. Tsirka, A. Scheel, D. Bode, M. Dobbelstein, W. Bruck, U. M. Moll, p73 is an essential regulator of neural stem cell maintenance in embryonal and adult CNS neurogenesis. Cell death and differentiation 17, 1816-1829 (2010).

We claim:

1. A method of treating a cognitive deficit, comprising administering an effective amount of a MDM2-p53 pathway inhibitor selected from the group consisting of a cis-imidazole compound, a benzodiazepine, and a spiro-oxindole compound to a subject afflicted with at least one cognitive deficit associated with a Fmr1 genetic defect, whereby administration of the inhibitor improves, enhances, or rescues the at least one cognitive deficit in the subject.

2. The method of claim 1, wherein the cognitive deficit is a memory deficit or learning deficit.

3. The method of claim 1, wherein the Fmr1 genetic defect comprises a full mutation FXS allele.

4. The method of claim 3, wherein the Fmr1 genetic defect comprises a pre-mutation FXS allele.

5. The method of claim 1, wherein the subject has or is suspected of having Fragile X Syndrome (FXS).

6. The method of claim 1, wherein the cognitive deficit is associated with aberrant neurogenesis.

7. The method of claim 1, wherein administration of the inhibitor increases neurogenesis in the subject.

8. A method of treating a neurogenic deficit, comprising administering an effective amount of a MDM2-p53 pathway inhibitor selected from the group consisting of a cis-imidazole compound, a benzodiazepine, and a spiro-oxindole compound to a subject afflicted with at least one neurogenic deficit associated with a Fmr1 genetic defect, whereby administration of the inhibitor improves, enhances, or rescues the at least one neurogenic deficit in the subject.

9. The method of claim 1, wherein the cis-imidazole compound is selected from the group consisting of Nutlin-3, Nutlin-3a, and RG7112.

10. The method of claim 1, wherein the neurogenic deficit is associated with aberrant adult neurogenesis.

11. The method of claim 1, wherein administration of the inhibitor increases neuronal and astroglial differentiation in the subject.

* * * * *

UNITED STATES PATENT AND TRADEMARK OFFICE
CERTIFICATE OF CORRECTION

PATENT NO. : 10,350,204 B2
APPLICATION NO. : 15/915278
DATED : July 16, 2019
INVENTOR(S) : Xinyu Zhao et al.

It is certified that error appears in the above-identified patent and that said Letters Patent is hereby corrected as shown below:

In the Specification

Column 2, Line 35, "gyms" should be --gyrus--.

Column 2, Line 37, "gyms" should be --gyrus--.

Column 2, Line 40, "gyms" should be --gyrus--.

Column 2, Line 44, "gyms" should be --gyrus--.

Column 2, Line 49, "gyms" should be --gyrus--.

Column 2, Line 52, "gyms" should be --gyrus--.

Column 2, Line 54, "gyms" should be --gyrus--.

Column 2, Line 61, "gyms" should be --gyrus--.

Column 2, Line 67, "gyms" should be --gyrus--.

Column 3, Line 2, "gyms" should be --gyrus--.

Column 4, Line 48, "gyms" should be --gyrus--.

Column 4, Line 56, "gyms" should be --gyrus--.

Column 4, Line 60, "gyms" should be --gyrus--.

Column 5, Line 24, "gyms" should be --gyrus--.

Signed and Sealed this
Tenth Day of September, 2019

Andrei Iancu
*Director of the United States Patent and Trademark Office*

CERTIFICATE OF CORRECTION (continued)
U.S. Pat. No. 10,350,204 B2

Column 5, Line 25, "gyms" should be --gyrus--.

Column 5, Line 27, "gyms" should be --gyrus--.

Column 5, Line 29, "gyms" should be --gyrus--.

Column 5, Line 31, "gyms" should be --gyrus--.

Column 5, Line 34, "gyms" should be --gyrus--.

Column 5, Line 39, "gyms" should be --gyrus--.

Column 5, Line 50, "gyms without" should be --gyrus without--.

Column 5, Line 50, "gyms volume" should be --gyrus volume--.

Column 5, Line 59, "gyms" should be --gyrus--.

Column 5, Line 61, "gyms" should be --gyrus--.

Column 10, Line 22, "gyms" should be --gyrus--.

Column 16, Line 60, "gyms" should be --gyrus--.

Column 16, Line 63, "gyms" should be --gyrus--.

Column 18, Line 50, "gyms" should be --gyrus--.

Column 18, Line 53, "gyms" should be --gyrus--.

Column 18, Line 59, "gyms" should be --gyrus--.

Column 19, Line 37, "gyms" should be --gyrus--.

Column 21, Line 35, "51061" should be --S1061--.

Column 21, Line 37, "57489" should be --S7489--.

Column 24, Line 66, "gyms" should be --gyrus--.

Column 25, Line 1, "gyms" should be --gyrus--.

Column 25, Line 16, "gyms" should be --gyrus--.

Column 25, Line 20, "gyms" should be --gyrus--.

CERTIFICATE OF CORRECTION (continued)
U.S. Pat. No. 10,350,204 B2

Column 25, Line 25, "gyms" should be --gyrus--.

Column 25, Line 44, "gyms" should be --gyrus--.

Column 26, Line 31, "gyms" should be --gyrus--.

Column 34, Line 58, "Fully" should be --Farny--.

Column 37, Line 64, "gyms" should be --gyrus--.

Column 38, Line 1, "gyms" should be --gyrus--.

Column 38, Line 15, "gyms" should be --gyrus--.

Column 39, Line 12, "gyms" should be --gyrus--.

SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: synthetic

<400> SEQUENCE: 1
agcagcgagt ccacagaga                                              19

<210> SEQ ID NO 2
<211> LENGTH: 20
<212> TYPE: DNA
<213> ORGANISM: Artificial Sequence
<220> FEATURE:
<223> OTHER INFORMATION: synthetic

<400> SEQUENCE: 2
atcctgatcc aggcaatcac                                             20

<210> SEQ ID NO 3
<211> LENGTH: 20
<212> TYPE: DNA
<213> ORGANISM: Artificial Sequence
<220> FEATURE:
<223> OTHER INFORMATION: synthetic

<400> SEQUENCE: 3
ggcaagatgg ggtatagaga                                             20

<210> SEQ ID NO 4
<211> LENGTH: 20
<212> TYPE: DNA
<213> ORGANISM: Artificial Sequence
<220> FEATURE:
<223> OTHER INFORMATION: synthetic

<400> SEQUENCE: 4
cccacctgct ttggtatttg                                             20

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
gggacagtgg tgtggatcag                                             20

```
<210> SEQ ID NO 6
<211> LENGTH: 20
<212> TYPE: DNA
<213> ORGANISM: Artificial Sequence
<220> FEATURE:
<223> OTHER INFORMATION: synthetic

<400> SEQUENCE: 6
cttgttggtg ttcctaggac                                          20

<210> SEQ ID NO 7
<211> LENGTH: 23
<212> TYPE: DNA
<213> ORGANISM: Artificial Sequence
<220> FEATURE:
<223> OTHER INFORMATION: synthetic

<400> SEQUENCE: 7
gctcctccct gttccagaga cgg                                      23

<210> SEQ ID NO 8
<211> LENGTH: 22
<212> TYPE: DNA
<213> ORGANISM: Artificial Sequence
<220> FEATURE:
<223> OTHER INFORMATION: synthetic

<400> SEQUENCE: 8
acaatctcca ctttgccact gc                                       22

<210> SEQ ID NO 9
<211> LENGTH: 21
<212> TYPE: DNA
<213> ORGANISM: Artificial Sequence
<220> FEATURE:
<223> OTHER INFORMATION: synthetic

<400> SEQUENCE: 9
gcagtgaatc tacagggacg c                                        21

<210> SEQ ID NO 10
<211> LENGTH: 21
<212> TYPE: DNA
<213> ORGANISM: Artificial Sequence
<220> FEATURE:
<223> OTHER INFORMATION: synthetic

<400> SEQUENCE: 10
atcctgatcc aaccaatcac c                                        21

<210> SEQ ID NO 11
<211> LENGTH: 23
<212> TYPE: DNA
<213> ORGANISM: Artificial Sequence
<220> FEATURE:
<223> OTHER INFORMATION: synthetic

<400> SEQUENCE: 11
gctcctccct gttccagaga cgg                                      23

<210> SEQ ID NO 12
<211> LENGTH: 22
<212> TYPE: DNA
<213> ORGANISM: Artificial Sequence
<220> FEATURE:
<223> OTHER INFORMATION: synthetic
```

```
<400> SEQUENCE: 12
acaatctcca ctttgccact gc                                          22

<210> SEQ ID NO 13
<211> LENGTH: 20
<212> TYPE: DNA
<213> ORGANISM: Artificial Sequence
<220> FEATURE:
<223> OTHER INFORMATION: synthetic

<400> SEQUENCE: 13
tccttattcc ctcttggcag                                             20

<210> SEQ ID NO 14
<211> LENGTH: 22
<212> TYPE: DNA
<213> ORGANISM: Artificial Sequence
<220> FEATURE:
<223> OTHER INFORMATION: synthetic

<400> SEQUENCE: 14
atggaagcta cattagcggt tt                                          22
```